(12) United States Patent  
Dadgar et al.

(10) Patent No.: US 12,312,576 B2  
(45) Date of Patent: May 27, 2025

(54) SYSTEM FOR DELIVERY OF A PAYLOAD INTO A CELL

(71) Applicant: STEMCELL TECHNOLOGIES CANADA INC., Vancouver (CA)

(72) Inventors: Maisam Dadgar, Cambridge, MA (US); Tarek Abdeljawad, Concord, MA (US); Howard Bernstein, Cambridge, MA (US)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 439 days.

(21) Appl. No.: 16/954,113

(22) PCT Filed: Dec. 18, 2018

(86) PCT No.: PCT/US2018/066295  
§ 371 (c)(1),  
(2) Date: Jun. 16, 2020

(87) PCT Pub. No.: WO2019/126212  
PCT Pub. Date: Jun. 27, 2019

(65) Prior Publication Data  
US 2020/0332243 A1    Oct. 22, 2020

Related U.S. Application Data

(60) Provisional application No. 62/608,202, filed on Dec. 20, 2017.

(51) Int. Cl.  
*C12M 1/42*     (2006.01)  
*B01L 3/00*     (2006.01)  
(Continued)

(52) U.S. Cl.  
CPC ....... *C12M 35/04* (2013.01); *B01L 3/502715* (2013.01); *C12M 23/16* (2013.01);  
(Continued)

(58) Field of Classification Search  
CPC ... B01L 2300/046; C12M 35/04; C12M 23/16  
See application file for complete search history.

(56) References Cited

U.S. PATENT DOCUMENTS 5,877,023 A * 3/1999 Sautter ............... C12N 15/89  
                                                    800/278  
2011/0003325 A1* 1/2011 Durack ............... B01L 3/5027  
                                                    435/29  
(Continued)

FOREIGN PATENT DOCUMENTS

JP    2004-125777 A    4/2004  
JP    2016-057309 A    4/2016  
(Continued)

OTHER PUBLICATIONS

A. Sharei et al: "A vector-free microfluidic platform for intracellular delivery", Proceedings of the National Academy of Sciences of the United States of America, vol. 110, No. 6, Jan. 22, 2013 (Jan. 22, 2013), pp. 2082-2087, XP055551255,.

(Continued)

*Primary Examiner* — Kathryn Elizabeth Limbaugh  
(74) *Attorney, Agent, or Firm* — SMART & BIGGAR LP; Micheline Gravelle

(57) ABSTRACT

A system for delivering a payload to a cell that includes: a platform supporting an input container, an output container, and a receiver for receiving all or part of a disposable assembly, the disposable assembly including a preparation vessel and a constriction cartridge. The preparation vessel holds a cell suspension as it is prepared for passage through one or more cell-deforming constrictions, and the constriction cartridge houses a component that includes the one or more cell deforming constrictions. Passage through the cell-deforming constrictions causes perturbations in cell membranes to allow entry of a payload into the cells. The system includes one or more processors configured to (Continued)

receive input from a user and to automatically control pressure, temperature, agitation, and/or flow of the cell suspension as it passes through the input container, through the preparation vessel, through the constriction cartridge, and to the output container.

22 Claims, 49 Drawing Sheets

(51) Int. Cl.
*C12M 3/06* (2006.01)
*G01N 1/31* (2006.01)

(52) U.S. Cl.
CPC .......... *G01N 1/31* (2013.01); *B01L 2300/046* (2013.01); *B01L 2300/0816* (2013.01)

(56) References Cited

U.S. PATENT DOCUMENTS

| | | | |
|---|---|---|---|
| 2011/0256574 A1 | 10/2011 | Zhang et al. | |
| 2012/0064518 A1* | 3/2012 | Diefenbach | C12N 13/00 435/363 |
| 2014/0287509 A1 | 9/2014 | Sharei et al. | |
| 2016/0018347 A1* | 1/2016 | Drbal | A61M 1/34 210/647 |
| 2016/0313332 A1* | 10/2016 | Lee | B03C 1/0332 |
| 2017/0173373 A1 | 6/2017 | Wagner et al. | |
| 2017/0335313 A1* | 11/2017 | Qian | C12Q 1/6806 |

FOREIGN PATENT DOCUMENTS

| | | | | |
|---|---|---|---|---|
| WO | WO-2017070169 A1 * | 4/2017 | .......... | B01L 3/50273 |
| WO | 2017161210 A1 | 9/2017 | | |
| WO | WO-2017173373 A1 * | 10/2017 | ........ | B01L 3/502746 |
| WO | 2017210334 A1 | 12/2017 | | |

OTHER PUBLICATIONS

Williams A R et al: "Filtroporation: A simple, reliable technique for transfection and macromolecular loading of cells In suspension", Biotechnology and Bioengineering, Wiley, vol. 65, No. 3, Nov. 5, 1999 (Nov. 5, 1999), pp. 341-346, XP002223170.

* cited by examiner

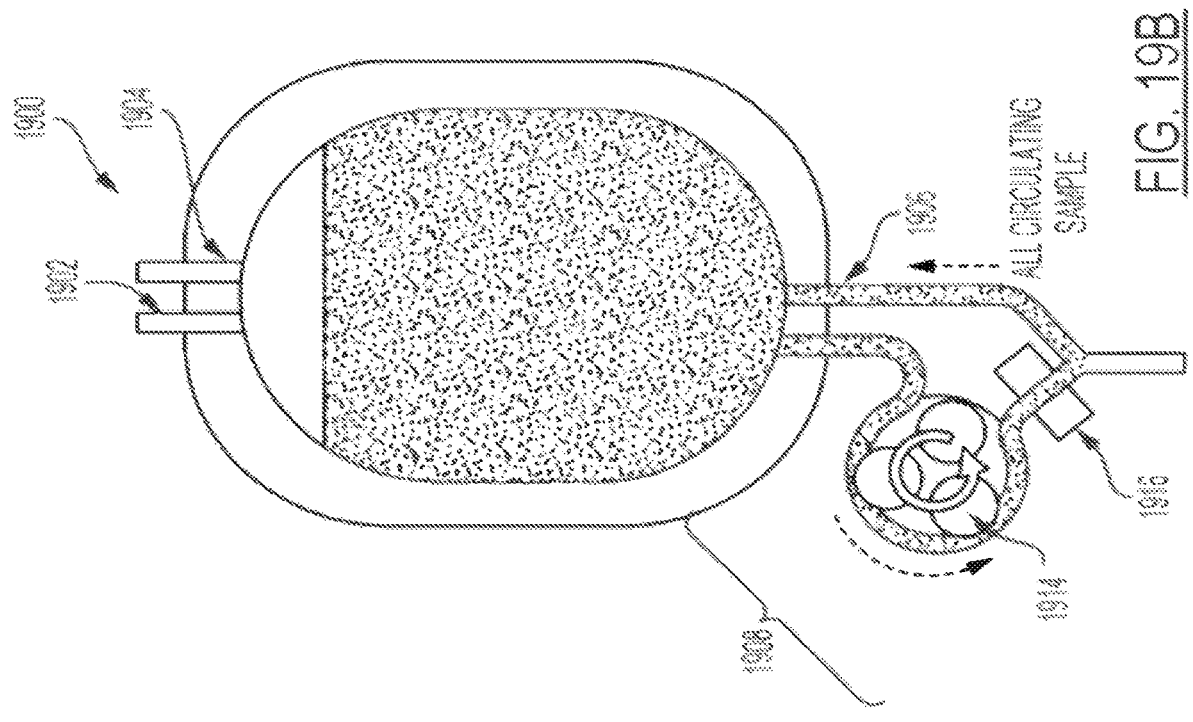
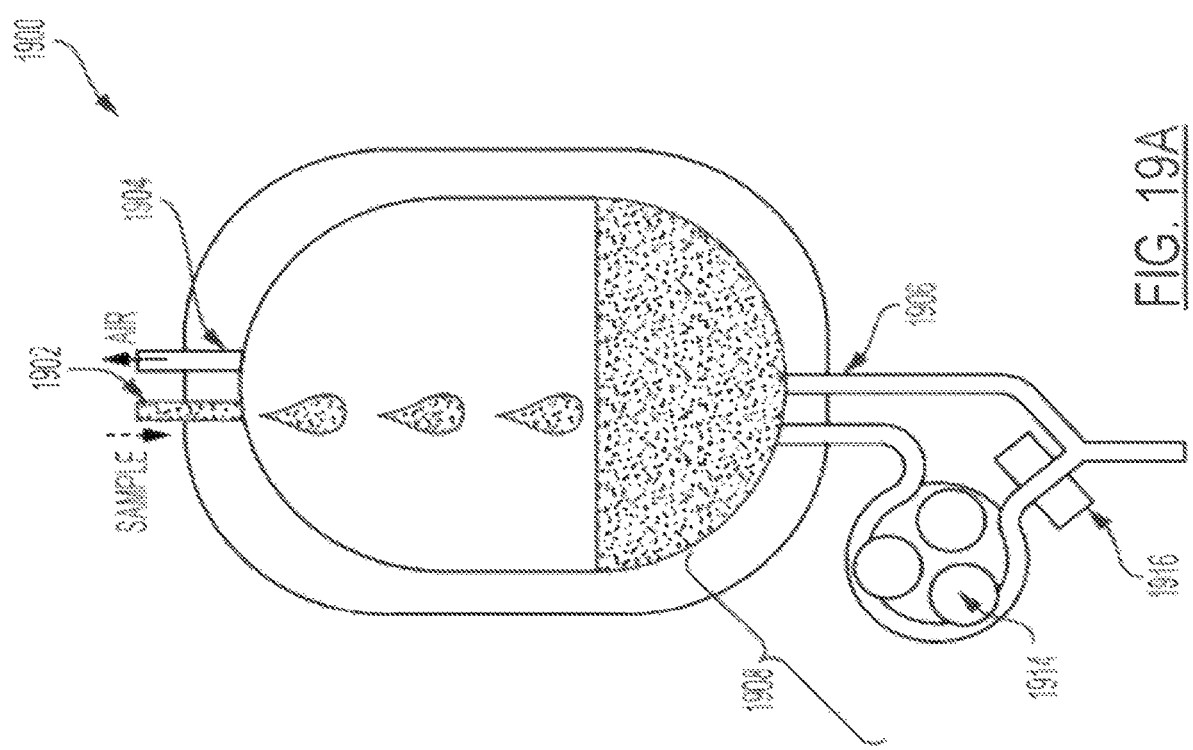

SYSTEM FOR DELIVERY OF A PAYLOAD INTO A CELL

CROSS REFERENCE TO RELATED APPLICATIONS

This application is a national phase filing under 35 U.S.C. § 371 of International Application No. PCT/US2018/066295, filed internationally on Dec. 18, 2018, which claims the benefit of U.S. Provisional Application No. 62/608,202, filed Dec. 20, 2017, the entire contents of which are hereby incorporated herein by reference.

FIELD

The present disclosure relates to techniques for delivery of a payloads into cells, and more specifically to tabletop systems for causing perturbations of cell membranes to allow passage of a payload through a cell membrane.

BACKGROUND

The controlled delivery of various materials into cells is important in the developing medical field of cell therapy. For example, various research and therapeutic applications may include the delivery of peptides, nucleic acids, proteins, small molecules, and nanomaterials through cell membranes and into cells. As discussed in WO2013059343, WO2015023982, PCT/US2015/058489, PCT/US2015/060689, and PCT/US2016/13113, constricting microfluidic channels may be used to deliver compounds and other payloads into cells. However, previous systems and methods for the delivery of materials into cells include numerous separate pieces of equipment to prepare the cells and the payload, to pass the cells through a constriction, and to process the cells following passage through the constriction. These numerous separate pieces of equipment may need to be operated by various different technicians, and the overall cell processing procedure may be slowed due to the time required to perform tasks by different persons and by different equipment. Additionally, operation of numerous different pieces of equipment by different operators leads to inconsistent results across different operators. Furthermore, various separate pieces of equipment may occupy scarce and expensive space and time in laboratory clean-rooms.

SUMMARY OF THE INVENTION

As explained above, known methods for intracellular payload delivery utilize many different types of laboratory equipment, many different operators performing spatially and temporally distributed tasks, and large amounts of space and time in laboratory clean-rooms. Accordingly, improved techniques for intracellular payload delivery are needed. In some embodiments, the disclosed systems, methods, and techniques for intracellular delivery that may be performed at a tabletop scale by a single operator at a single piece of laboratory equipment suitable for use inside a laboratory clean-room. The systems, methods, and techniques disclosed herein may improve the processing time, throughput rate, consistency, and efficiency of intracellular payload delivery processing on a clinical scale and in a clinical setting.

In some embodiments, a tabletop laboratory and/or clinical system is provided, whereby the tabletop laboratory and/or clinical device is configured to receive a cell suspension and a payload for delivery into the cells of the cell suspension and to force the cell suspension through a disposable constriction cartridge in order to cause perturbations in the membranes of the cells in the cell suspension. The system may be configured to automatically control the flow, temperature, agitation, and/or pressure of the cell suspension and/or its environment before, during, and after the system causing the cell suspension to flow through the restriction cartridge. In some embodiments, the system may be controllable by a single user operating a user interface to control the flow, temperature, agitation, pressure, pH, concentration, and/or other characteristics and properties of the cell suspension and/or its environment. In some embodiments, the system includes one or more disposable components configured for a one-time use, wherein the disposable components may be attached to the system by hand and without the use of tools such that the cell suspension may flow through one or more of the disposable components before, during, and/or after constriction of the cells.

In some embodiments, a first system, for delivering a payload to a cell, is provided, the system comprising: a platform supporting: a holder configured to hold a cell suspension input container containing a cell suspension comprising cells; a receiver configured to receive all or part of a disposable assembly, the disposable assembly comprising: a preparation vessel configured to be in fluid communication with the input container and to hold the cell suspension as it is prepared for passage through one or more cell-deforming constrictions; and a constriction cartridge configured to be in fluid communication with the preparation vessel, the constriction cartridge configured to house a component comprising the one or more cell-deforming constrictions, wherein the cell-deforming constrictions are configured to cause perturbations in a cell membrane of the cell to allow entry of a payload into the cell; and one or more processors configured to receive input from a user and to control one or more control modules, the one or more control modules configured to control one or more of a pressure, temperature, agitation, and flow of the cell suspension, wherein the one or more control modules comprises: a flow control module configured to cause the cell suspension to flow from the input container through the disposable assembly to a cell suspension output container such that the payload is delivered into the cell.

In some embodiments, a first disposable assembly, for use in a system for delivering a payload to a cell, is provided, the first disposable assembly comprising: a preparation vessel configured to hold cell suspension as it is prepared for passage through one or more cell-deforming constrictions; and a constriction cartridge configured to be in fluid communication with the preparation vessel, the constriction cartridge configured to house a component comprising the one or more cell-deforming constrictions, wherein the cell-deforming constrictions are configured to cause perturbations in a cell membrane that allow entry of a payload into the cell.

In some embodiments, a first method, for delivering a payload to a cell, is provided, the first method comprising: providing a cell in a cell suspension; passing the cell suspension into a preparation vessel at a tabletop system; while the cell suspension is in the preparation vessel, preparing the cell suspension including by causing pressure to be applied to the cell suspension; passing the prepared cell suspension from the preparation vessel through a constriction cartridge of the system, wherein the constriction cartridge is configured to house a component comprising a cell-deforming constriction that causes a perturbation in a membrane of the cell that allows entry of a payload into the cell.

In some embodiments, a second system, for delivering a payload through a cell membrane, is provided, the second system comprising: a preparation vessel configured to contain a cell suspension, wherein the suspension comprises cells; a constriction cartridge fluidly connected to the preparation vessel; a touch-screen display; one or more processors; and a memory configured to store instructions executable by the one or more processors to cause the system to: detect a contact on the display at a location corresponding to an icon for initiating a process for delivering a payload through membranes of cells in the cell suspension; and in accordance with detecting the contact: cause a temperature of the cell suspension inside the preparation vessel to be adjusted; cause pressure to be applied to the cell suspension inside the preparation vessel; and pass the cell suspension from the preparation vessel through a constriction in a component housed in the constriction cartridge, wherein the constriction is a cell-deforming constriction that causes perturbations in membrane of the cells in the cell suspension that allow entry of the payload into the cells.

In some embodiments, a third system, for delivering a payload to a cell, is provided, the third system comprising: a platform supporting: a holder configured to hold a cell suspension input container containing a cell suspension comprising cells; a receiver configured to receive a disposable assembly, the disposable assembly comprising: a preparation vessel configured to be in fluid communication with the input container and to hold the cell suspension as it is prepared for passage through one or more cell-deforming constrictions; and a constriction cartridge configured to be in fluid communication with the preparation vessel, the constriction cartridge configured to house a component comprising the one or more cell-deforming constrictions, wherein the cell-deforming constrictions are configured to cause perturbations in a cell membrane of the cell to allow entry of a payload into the cell; a cell suspension output container configured to be in fluid communication with the constriction cartridge; and one or more processors configured to receive input from a user and to control one or more control modules, the one or more control modules configured to control one or more of a pressure, temperature, agitation, and flow of the cell suspension, wherein the one or more control modules comprises: a flow control module configured to cause the cell suspension to flow from the input container through the disposable assembly to the output container such that the payload is delivered into the cell.

In some embodiments, a second disposable assembly, for use in a system for delivering a payload to a cell, is provided, the second disposable assembly comprising: a preparation vessel configured to hold cell suspension as it is prepared for passage through one or more cell-deforming constrictions; and a constriction cartridge configured to be in fluid communication with the preparation vessel, the constriction cartridge configured to house a component comprising the one or more cell-deforming constrictions, wherein the cell-deforming constrictions are configured to cause perturbations in a cell membrane that allow entry of a payload into the cell; and a cell suspension output container configured to be in fluid communication with the constriction cartridge.

In some embodiments, a second method, for delivering a payload to a cell, is provided, the second method comprising: providing a cell in a cell suspension; passing the cell suspension into a preparation vessel at a tabletop system; while the cell suspension is in the preparation vessel, preparing the cell suspension including by causing pressure to be applied to the cell suspension; passing the prepared cell suspension from the preparation vessel through a constriction cartridge of the system, wherein the constriction cartridge is configured to house a component comprising a cell-deforming constriction that causes a perturbation in a membrane of the cell that allows entry of a payload into the cell.

In some embodiments, a fourth system, for delivering a payload through a cell membrane, is provided, the fourth system comprising: a preparation vessel configured to contain a cell suspension, wherein the suspension comprises cells; a constriction cartridge fluidly connected to the preparation vessel; a touch-screen display; one or more processors; and a memory configured to store instructions executable by the one or more processors to cause the system to: detect a contact on the display at a location corresponding to an icon for initiating a process for delivering a payload through membranes of cells in the cell suspension; and in accordance with detecting the contact: cause a temperature of the cell suspension inside the preparation vessel to be adjusted; cause pressure to be applied to the cell suspension inside the preparation vessel; and pass the cell suspension from the preparation vessel through a constriction in a component housed in the constriction cartridge, wherein the constriction is a cell-deforming constriction that causes perturbations in membrane of the cells in the cell suspension that allow entry of the payload into the cells.

In some embodiments, any one or more of the features, characteristics, or elements discussed above with respect to any of the embodiments of the systems, the method, or the assembly may be incorporated into any of the embodiments of the other systems, the method, or the assembly mentioned above. In some embodiments, any one or more of the features, characteristics, or elements discussed elsewhere in this disclosure may be incorporated into any of the embodiments of the systems, the method, or the assembly mentioned above.

BRIEF DESCRIPTION OF THE DRAWINGS

FIG. 19A-19D illustrate a flexible bag for holding cell suspension fluid, during execution of four different functions of a tabletop system for delivering a payload to a cell, in accordance with some embodiments.

DETAILED DESCRIPTION OF THE INVENTION

Figure 1:
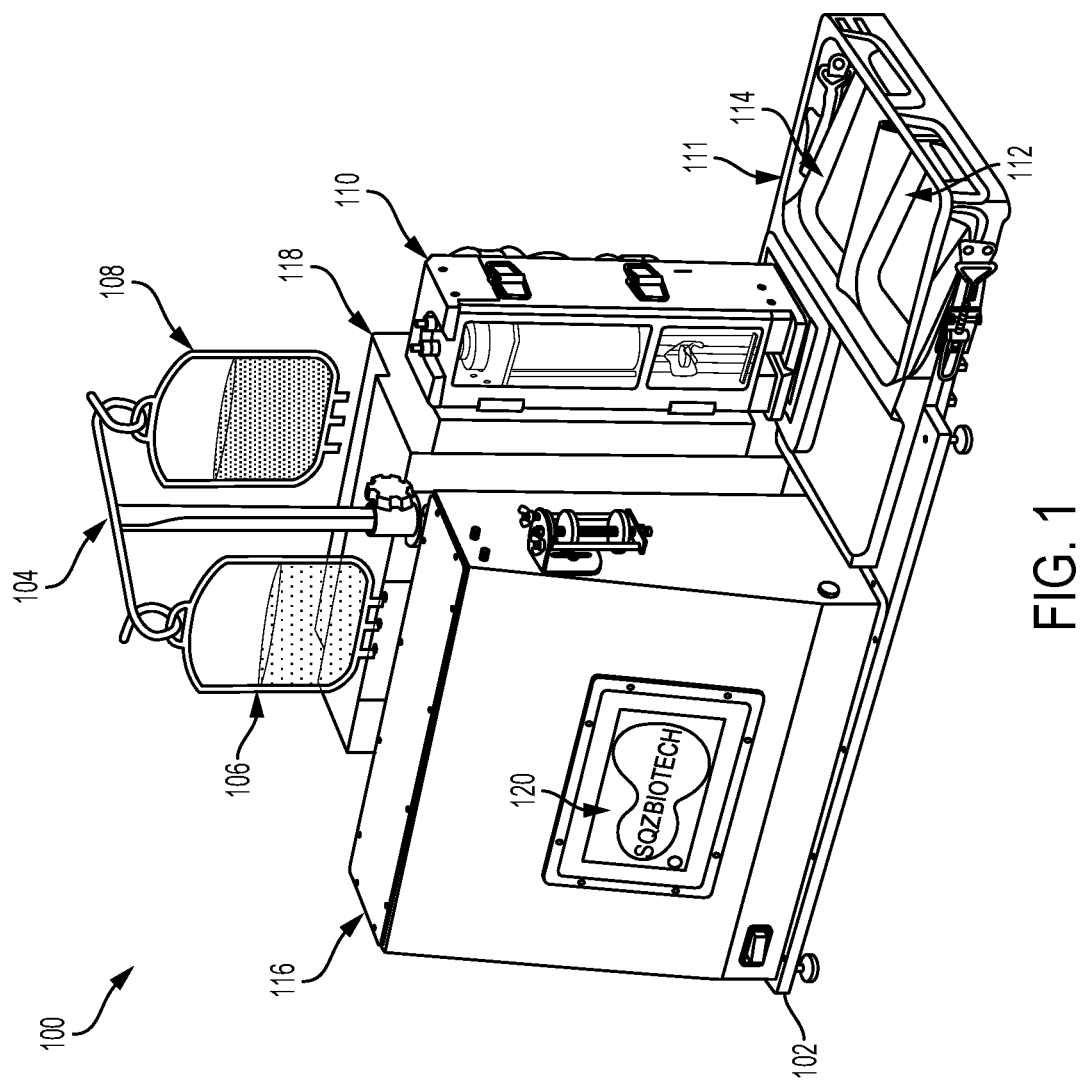
FIG. 1 illustrates a tabletop system for delivering a payload to a cell, in accordance with some embodiments.

Described below are exemplary embodiments of tabletop laboratory and/or clinical systems for partially or fully automated intracellular payload delivery, as well as associated devices, systems, methods, techniques, and user interfaces. Below, the description of FIGS. 1-11B primarily describe exemplary embodiments of tabletop systems and associated devices for intracellular payload delivery, wherein the systems and devices may be used in conjunction with the methods, techniques, and user interfaces described herein. After that, the description of FIGS. 12 and 13 primarily describes methods and techniques for cell processing and intracellular payload delivery, wherein the methods and techniques may be performed by or in conjunction with systems, methods, devices, and user interfaces described elsewhere herein. Next, the description of FIGS. 14A-14V primarily describes exemplary user interfaces for controlling systems and devices and for executing methods and techniques for intracellular payload delivery. Next, FIGS. 15-19D primarily describe further exemplary embodiments of tabletop laboratory and/or clinical systems and associated devices for intracellular payload delivery, including flexible bags usable therein, wherein the systems and devices may be used in conjunction with the methods, techniques, and user interfaces described herein. Finally, the description of FIG. 20 primarily describes a computing device that may be integrated into or used in conjunction with any of the systems or devices described herein.

The following description sets forth exemplary systems, methods, techniques, parameters, and the like. It should be recognized, however, that such description is not intended as a limitation on the scope of the present disclosure but is instead provided as a description of exemplary embodiments.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is further understood that the terms "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The term "about" as used herein refers to the usual error range for the respective value readily known to the skilled person in this technical field. Reference to "about" a value or parameter herein includes (and describes) embodiments that are directed to that value or parameter per se.

Although the description herein uses terms first, second, etc. to describe various elements, these elements should not be limited by the terms. These terms are only used to distinguish one element from another.

For any of the structural and functional characteristics described herein, methods of determining these characteristics are known in the art.

All references cited herein, including patent applications and publications, are incorporated by reference in their entirety.

Intracellular Payload Delivery Systems and Devices

As described below, the techniques, systems, and methods disclosed herein may provide for intracellular payload delivery that may be performed at a tabletop scale by a single operator at a single piece of laboratory equipment suitable for use inside a laboratory clean-room. Furthermore, the techniques, systems, and methods disclosed herein may provide for intracellular payload delivery systems having removable and/or disposable components, such as components that may be configured for one-time use, which may be able to be quickly and conveniently be attached to the overall system, by hand in a closed sterile environment and without the use of tools. As described below, disposable components of the systems described herein may be configured for use in a sterile environment and may nevertheless be robust enough to sustain the pressures used to force fluid to flow through the system. The systems, methods, and techniques disclosed herein may vastly improve the processing time, throughput rate, consistency, and efficiency of intracellular payload delivery processing. Below, FIGS. 1-20 provide a description of exemplary techniques, systems, and methods for intracellular payload deliver, in accordance with some embodiments.

FIG. 1 illustrates a tabletop system 100 for delivering a payload to a cell, in accordance with some embodiments. System 100 may be a tabletop system, such as a piece of laboratory equipment, configured to accept cellular suspension fluid and to process the cellular suspension fluid to deliver a payload to the cells of the cellular suspension. System 100 may, in some embodiments, be configured to be operated by a single user, two users, or more than two users, such as by being controlled by an electronic user interface presented via one or more buttons, keyboards, keypads, dials, knobs, and/or touch-screen interfaces.

In some embodiments, system 100 may include one or more computing devices configured to enable full or partial automated control of one or more components of system 100. As described below, system 100 may include one or more control modules, such as a pressure control module and a temperature control module, all of which may contain one or more computing devices. As used herein, the term control module may refer to one or more components of a system that together work to control one or more characteristics of the system and/or of fluid or other media controlled by the system, such as a pressure control module controlling pressure or a temperature control module controlling temperature. In some embodiments, a control module may comprise one or more physical components (e.g., sensors, control devices such as pumps or heating devices, etc.) and/or one or more electronic devices (e.g., computer processors, computer memory, etc.). In some embodiments, a control module may refer to a plurality of system components that may or may not be physically separated/segregated from other system components, and that may or may not be removable from the system. In some embodiments, all or part of a control module may be provided in a single housing with all or part of another control module. In some embodiments, a single system component (e.g., a processor, a sensor, a pump, a portion of tubing, etc.) may form a part of only one control module or of more than one control module. Computing devices as described and referenced herein may comprise one or more processors coupled to computer-readable storage media storing computer instructions that, when executed, may cause the one or more computing devices to execute all or part of the one or more of the methods described herein. In some embodiments, one or more of the computing devices described herein may be electronically/communicatively coupled with one another in order to send and receive electronic signals representing data, information, and/or instructions. In some embodiments, one or more of the computing devices described herein may be coupled to one or more electronic devices configured to send signals to the one or more computing devices (e.g., a sensor) and/or to receive instructions from the one or more computing devices (e.g., an electronically-controllable valve). Electronic communicative coupling of computing devices and associated electronic components may in some embodiments include wired electronic communication over wired networks or computer buses, and may in some embodiments include wireless electronic communication over wireless computer networks. The various systems described herein, including systems 100, 1000, 1100, 1500, and 1600, and the various associated electronic devices may all include one or more computing devices as described above. Thus, this disclosure may describe certain actions taken by a system or by a component of a system (e.g., generating data, detecting an input, controlling an electronic component) or device, and it may be understood by a person of skill in the art that these actions may be undertaken by one or more computing devices of the system or device. Where specific hardware or software is not specifically described for executing an action taken by any of the systems or devices described herein, a person of ordinary skill in the art may understand that this action may be executed by a computing device of the system or device.

In some embodiments, as described in further detail below, system 100 may be configured for use inside a sterile environment (e.g., a closed sterile environment) such as a laboratory clean-room. For example, system 100 may be configured such that all of its components (including disposable components as described below) may be sterile (e.g., pre-sterilized) and/or sterilizable so as not to contaminate a sterile environment. Additionally, one or more components of system 100 may be made from materials that are acceptable for use in sterile environments, such as stainless steel (e.g., marine-grade stainless, 316-grade stainless, 316L-grade stainless, etc.). Additionally, system 100 may include one or more particulate filters to ensure compliance with requirements for operation in a sterile environment.

Furthermore, system 100 may be made compact in order to not occupy scarce and expensive space inside a sterile environment, which are often small spaces that are in high demand. For example, in some embodiments, system 100 may be less than about 3 feet, less than about 2 feet, or less than about 1 foot in length. In some embodiments, system 100 may be greater than about 2 feet, greater than about 1 foot, or greater than about 6 inches in length. In some embodiments, the system may be less than about 2 feet, less than about 1 foot, or less than about 8 inches in depth. In some embodiments, the system may be greater than about 1 foot, greater than about 8 inches, or greater than about 4 inches in depth. In some embodiments, the system may be less than about 3 feet, less than about 2 feet, or less than about 1 foot in height. In some embodiments, the system may be greater than about 2 feet, greater than about 1 foot, or greater than about 6 inches in height. In some embodiments, system 100 may be less than about 60 pounds, less than about 40 pounds, less than about 20, or less than about 10 pounds in weight. In some embodiments, system 100 may be greater than about 40 pounds, greater than about 20, greater than about 10 pounds, or greater than about 5 pounds in weight.

As shown in FIG. 1, system 100 may be a tabletop system comprising several components mounted atop platform 102. Platform 102 may be a rigid base configured to support the weight of the other components of system 100 and configured such that the other components of system 100 may be securely mounted in a fixed position to platform 102. Platform 102 may be configured to sit on a tabletop, laboratory bench, movable cart, or the like. In some embodiments, platform 102 may be configured to sit on the floor. By virtue of being constructed such that various components of system 100 are all supported by platform 102, system 100 may be made compact, lightweight, and portable; for example, system 100 may be lightweight and compact enough so that platform 102 may be moved or carried from one laboratory space to another and the other components will move along with platform 102, such that system 100 may be fully functional immediately following platform 102 being moved from one location to another.

System 100 may further comprise hooks 104, which may be configured to suspend one or more bags. In the example shown in FIG. 1, hooks 104 are configured to suspend cell suspension input bag 106 and buffer input bag 108. Bags 106 and 108 may be flexible bags configured to contain liquid to be passed through and processed by system 100. Bags 106 and 108 may be configured to be suspended from hooks 104 and fluidly connected to a flow path of system 100. The flow path, which will be described in greater detail throughout this specification, may be a flow path through which cell suspension is configured to flow in order to process the cell suspension to prepare cells of the cell suspension for payload delivery, and in some embodiments to cause payload delivery. In some embodiments, the flow path may originate at bags 106 and 108 and lead through one or more pipes or flexible tubes into a preparation vessel housed in preparation vessel housing 110.

System 100 may further comprise preparation vessel housing 110, which may be any structure or component configured to house a preparation vessel. As described in greater detail below, a preparation vessel may be any vessel configured to house cell suspension fluid as it is prepared for passage through a constriction component, wherein the constriction component defines a part of the flow path configured to cause perturbations in membranes of the cells of the cell suspension fluid in order to facilitate entry of the payload into the cells through the membranes. For example, the preparation vessel may be configured to hold cell suspension while the suspension is cooled (or heated), agitated, as the cell suspension has air pressure applied to it, and/or as the cell suspension is otherwise manipulated or controlled to be forced through a constriction component. Preparation vessel housing 110 may in some embodiments be a rigid housing such as the rectangular housing shown in FIG. 1, wherein it may have an inlet opening for the flow path to enter the housing and an outlet opening for the flow path to exit the housing. In the example of FIG. 1, the inlet opening is at the top of housing 110 and the outlet opening is at the bottom of housing 110, such that the flow path into, through, and out of the preparation vessel may be gravitationally assisted.

In some embodiments, housing 110 may be configured such that it can be opened and closed in order that the preparation vessel inside the housing (and/or other components inside the housing) may be inserted, adjusted, and/or removed. In the example of FIG. 1, housing 110 has a hinged door on the front that may be opened and closed. In some embodiments, housing 110 may be configured to contact the preparation vessel (e.g., when the preparation vessel inserted into the housing) in such a way as to facilitate one or more preparation processes. For example, housing 110 may be configured to contact the preparation vessel to facilitate transfer of heat between the preparation vessel and housing 110, and/or housing 110 may be configured to contact the preparation vessel to facilitate agitation of the cell suspension by shaking housing 110 and transferring motion to the preparation vessel.

In some embodiments, in addition to the preparation vessel, housing 110 may be further configured to house one of more additional components, such as components defining additional portions of the flow path. For example, as discussed in greater detail below, housing 110 may additionally be configured to house an entire disposable assembly including a preparation vessel and a constriction cartridge, wherein the constriction cartridge may be configured to house a component such as a microfluidic chip or filter that defines a part of the flow path configured to cause cell membrane perturbations. In some embodiments, the preparation vessel may additionally be configured to house and/or be connected to one or more sensors, such as a temperature sensor (e.g., thermistor), flow-sensor (e.g., bubble sensor, flow-rate sensor), pressure sensor, weight sensor, accelerometer, $CO_2$ sensor, pH sensor, osmometer, conductivity sensor, impedance detector, light-based detector, and/or any one or more sensors configured to measure cell concentration, membrane disruption, and/or other properties of cells or of cell suspension. Any of the sensors recited herein may be connected to the preparation vessel in some embodiments, may be connected to other system components in some embodiments, and/or may be configured to come into direct contact with fluid flowing through the system (e.g., to be inside the preparation vessel or otherwise inside a flow path of the system).

In some embodiments, in addition to the temperature sensor(s) discussed below with reference to sensor assembly 900, housing 110 may include one or more integrated temperature sensors configured to detect a temperature of part of the housing and to send data to the system in accordance with the temperatures detected. In some embodiments, the one or more integrated temperature sensors may be configured for use in determining a temperature of the housing, preparation vessel, and/or cell suspension inside the preparation vessel, as discussed further below.

System 100 may further comprise output bag tray 111, which may be a tray or other holder component configured to hold, house, or otherwise support one or more bags or other containers configured to receive fluid after it has flowed through the flow path of system 100. In the example of FIG. 1, output bag tray 111 is configured to hold cell suspension output bag 112 and buffer output bag 114. Output bags 112 and 114 may share one or more properties in common with input bags 106 and 108, except that output bags 112 and 114 may be configured to start an intracellular payload delivery process empty, and to end the process full. That is, output bags 112 and 114 may be filled with cell suspension and buffer fluid respectively after the fluids flow through the flow path of system 100. In some embodiments, output bags 112 and 114 may be fluidly connected to the flow path through the outlet opening at the bottom of preparation vessel housing 110 such that fluid may flow through the preparation vessel and the constriction cartridge and then out of housing 110 and into one of bags 112 and 114. In some embodiments, such as the example shown in FIG. 1, output bag tray 111 may be disposed on platform 102 in such a way that the output bags that it supports are located at, near, and/or below the bottom of preparation vessel housing 110, such that flow of fluid from housing 110 toward tray 111 may be gravitationally assisted.

System 100 may further comprise pressure control module 116, which may comprise any structure, housing, or component of system 100 configured to house pressure control hardware and/or software, as will be described in greater detail below. In the example of FIG. 1, pressure control module 116 comprises a rigid structure mounted atop platform 102 and housing touch-screen display 120, which may be configured to display a graphical user interface for controlling one or more operations of system 100. In some embodiments pressure control module 116 may be electrically and mechanically coupled to one or more other components of system 100 such that processors located in pressure control module 116 may send and receive signals to other electronic components of system 100 and such that pressure control hardware (e.g., pumps, filters, etc.) may be fluidly connected to send and receive one or more pressurized fluids (e.g., sterile gas, air, etc.) to other components of system 100.

System 100 may further comprise temperature control module 118, which may comprise any structure, housing, or component of system 100 configured to house temperature control hardware and/or software, as will be described in greater detail below. In the example of FIG. 1, temperature control module 118 comprises a rigid structure mounted atop platform 102. In some embodiments, temperature control module 118 may be electrically and mechanically coupled to one or more other components of system 100 such that processors located in temperature control module 118 may send and receive signals to other electronic components of system 100 and such that temperature control hardware (e.g., heating/cooling elements) may be physically connected to transfer heat to or from other components of system 100.

Figure 2:
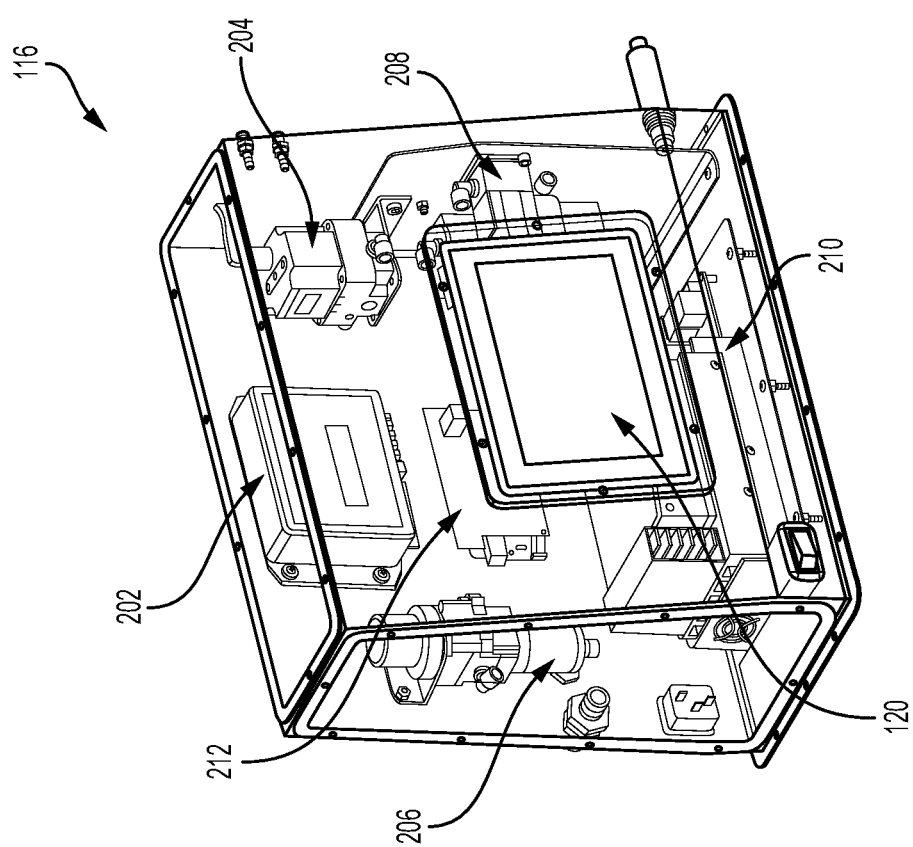
FIG. 2 illustrates a partially transparent view of a pressure control module of a tabletop system for delivering a payload to a cell, in accordance with some embodiments.

FIG. 2 illustrates a partially transparent view of pressure control module 116 of tabletop system 100 for delivering a payload to a cell, in accordance with some embodiments. In some embodiments, pressure control module 116 is the same pressure control module 116 as discussed above with reference to FIG. 1. In some embodiments, pressure control module 116 may receive a flow of pressurized gas from an external source, such as a pressurized canister, regulate the pressure of the flow, direct the flow through one or more filters, and direct the flow into a preparation vessel of the system such that the pressurized gas may force the flow of the cell suspension through a constriction cartridge of the system. In some embodiments, pressure control module 116 may be configured to be attachable to one or more filter assemblies, which may be removable and/or replaceable and may, in some embodiments, be configured to be external to a body/housing of the pressure control module and attachable by one or more inlets or outlets.

As shown in FIG. 2, pressure control module 116 may comprise touch-screen display 120 mounted on an exterior surface of a housing of module 116. Touch-screen display 120 may be electronically connected to other electronic components of system 100 in order to send and receive control and display signals. Touch-screen display 120 may be configured to display a graphical user interface for controlling one or more operations of system 100. In some embodiments, rather than a touch-screen display, pressure control module 116 may comprise a non-touch-screen display, one or more buttons, one or more knobs, one or more sliders, one or more keyboards, one or more additional touch-screen or non-touch-screen displays, and/or any other component configured to accept inputs from a user in order to control operations of system 100. In some embodiments, touch-screen display 120 (or other user controls such as those as described above) may be located on another component of system 100 and may be similarly electronically coupled to components of system 100.

Pressure control module 116 may further comprise various internal components as described below. Pressure control module 116 may comprise electro-pneumatic regulator assembly 204, which may be configured to use one or more valves (e.g., push valves, vent valves, solenoid valves 208, etc.) to control the flow of gas and to maintain an output gas pressure at a pressure that is input or otherwise indicated by a user of by the system. Electro-pneumatic regulator 204 may be controlled by one or more integrated or external processors. Electro-pneumatic regulator 204 may be configured to intake gas from a sterile gas source or from the environment (e.g., to intake air) and to output pressurized gas. Electro-pneumatic regulator 204 may be configured to be fluidly connected to an output path for the pressurized gas, which may be fluidly connected to an opening in the preparation vessel as discussed above. In some embodiments, the opening in the preparation vessel configured to accept the flow of pressurized gas may be located atop or near the top of the preparation vessel. In this way, the electro-pneumatic regulator 204 may be configured to deliver pressurized gas to the preparation vessel above the cell suspension fluid (or buffer fluid) such that the pressurized gas applies pressure downward upon the fluid.

Pressure control module 116 may further comprise PID controller 202, which may be any proportional-integral-derivative controller configured to regulate pressure. PID controller 202 may be electronically coupled with electro-pneumatic regulator 204 and may be configured to receive signals indicating a current pressure and to deliver control signals to electro-pneumatic regulator 204, based on calculations made on the basis of the current pressure, wherein the control signals are configured to maintain the desired pressure caused by electro-pneumatic regulator 204 in an optimal manner (e.g., without using excess power and without causing pressure corrections to unnecessarily over-shoot the desired pressure).

Pressure control module 116 may further comprise air filter (e.g., a gas filter) and regulator assembly 206, which may comprise a pressure regulator and an air filter. In some embodiments, air filter and regulator assembly 206 may be configured to be attached to a source of pressurized gas, such a pressurized canister containing a gas (e.g., air, nitrogen, etc.). A pressure regulator of assembly 206 may be fluidly connected to the source of pressurized gas and may be configured to reduce the input pressure to a desired pressure, such as a pressure that may be set by a user or by the system. The pressure regulator may be further fluidly connected to an air filter of assembly 206, which may be any filter configured to remove contaminants from the gas flowing from the regulator. Accordingly, gas may flow from a pressurized gas source through the regulator, then through the air filter, and then finally toward and into electropneumatic regulator 204 as described above.

Pressure control module 116 may further comprise electronic board(s) 212, which may be configured to be electronically connected to any one or more electronic components of module 116 (or other electronic components of system 100) and to send and receive signals to and from the components.

Figure 3A:
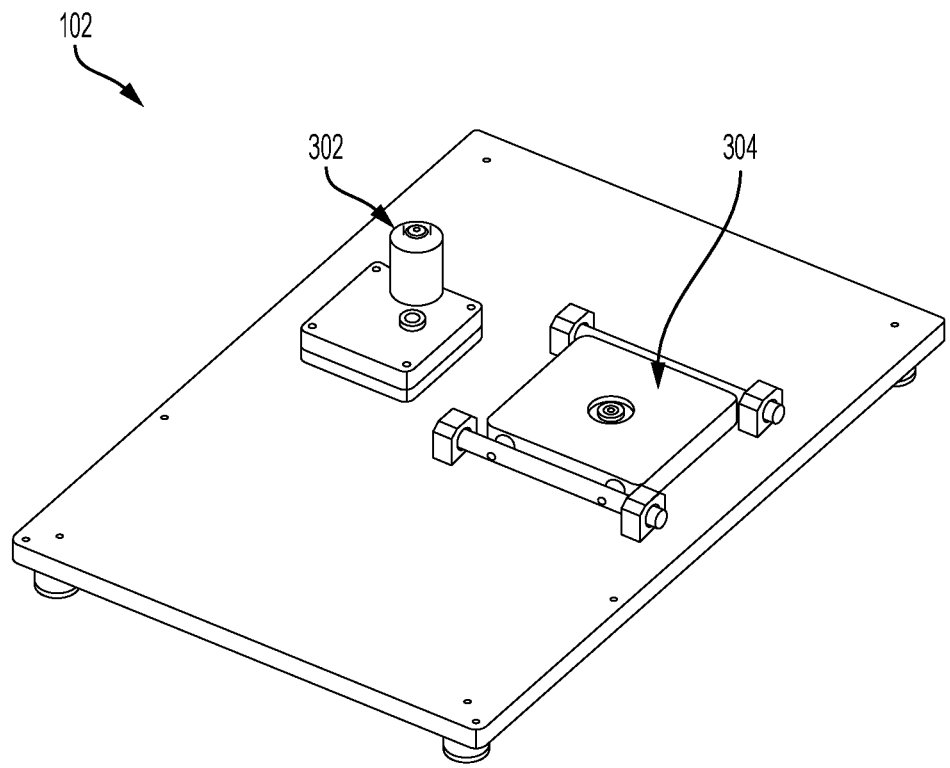
FIG. 3A illustrates a platform of a tabletop system for delivering a payload to a cell, in accordance with some embodiments.
Figure 3B:
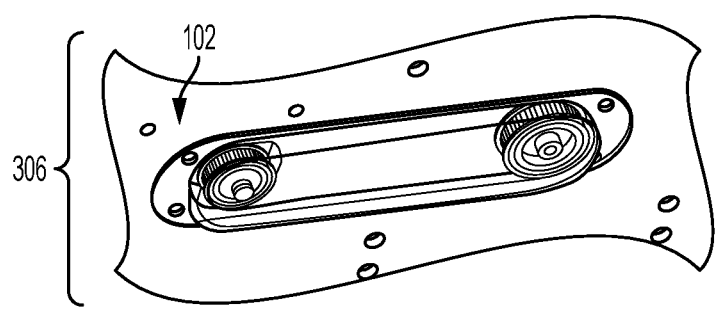
FIG. 3B illustrates a detail view of a platform of a tabletop system for delivering a payload to a cell, in accordance with some embodiments.

Pressure control module 116 may further comprise power supply and relay assembly 210, which may be configured to supply electrical power to one or more components of pressure control module 116 (such as any of the components discussed above) and/or to any other electrically-powered component FIGS. 3A and 3B illustrate platform 102 of a tabletop system 100 for delivering a payload to a cell, in accordance with some embodiments. In some embodiments, platform 102 is the same platform 102 as discussed above with reference to FIG. 1.

As shown in FIG. 3A, platform 102 may have a motor 302 and a shaker plate 304 mounted on a top surface of the platform. Motor 302 may be configured to drive a belt, as shown as part of belt drive 306 in FIG. 3B, to cause movement of shaker plate 304. In some embodiments, motor 302 may be connected to shaker plate 304 by one or more belts, drive axles, or other mechanical components. In the embodiments of FIGS. 3A and 3B, motor 302 and shaker plate 304 are connected by belt drive 306 located on the underside of platform 102; however, in some embodiments motor 302 and shaker plate 304 may be connected by one or more components disposed above, beside, and/or inside platform 102.

In some embodiments, shaker plate 304 may be configured to support a preparation vessel housing, such as preparation vessel housing 110 as discussed above with respect to FIG. 1. Movement of shaker plate 304 (e.g., vibration, circular, back-and-forth, and/or up-and-down movement) may cause agitation of a cell suspension located inside a preparation vessel housed in a preparation vessel housing when the housing is mounted atop shaker plate 304. Accordingly, movement of shaker plate 304 may be configured to cause agitation of a cell suspension, such as to prevent cells from falling out of suspension, as discussed further below.

In some embodiments, a drive-speed of motor 302 may be controllable by one or more input devices of system 100, such as a physical input knob and/or a touch-screen user interface.

Figure 4:
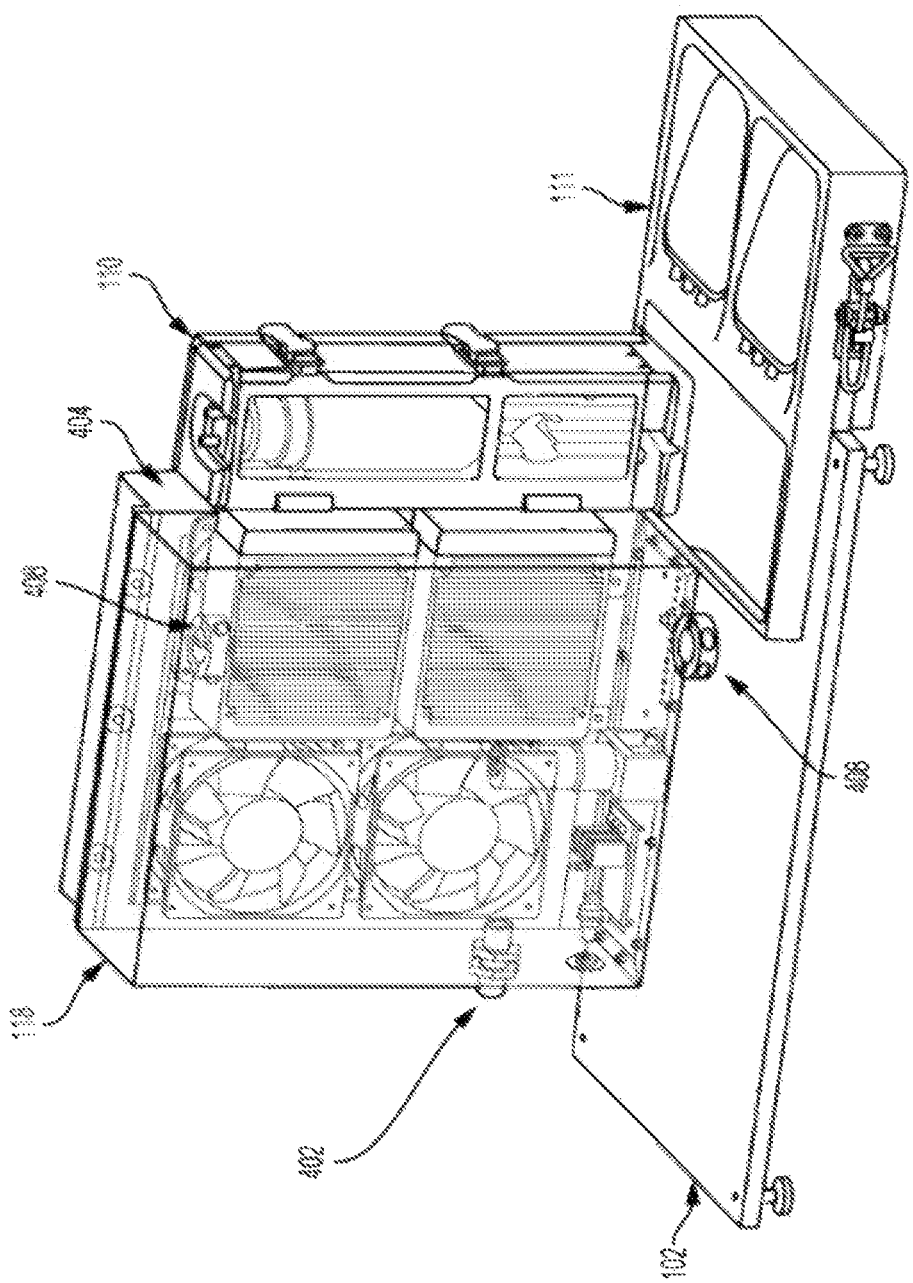
FIG. 4 illustrates a partially transparent view of a temperature control module of a tabletop system for delivering a payload to a cell, in accordance with some embodiments.

FIG. 4 illustrates a partially transparent view of temperature control module 118 of tabletop system 100 for delivering a payload to a cell, in accordance with some embodiments. In some embodiments, temperature control module 118 is the same temperature control module 118 as discussed above with reference to FIG. 1.

As shown in FIG. 4, temperature control module 118 may be mounted atop platform 102 and beside preparation vessel housing 110 and output bag tray 111. In some embodiments, temperature control module 118 may be mounted such that it is nearby and/or in physical contact with preparation vessel housing 110 such that it may be easily electrically and/or physically connected to preparation vessel housing 110, as discussed above.

Temperature control module 118 may further comprise various internal components as described below. In some embodiments, temperature control module 118 may include one or more components configured to heat and/or cool preparation vessel housing 110 or a component thereof. For example, temperature control module 118 may include one or more forced-air heaters, one or more forced-air coolers, one or more thermoelectric cooling devices (e.g., Peltier coolers), one or more resistive heating devices, one or more liquid heating devices, one or more liquid cooling devices, or the like. In some embodiments, the heating and/or cooling components may be in electronic, electrical, and/or physical contact with preparation vessel housing 110. In some embodiments, one or more Peltier coolers may be used to cool a cooling liquid that may be circulated to come into contact with and draw heat away from all or part of the housing 110, such as a stainless steel jacket forming an interior wall of housing 110 and configured to come into contact with preparation vessel 600.

Temperature control module 118 may comprise vent gas input 402. In some embodiments, vent gas input 402 may be configured to allow venting of excess gas from one or more regulators of the system (such as any of the regulators discussed below) such that the gas may vent inside the system, thereby preventing pressure build up in the system and limiting vibrations to prevent particulate contamination in the sterile environment.

Temperature control module 118 may further comprise filter 404, which may be any filter configured such that exhaust generated by the system may be passed through it before being released into the environment outside system 100. For example, filter 404 may be a high-efficiency particulate absorbing (HEPA) filter such that system 100 may be suitable for use in a sterile environment when exhaust is passed through the HEPA filter before being released into the sterile environment.

FIG. 4 also shows mounts 408 for hooks 104. Mounts 408 may be mounted on platform 102, a housing of pressure control module 116, and/or a housing of temperature control module 118. Mounts 408 may be configured such that they may be loosened and/or tightened to adjust a position of hooks 104.

Figure 5B:
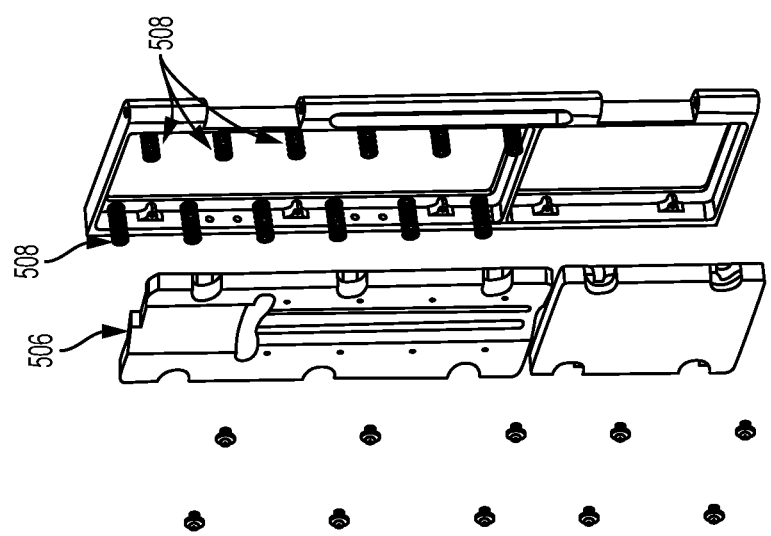
FIG. 5B illustrates an exploded view of a door of a preparation vessel housing of a tabletop system for delivering a payload to a cell, in accordance with some embodiments.
Figure 5A:
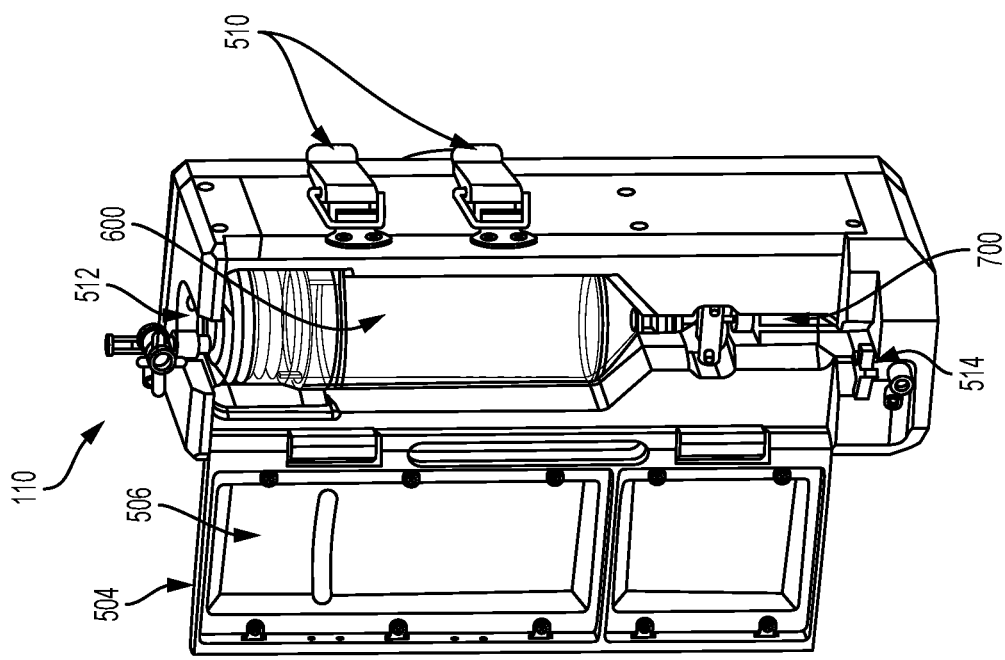
FIG. 5A illustrates a preparation vessel housing of a tabletop system for delivering a payload to a cell, in accordance with some embodiments.

FIGS. 5A and 5B illustrate preparation vessel housing 110 of tabletop system 100 for delivering a payload to a cell, in accordance with some embodiments. In some embodiments, preparation vessel housing 110 is the same preparation vessel housing 110 as discussed above with reference to FIG. 1.

As shown in FIG. 5A, preparation vessel housing 110 may be a rigid housing with a rectangular exterior configured to house preparation vessel 600 and constriction cartridge 700, both of which will be described in greater detail below. As described above, preparation vessel 600 and constriction cartridge 700 may each define a part of the flow path for cell suspension, and may be connected to one other by tubing. As shown in FIG. 5A, preparation vessel housing 110 may comprise inlet opening 512 and outlet opening 514; the openings may be positioned and configured such that piping or tubing defining the cell suspension flow path of system 100 may pass through the openings. In some embodiments, inlet opening 512 is located at or near the top of housing 110 while outlet opening 514 is located at or near the bottom of housing 110, such that flow of fluid through a flow path that travels from inlet opening 512 to outlet opening 514 may be gravitationally assisted. In the example shown, inlet opening 512 is configured to allow buffer fluid or cell suspension fluid to flow in through a tube, and also to allow air for pressurization of preparation vessel 600 to flow in through another tube. In the example shown, outlet opening 514 is configured to allow buffer fluid or cell suspension fluid to flow out through a tube after passing through preparation vessel 600 and constriction cartridge 700.

As shown in FIG. 5A, the openings inside preparation vessel housing 110 may be shaped such that preparation vessel 600 and constriction cartridge 700 fit securely into a predefined location in housing 110 and are in contact with the interior walls of housing 110.

Preparation vessel housing 110 may further comprise door 504, as shown in FIG. 5B, which may allow access to the interior of housing 110. In the example of FIGS. 5A and 5B, door 504 is hinged along one side and is closable by latches 510 along the other side. As shown in FIG. 5B, window 506 of door 504 may be acted upon by springs 508. Springs 508 may in some embodiments attach window 506 to door 504, and may be arranged such that they are compressed when door 504 is closed and latched with preparation vessel 600 inside housing 110. For example, when door 504 is closed, window 506 may be pressed against preparation vessel 600, causing springs 508 to be compressed. The spring force of springs 508 may therefore cause window 506 to press firmly against preparation vessel 600 and to ensure that preparation vessel 600 is held firmly in place against the interior walls of housing 110.

In some embodiments, one or more interior walls of housing 110 may be configured to contact an exterior surface of preparation vessel 600, such that the walls may transfer heat to and/or from preparation vessel 600. In some embodiments, an interior wall of housing 110 may be made of metal such as stainless steel in order to facilitate fast and efficient transfer of heat from the walls to preparation vessel 600. In some embodiments, the spring force of springs 508 may cause window 506 to press firmly against preparation vessel 600 and to ensure that preparation vessel 600 is in contact with the interior walls of housing 110, thereby facilitating optimal heat transfer.

Figure 6B:
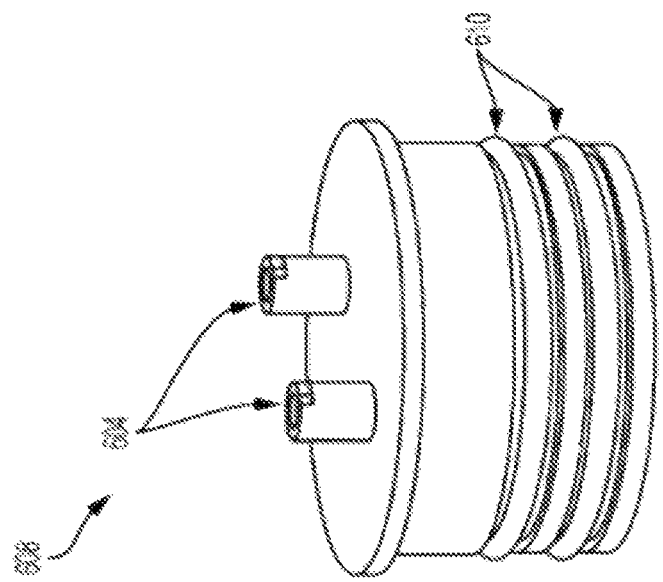
FIG. 6B illustrates a cap of a preparation vessel of a tabletop system for delivering a payload to a cell, in accordance with some embodiments.
Figure 6A:
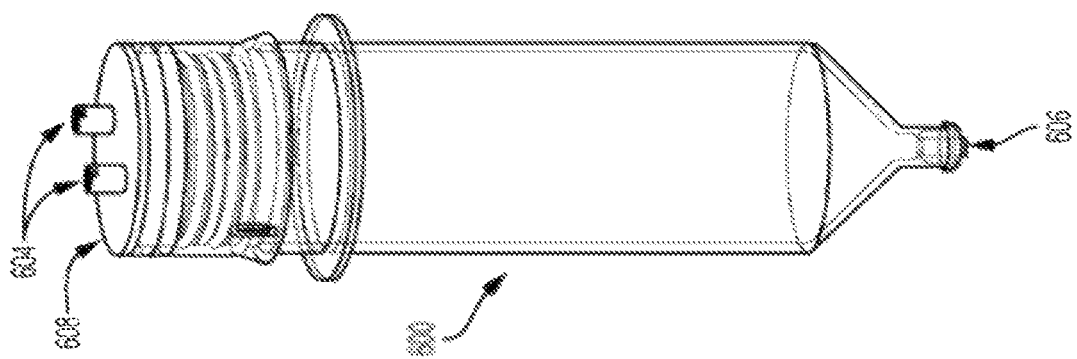
FIG. 6A illustrates a preparation vessel of a tabletop system for delivering a payload to a cell, in accordance with some embodiments.

FIGS. 6A and 6B illustrate preparation vessel 600 of tabletop system 100 for delivering a payload to a cell, in accordance with some embodiments. In some embodiments, preparation vessel 600 is the same preparation vessel 600 as discussed above with reference to FIGS. 5A, and 5B, and/or the same preparation vessel as discussed above with respect to FIG. 1. Preparation vessel 600 may be any vessel or container configured to house fluid passing through the system, including cell suspension fluid, buffer fluid, and/or pressurized gas. Namely, preparation vessel 600 may be configured to hold cell suspension fluid while the cell suspension is prepared for passage through a constriction cartridge, such as constriction cartridge 700. In some embodiments, preparing a cell suspension for passage through a constriction cartridge may include cooling the suspension, heating the suspension, agitating the suspension, and/or applying pressure to the suspension.

As shown in FIG. 6A, preparation vessel 600 may in some embodiments be a rigid, syringe-shaped vessel. In some embodiments, preparation vessel 600 may be made of plastic or other suitable inert and sterilizable materials. In some embodiments, preparation vessel 600 may have a volume of about 25 mL, about 50 mL, about 100 mL, about 250 mL, about 500 mL, about 1 L, about 2 L, about 5 L, or about 10 L. In some embodiments, preparation vessel 600 may have a volume greater than about 10 mL, 25 mL, about 50 mL, about 100 mL, about 250 mL, about 500 mL, about 1 L, about 2 L, about 5 L, or about 10 L. In some embodiments, preparation vessel 600 may have a volume less than about 25 mL, about 50 mL, about 100 mL, about 250 mL, about 500 mL, about 1 L, about 2 L, about 5 L, about 10 L, or about 20 L. In some embodiments, preparation vessel 600 may be formed from a modified 250-mL medical-grade syringe.

In some embodiments, preparation vessel 600 may have a tapered shape at its bottom portion in order to gravitationally direct the flow of fluid in the vessel toward vessel outlet 606, which may be disposed at or near a bottom end of preparation vessel 600. In some embodiments, vessel inlets 604 may be disposed at or near a top end of preparation vessel 600. In the embodiment shown in FIG. 6A, vessel inlets 604 are openings formed in vessel cap 608, which is a removable cap configured to seal a top opening of vessel 600 and to be held in place by one or more o-rings 610, which may be medical-grade o-rings. In some embodiments, vessel 600 may be provided without a removable cap, or a removable cap or other lid or door may be held in place by a mechanism other than o-rings, such as by threads, clamps, adhesive, or the like.

In some embodiments, one or more of openings 604 and 606 may be configured to be fluidly connected to tubing, piping, or other system components that may define a flow path for cell suspension fluid, gas, or both. In some embodiments, openings 604 and/or 606 may include threads, Luer taper connector, Luer lock connectors, Luer slip connectors, slip tip connectors, or other connector mechanisms to allow connection to other components.

In some embodiments, preparation vessel 600 may be configured to be able to have a gas inside the preparation vessel pressurized up to at least an operating pressure of system 100. In some embodiments, an operating pressure of system 100 may be an air-pressure to which a gas in preparation vessel 600 is pressurized in order to force cell suspension fluid from preparation vessel 600 out of vessel outlet 606 and through constriction cartridge 700. In some embodiments, an operating pressure of system 100 may be about 20 psi, about 30 psi, about 50 psi, about 70 psi, about 90 psi, about 110 psi, or about 130 psi. In some embodiments, an operating pressure may be greater than 10 psi, 20 psi, 50 psi, 70 psi, 90 psi, 110 psi, or 130 psi. In some embodiments, an operating pressure may be less than 20 psi, 50 psi, 70 psi, 90 psi, 110 psi, 130 psi, or 150 psi. Preparation vessel 600 may be constructed and configured such that its caps, openings, valves, and other components may remain intact under the operational pressure.

Figure 7A:
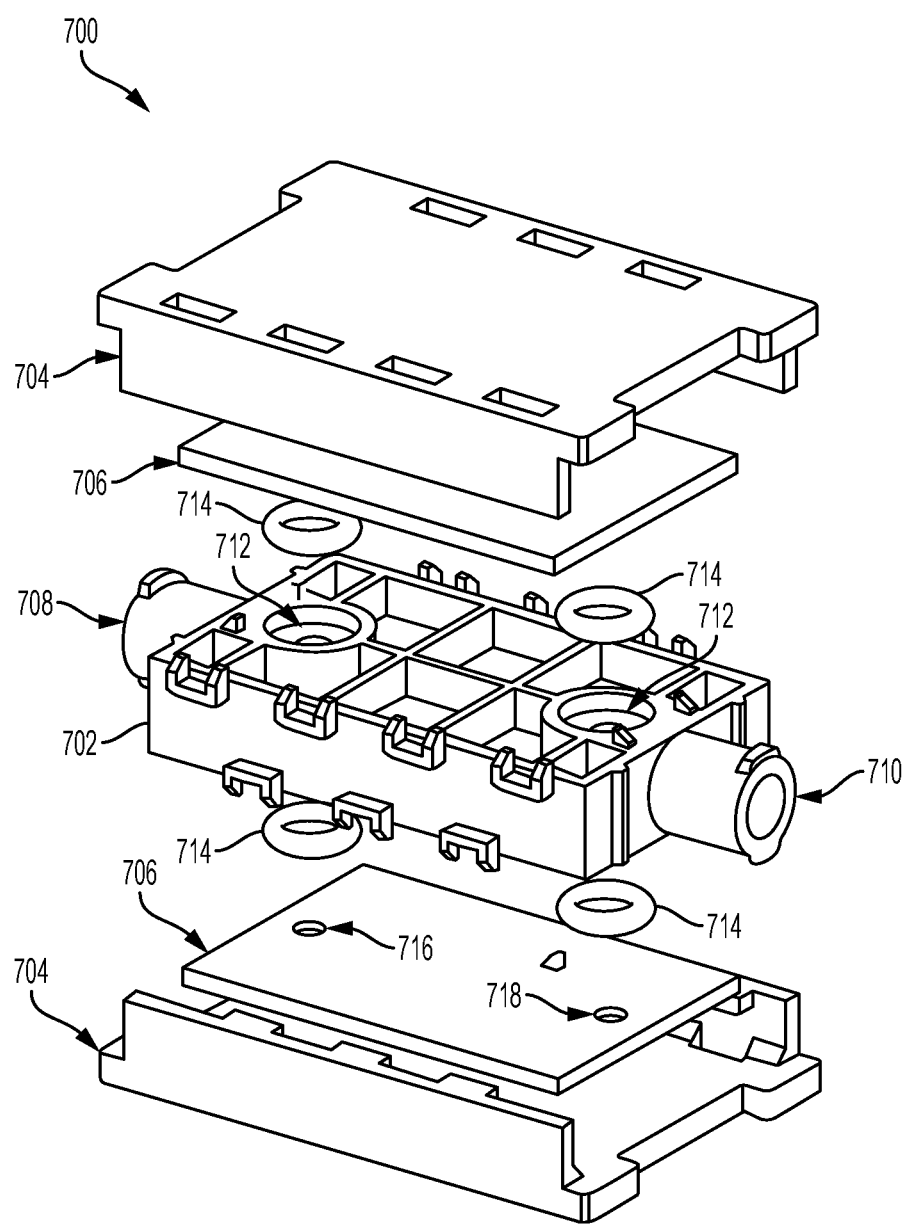
FIG. 7A illustrates an exploded view of a constriction cartridge of a tabletop system for delivering a payload to a cell, the constriction cartridge configured to house two chips, in accordance with some embodiments.
Figure 7B:
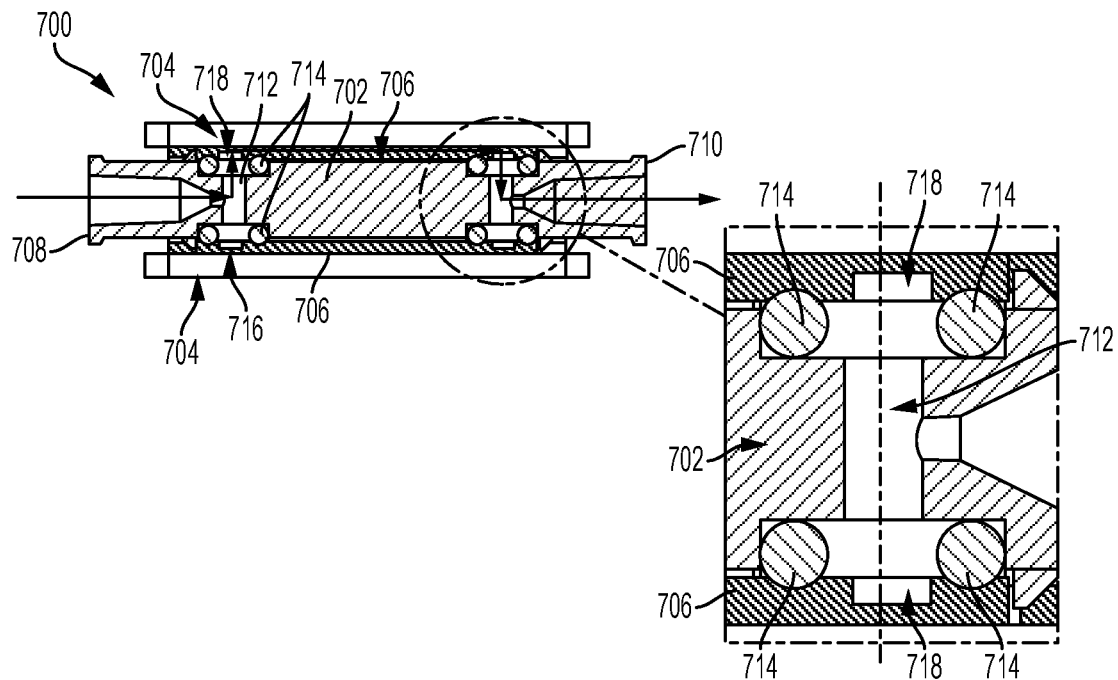
FIG. 7B illustrates a side cross-sectional view and detail-view highlight of a constriction cartridge of a tabletop system for delivering a payload to a cell, the constriction cartridge configured to house two chips, in accordance with some embodiments.
Figure 7C:
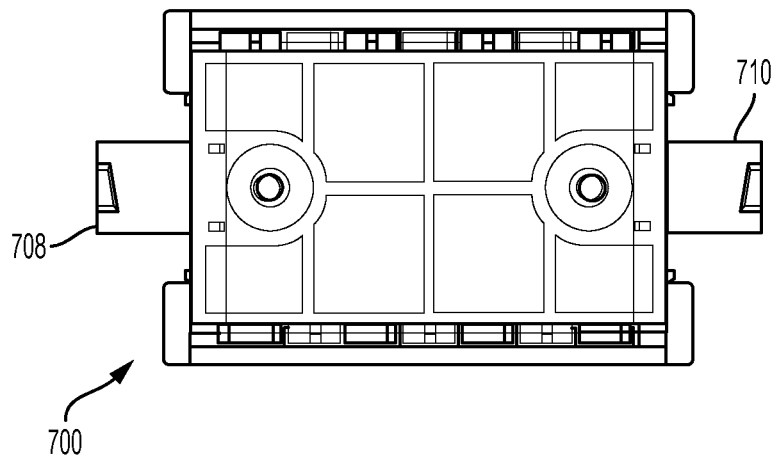
FIG. 7C a partially transparent overhead view of constriction cartridge of a tabletop system for delivering a payload to a cell, the constriction cartridge configured to house two chips, in accordance with some embodiments.

FIGS. 7A-7C illustrate various views of constriction cartridge 700 of tabletop system 100 for delivering a payload to a cell, the constriction cartridge configured to house two chips, in accordance with some embodiments. In some embodiments, constriction cartridge 700 is the same constriction cartridge 700 as discussed above with reference to FIGS. 1, 5A, and 5B. FIG. 7A illustrates an exploded view of a constriction cartridge of a tabletop system for delivering a payload to a cell, the constriction cartridge configured to house two chips, in accordance with some embodiments. FIG. 7B illustrates a side cross-sectional view and detail-view highlight of a constriction cartridge of a tabletop system for delivering a payload to a cell, the constriction cartridge configured to house two chips, in accordance with some embodiments. FIG. 7C a partially transparent overhead view of constriction cartridge of a tabletop system for delivering a payload to a cell, the constriction cartridge configured to house two chips, in accordance with some embodiments.

In some embodiments, constriction cartridge 700 may be any structure configured to contain or to house a constricting component, such as a constricting filter (containing one or more constricting microfluidic pores) or a constricting microfluidic chip (containing one or more constricting microfluidic channels). (Constricting filters in accordance with some embodiments are disclosed in application number WO/2017/041050A1, which is hereby incorporated by reference in its entirety.) It should be noted that, in some embodiments, a constricting microfluidic channel or a constricting microfluidic pore may simply be referred to as a "constriction" or a "cell-deforming constriction." A constricting component may be any component having a channel, passage, or other opening (e.g., a constriction) having a smaller diameter than a cell of the cell suspension, such that forcing the cell through the opening under pressure causes a perturbation in the membrane of the cell as the cell is constricted by the opening. In some embodiments, constriction cartridge 700 may include integrated constricting filters or microfluidic channels configured to constrict cells, while in some embodiments constriction cartridge 700 may be configured to house distinct components that themselves include constricting filters or constricting microfluidic channels. In either case, constriction cartridge 700 may define part of the flow path of system 100 such that the cell suspension may flow from preparation vessel 600 toward and into constriction cartridge 700, and such that the cell suspension may then flow through and out of constriction cartridge 700 and toward and into output bags 112 or 114 (or other suitable downstream flow path components).

In the example of FIGS. 7A-7C, constriction cartridge 700 comprises constriction cartridge inlet 708 and constriction cartridge outlet 710 disposed on cartridge body 702 and defining a beginning and end of the flow path for cell suspension and buffer fluid flowing through constriction cartridge 700. In some embodiments, constriction cartridge inlet 708 and constriction cartridge outlet 710 may include any one or more connection mechanisms discussed above with respect to inlets and outlets of preparation vessel 600, such as threaded connection mechanisms and/or Luer-type connection mechanisms. Between constriction cartridge inlet 708 and constriction cartridge outlet 710, the flow path of system 100 may diverge into two or more parallel portions as fluid travels through constriction cartridge 700, and may then re-converge before flowing out of constriction cartridge 700. In some embodiments, rather than defining multiple parallel flow paths through separate constriction components, constriction cartridge 700 may instead cause fluid to flow in series through multiple constriction components, one after the other. In some embodiments, constriction cartridge 700 may be configured to be able to receive a blank placeholder component in place of a functional constriction component, wherein the blank placeholder component may not contain any channels or pores, or may otherwise be configured to disallow flow through the portion of constriction cartridge 700 housing the placeholder component. By using a blank placeholder component, constriction cartridge 700 may cause flow of fluid through only one constriction component at a time, such that the system need not be used with two constriction components at all times.

In the embodiment shown in FIGS. 7A-7C, constriction cartridge 700 is configured to cause cell suspension (and buffer fluid) to flow into and through constriction components 706, which may be a constricting microfluidic chip having a plurality of constricting microfluidic channels or a constricting filter having a plurality of constricting openings or pores. In either event, constriction components 706 may have a respective constriction component inlet 716 for fluid to flow into the component and a respective constriction component outlet 718 for fluid to flow out of the component.

Both the constriction component inlet 716 and the constriction component outlet 718 may be positioned so as to align with one of o-ring fluid connections 712, which may be a portion of cartridge body 702 configured to house an o-ring 714 and to force the flow of fluid through the o-ring to and/or from a constriction component 706. O-ring 714 may create a seal such that fluid may flow through connection 712 and travel between body 702 and constriction component 706 without leaking out from the flow path defined by the o-ring. In some embodiments, other sealing options aside from or in addition to o-rings may be used to create a seal for a fluid connection between a constriction cartridge and a constriction component; for example, overmolding, chemical bonding, and/or mechanical interlocks may be used.

As shown in the detail view of FIG. 7B, the flow path inside cartridge body 702 may diverge into multiple path portions flowing toward o-ring fluid connectors and may re-converge following multiple path portions flowing from o-ring fluid connectors. In the example of FIG. 7B, the flow path diverges from one path into two portions at a t-shaped junction to cause fluid to flow from cartridge inlet 708 into both constriction components 706; and two portions converge into one path at a t-shaped junction to cause fluid to flow from both constriction components 706 toward cartridge outlet 710.

Thus, fluid such as buffer fluid or cell suspension may flow into constriction cartridge 700 via constriction cartridge inlet 708, and may thereafter flow toward and through the upstream pair of o-ring fluid connections 712. The fluid may flow through the upstream pair of o-ring fluid connections 712 and into each constriction component inlet 716. From constriction component inlets 716, the fluid may flow through one or more channels or flow paths defined by constriction components 706, and may then flow out of constriction components 706 at each of constriction component outlets 718. From constriction component outlets 718, the fluid may flow through the downstream pair of o-ring fluid connections and may reconverge to flow toward and out of constriction cartridge outlet 710, thereby flowing out of constriction cartridge 700. Thus, in short, fluid such as buffer fluid or cell suspension may flow into constriction cartridge 700 and may be passed through one or more constriction components before flowing out of constriction cartridge 700.

As shown in FIGS. 7A-7C, constriction cartridge 700 may include removable covers 704, which may be elements configured to be placed atop constriction components 706 and to press constriction components 706 toward cartridge body 702. In some embodiments, removable covers 704 may be configured to apply inward force to constriction components 706 to press them toward cartridge body 702 by way of one or more springs or other compressible components, such as rubber o-rings. In some embodiments, removable covers 704 may be configured to press flush against a surface of one of constriction components 706. In some embodiments, removable cover 704 may serve to ensure that constriction components 706 do not delaminate a layer under the pressure of fluid being forced through them; by holding down the top of a constriction component 706 under force, the constriction component 706 may be prevented from delaminating. In some embodiments, the sliding connection mechanism shown in FIGS. 7A-7C may offer superior durability under pressure to other mechanisms that may be used to hand-assembled constriction cartridges, such attaching a cover by threaded components. In some embodiments, in addition to or alternately to one or more removable covers, a constriction cartridge may be configured to securely house a constriction component without use of removable covers.

In some embodiments, removable covers 704 may be configured to be removable by a user, such as by a hinge mechanism, clasp mechanism, sliding mechanism, threading mechanism, locking mechanism, or other attachment and detachment mechanism. In the example shown in FIG. 7A, removable covers 704 may be slid laterally to attach and detach from cartridge body 702, such that constriction components 706 and o-rings 714 may be adjusted and/or replaced. As shown in FIG. 7A, interlocking teeth elements on removable covers 704 and body 702 may be configured to slide together to hold removable covers 704 in place.

FIGS. 8A-8D illustrate various views of constriction cartridge 800 of tabletop system 100 for delivering a payload to a cell, the constriction cartridge configured to house four chips, in accordance with some embodiments. In some embodiments, constriction cartridge 800 may share some or all characteristics in common with constriction cartridge 700 as discussed above with reference to FIGS. 1, 5A, 5B, and/or 7A-7C, except that constriction cartridge may be configured to hold four constriction components rather than two constriction components.

Generally speaking, a constriction cartridge of system 100 may be configured to hold any number of constriction components for use in parallel (or, alternately, in series) by configuring the shape of the body of the cartridge (and removable cover) to support the desired number of constriction components. For example, a two-constriction-component cartridge may have a planar body as shown in FIGS. 7A-7C, a three-constriction-component cartridge may have a triangular body, a four-constriction-component cartridge may have a rectangular body as shown in FIGS. 8A-8D, and so on. A cartridge body having any given number of faces and configured to hold the given number of constriction components may still have a single inlet and a single outlet, but rather than a t-shaped junction where the flow path diverges into two path portions (and a corresponding t-shaped junction where two path portions converge into one), the constriction cartridge body may instead have a junction where the flow path diverges into the given number of path portions, with one path portion proceeding toward each of the faces of the body.

In the example of FIGS. 8A-8D, constriction cartridge 800 has body 802 and removable cover 804, which may share any one or more characteristics in common with body 702 and removable covers 704, respectively, as described above with respect to FIGS. 7A-7C. As shown, body 802 may have inlet 808 and outlet 810, which may share any one or more characteristics in common with inlet 708 and outlet 710, respectively, as described above with respect to FIGS. 7A-7C.

As shown, body 802 may have four sides configured each configured to support a constriction component 806, which may share any one or more characteristics in common with constriction component 706, as described above with respect to FIGS. 7A-7C. Removable cover 804 may, in some embodiments, be configured to be removable from body 802 by sliding upward or downward as shown in FIG. 8C. Unlike removable cover 704 in FIGS. 7A-7C, removable cover 804 may in some embodiments have no teeth for attaching to a constriction cartridge body, as removable cover 804 may be configured to fully encircle a constriction cartridge body as shown, thereby preventing lateral movement once it is slid into place.

Figure 8A:
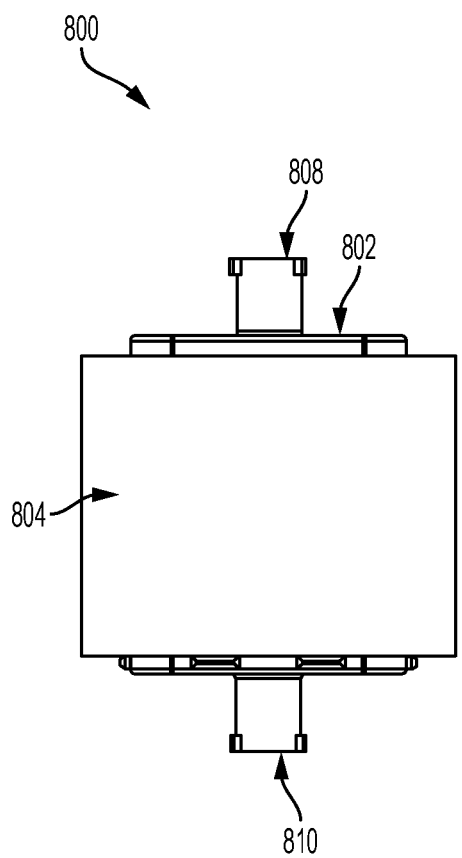
FIG. 8A illustrates a first view of a constriction cartridge of a tabletop system for delivering a payload to a cell, the constriction cartridge configured to house four chips, in accordance with some embodiments.
Figure 8B:
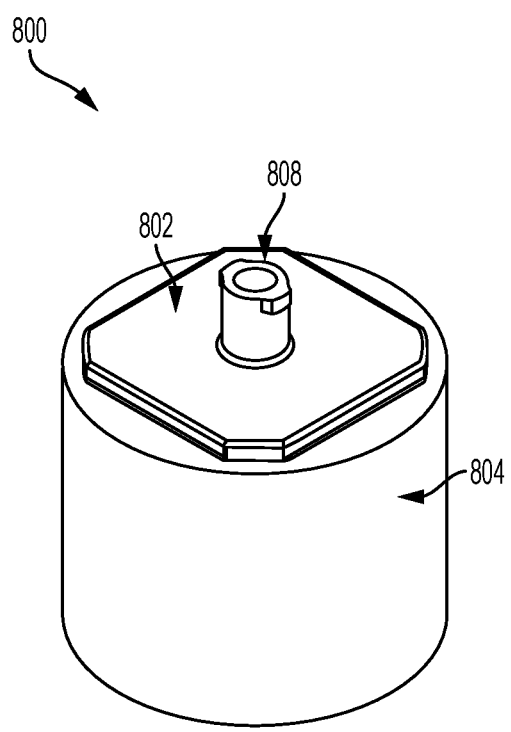
FIG. 8B illustrates a second view of a constriction cartridge of a tabletop system for delivering a payload to a cell, the constriction cartridge configured to house four chips, in accordance with some embodiments.
Figure 8D:
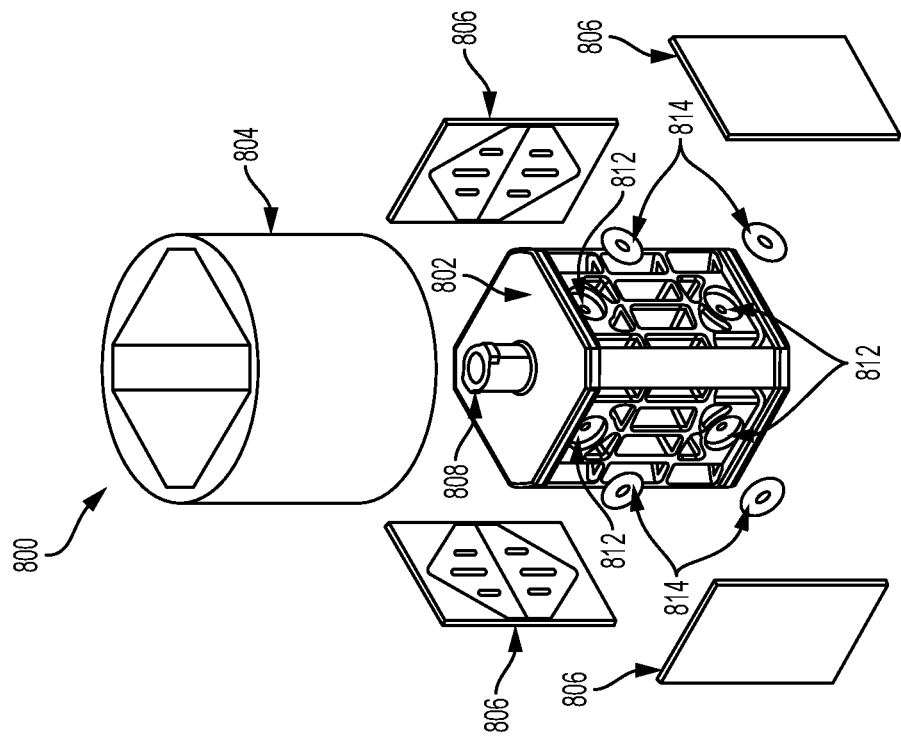
FIG. 8D illustrates a second partially exploded view of a constriction cartridge of a tabletop system for delivering a payload to a cell, the constriction cartridge configured to house four chips, in accordance with some embodiments.
Figure 8C:
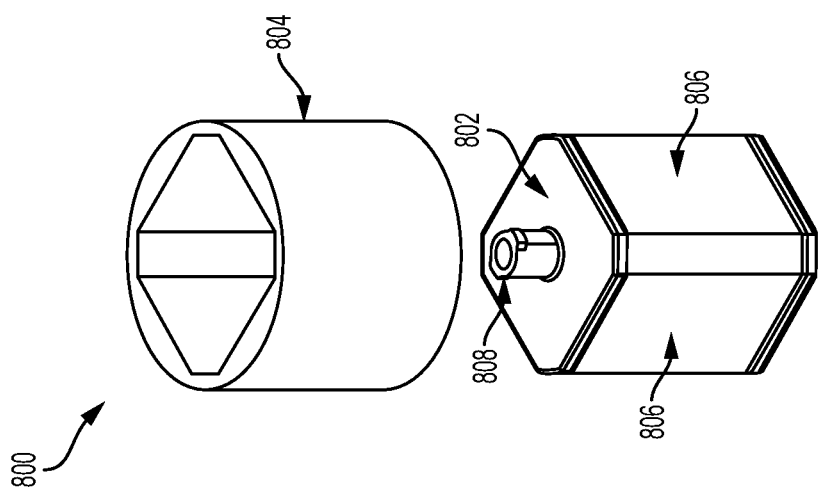
FIG. 8C illustrates a first partially exploded view of a constriction cartridge of a tabletop system for delivering a payload to a cell, the constriction cartridge configured to house four chips, in accordance with some embodiments.

As shown in FIG. 8D, constriction cartridge 800 may further comprise o-ring fluid connections 812 disposed in body 802 along with o-rings 814, which may share any one or more characteristics in common with o-ring fluid connections 712 and o-rings 714, respectively, as described above with respect to FIGS. 7A-7C. As described above, in some embodiments, o-ring fluid connections 812 may be fluidly connected to the flow path defined by inlet 808 and outlet 810 and may be configured to direct the flow of fluid (e.g., cell suspension and/or buffer fluid) in and/or out of constriction components 806.

While the example of FIGS. 8A-8D shown herein contemplates constriction components arranged on different outward-facing faces of constriction cartridge 800, different arrangements for cartridges containing two or more constriction components may be used in some embodiments. For example, in some embodiments, a constriction cartridge may comprise three or more slots for constriction components to be inserted such that the constriction components are arranged in a layered, stacked arrangement (e.g., similar to the arrangement of the constriction components 706 in constriction cartridge 700), and the cartridge may be configured to direct flow into and through each of the stacked components in parallel.

FIGS. 9A-9D illustrate sensor assembly 900 of tabletop system 100 for delivering a payload to a cell, in accordance with some embodiments. In some embodiments, sensor assembly 900 may be configured to send electronic signals to one or more electronic components of system 100 as discussed above with respect to FIG. 1. In some embodiments, sensor assembly 900 may include one or more sensors configured to measure one or more properties of a component of system 100 or of a substance contained in system 100, and to send data to electronic components of system 100 regarding the measurements taken. In some embodiments, sensor assembly 900 may contain one or more sensors configured to measure one or more properties; for example, sensor assembly may comprise a temperature sensor, a presence sensor, a flow sensor, and/or a pressure sensor.

Namely, sensor assembly 900 may be configured, in some embodiments, to take one or more measurements regarding the state of the cell suspension as it is passed through system 100 and to send signals to electronic components of system 100 such that the system may monitor the state of the cell suspension (and optionally control the state of the cell suspension in accordance therewith). In some embodiments, sensor assembly 900 may be configured to measure and/or monitor a temperature of a cell suspension (or a temperature of a container holding the cell suspension), such as while the cell suspension is in the preparation vessel and is being heated or cooled by the system. In some embodiments, sensor assembly 900 may be configured to measure and/or monitor pressure being applied to the cell suspension, such as the pressure of a gas inside the preparation vessel as the cell suspension is sitting inside the preparation vessel and/or flowing through the flow path downstream of the preparation vessel. In some embodiments, sensor assembly 900 may be configured to monitor a flow path of the cell suspension to determine whether the cell suspension is present in the flow path, such as by using an optical presence sensor to determine whether the cell suspension is flowing through a tube in order to determine whether the cell suspension is done flowing through the constriction cartridge.

Figure 9A:
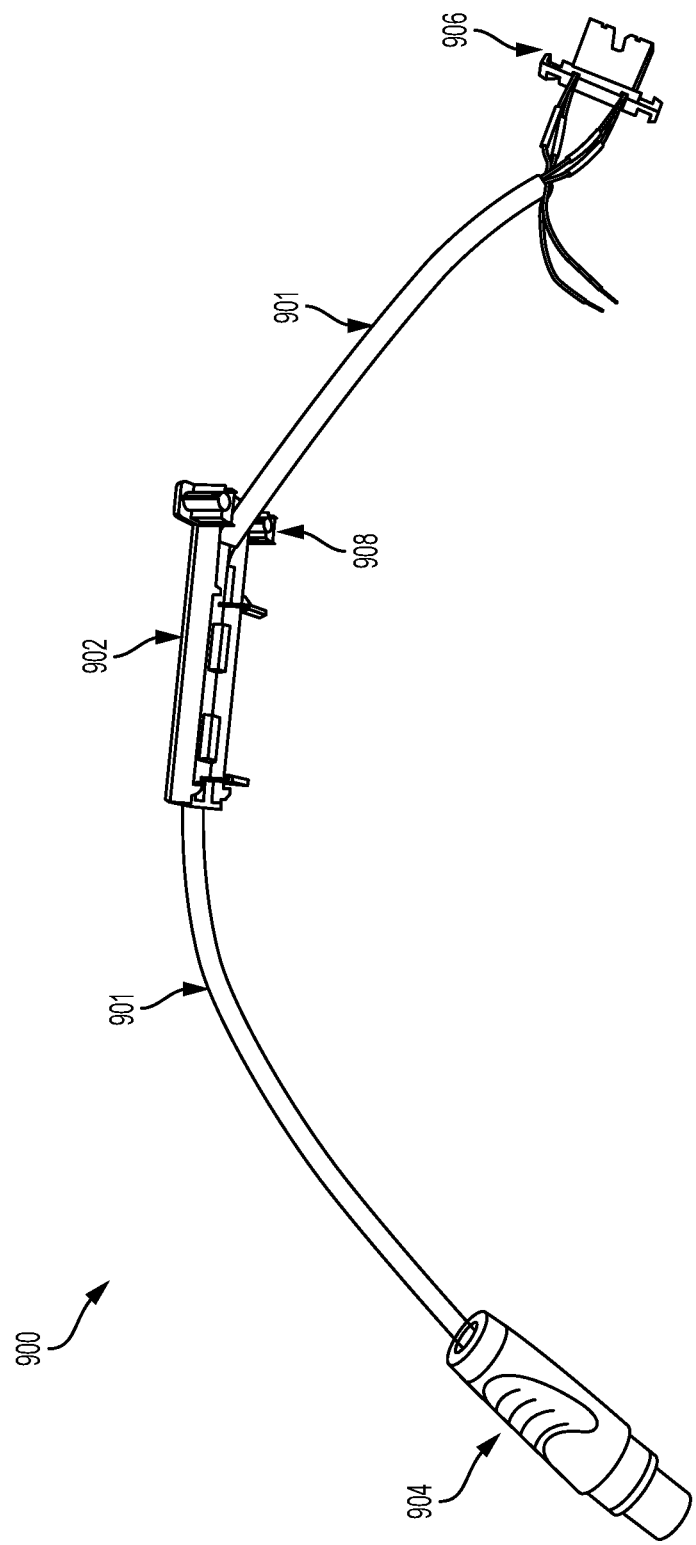
FIG. 9A illustrates a partially assembled sensor assembly of a tabletop system for delivering a payload to a cell, in accordance with some embodiments.
Figure 9B:
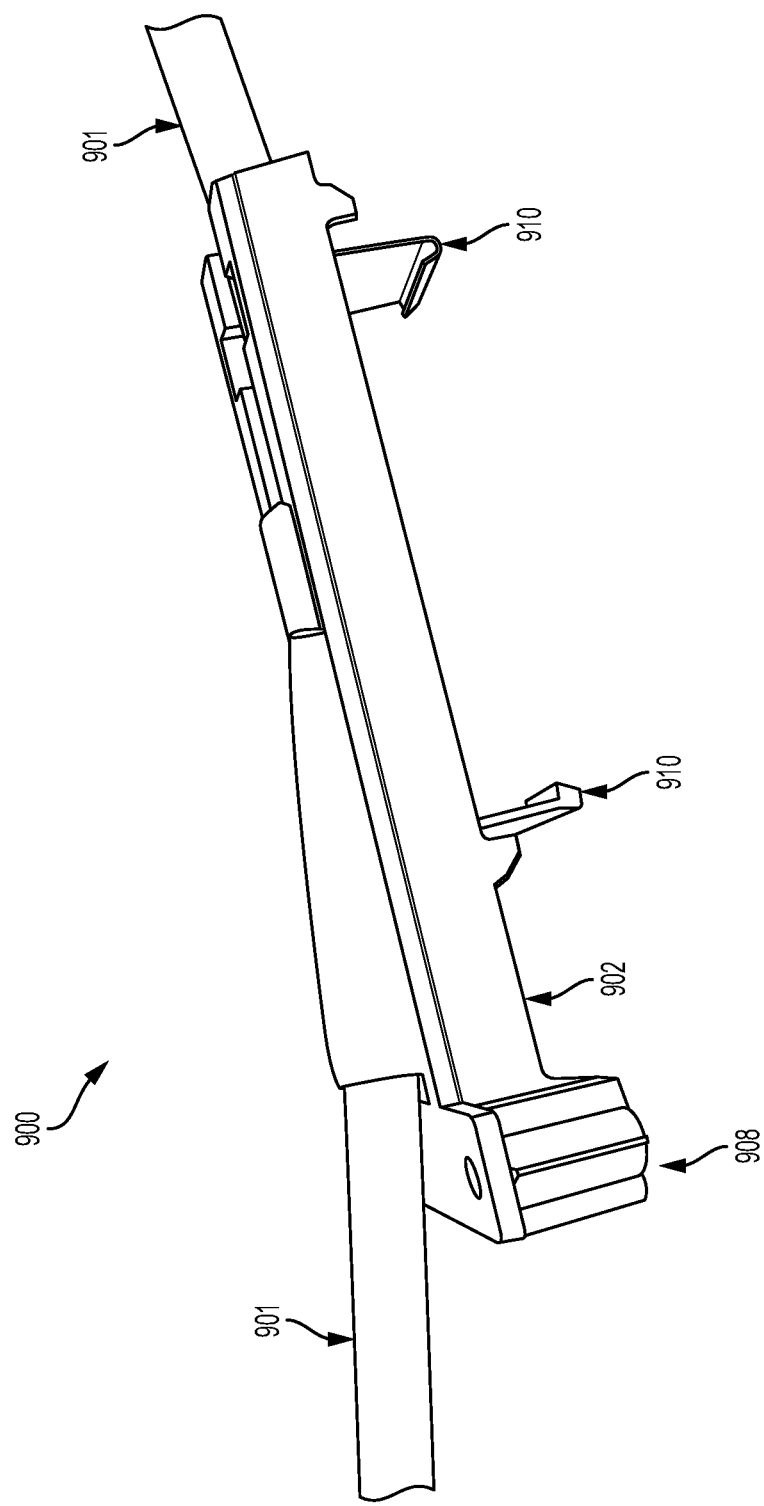
FIG. 9B illustrates a first detail view of a sensor assembly of a tabletop system for delivering a payload to a cell, in accordance with some embodiments.
Figure 9C:
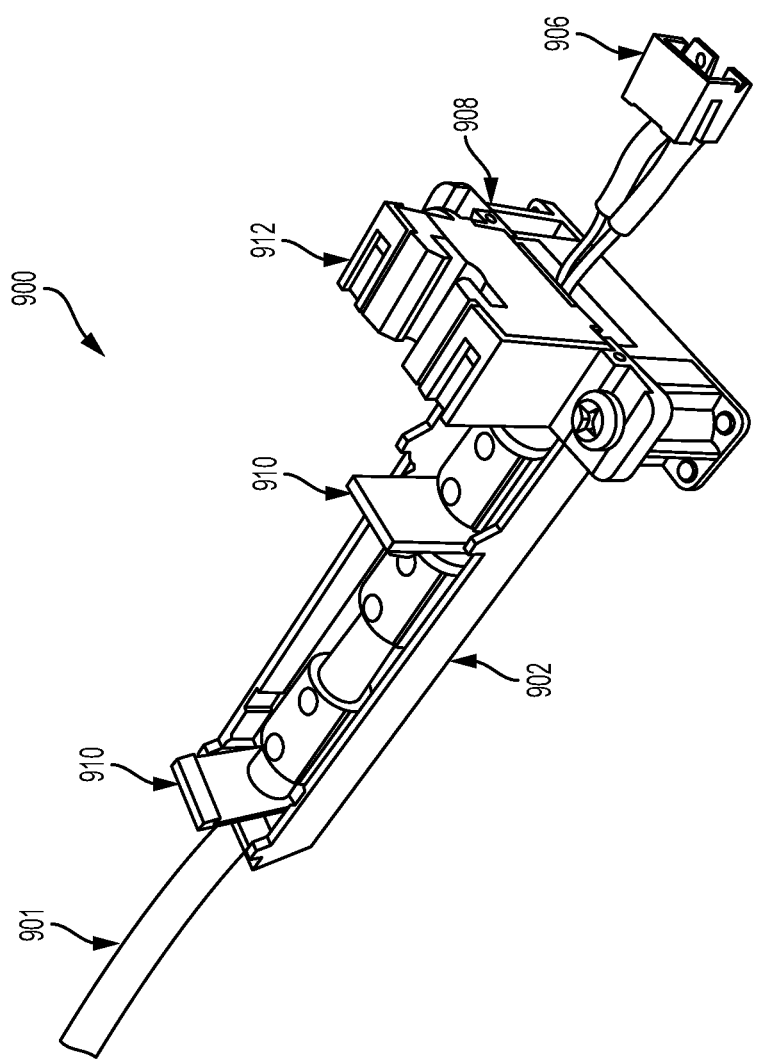
FIG. 9C illustrates a second detail view of a sensor assembly of a tabletop system for delivering a payload to a cell, in accordance with some embodiments.
Figure 9D:
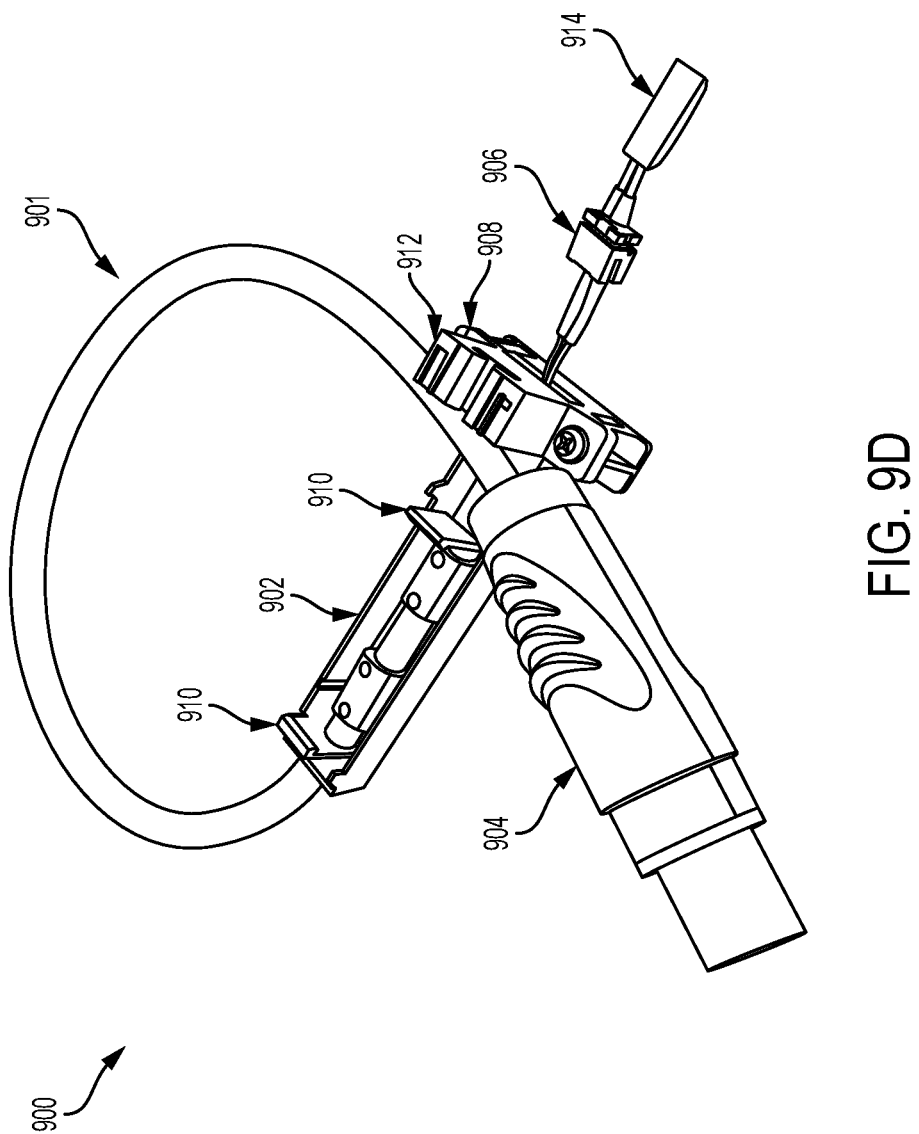
FIG. 9D illustrates a sensor assembly of a tabletop system for delivering a payload to a cell, in accordance with some embodiments.

In the example of FIGS. 9A-9D, FIG. 9A illustrates a partially assembled sensor assembly of a tabletop system for delivering a payload to a cell, in accordance with some embodiments; FIG. 9B illustrates a detail view of a sensor assembly of a tabletop system for delivering a payload to a cell, in accordance with some embodiments; FIG. 9C illustrates a detail view of a sensor assembly of a tabletop system for delivering a payload to a cell, in accordance with some embodiments; and FIG. 9D illustrates a sensor assembly of a tabletop system for delivering a payload to a cell, in accordance with some embodiments.

Sensor assembly 900 may comprise multi-pin sensor wire connector 904 at one end, one or more wires 901 running longitudinally along the length of the assembly, and temperature sensor connector 906 disposed at the opposite end of the wire(s) 901. In some embodiments, multi-pin wire connector 904 is an electronic connector configured to allow connection of the sensor to one or more electronic interfaces, such that electronic signals, such as signals representing the data measured or detected by the one or more sensors, may be sent and received via connector 904. In some embodiments, multi-pin wire connector 904 may be configured such that one or more pins of the connector may correspond to different sensors and may be configured to send and receive different kinds of data. In some embodiments, in place of or in addition to wire connector, alternate kinds of electronic connectors configured to send and receive data to and from other parts of system 100 may be used as part of sensor assembly 900. In some embodiments, because sensor assembly 900 may be configured to be disposable and to be able to be used in a sterile environment, connector 904 may be configured to be able to be easily attached and detached from an electronic interface by hand and/or without the use of tools.

Sensor assembly 900 may further comprise constriction cartridge seat 902, which may be a component configured to be mounted on wire(s) 901 and to hold a constriction cartridge, such as by removably clipping onto the constriction cartridge. In some embodiments, cartridge seat 902 may be formed to be able to attach to one or more kinds of constriction cartridges, such as constrictions cartridge 700 or constriction cartridge 800 as discussed above. In some embodiments, because sensor assembly 900 may be configured to be disposable and to be able to be used in a sterile environment, cartridge seat 902 may be configured to be able to be easily attached and detached from a constriction cartridge by hand and/or without the use of tools. In the example of FIGS. 9A-9D, constriction cartridge seat 902 includes clips 910 that may hold a constriction cartridge in place by tension; in alternate embodiments, different attachment means may be used.

In some embodiments, constriction cartridge seat 902 may be configured such that it attached to wire(s) 901 in such a way that wire(s) 901 runs in a same or similar direction as the linear direction defined by the flow path leading to a constriction cartridge inlet and from a constriction cartridge outlet when the constriction cartridge is attached to seat 902. In this way, sensor assembly 900 may be configured such that wire(s) 901 and tubes leading to/from a constriction cartridge may run alongside one another and may be able to pass through one or more of the same openings as one another, such as by passing through an outlet of a preparation vessel housing such as outlet 514 as discussed above with reference to preparation vessel housing 110.

Sensor assembly 900 may comprise temperature sensor connector 906, which may be any component configured to physically and/or electronically connect a temperature sensor to other components of sensor assembly 900. In the example of FIGS. 9A-9D, temperature sensor connector 906 may be an electrical connector disposed at an end of wire(s) 901 opposite from connector 904 and configured to detachably physically and electronically connect to a temperature sensor (e.g., a thermistor or temperature probe). As shown in FIG. 9D, temperature sensor 914 may be physically and electronically attached to temperature sensor connector 906, such that temperature sensor 914 may send signals via connector 906 (and through wire(s) 901 and connector 904) regarding temperature data measured by temperature sensor 914.

In some embodiments, temperature sensor 914 may be any device configured to measure one or more temperatures and to generate and/or transmit a signal regarding the one or more temperatures measured by the device. In some embodiments, temperature sensor 914 may be any suitable type of temperature probe or thermistor. In some embodiments, temperature sensor 914 may be an adhesive temperature probe configured to be adhered to a wall of a preparation vessel or preparation vessel housing in order to measure a temperature associated with a fluid (e.g., cell suspension) contained in the vessel.

In some embodiments, by being disposed at an end of wire(s) 901 opposite connector 904, temperature sensor 914 may be disposed such that it will be near a preparation vessel or preparation vessel housing when sensor assembly 900 is connected to system 100. For example, when a constriction cartridge is connected to seat 902 such that fluid may flow through the constriction cartridge from right to left with respect to FIG. 9A, temperature sensor 914 may be disposed near a preparation vessel or preparation vessel housing from which the fluid is flowing toward and through the constriction cartridge; in this way, temperature sensor 914 may be placed in physical contact with the preparation vessel or its housing in order to measure a temperature associated with the fluid in the preparation vessel while sensor assembly 900 and an associated chip cartridge are fully assembled to system 100.

Sensor assembly 900 may further comprise flow sensor connector 908, which may be any component configured to physically and/or electronically connect a flow sensor to other components of sensor assembly 900. In the example of FIGS. 9A-9D, flow sensor connector 908 may be an electrical connector disposed at one end of cartridge seat 902 and configured to physically and electronically connect to a flow sensor (e.g., an optical presence sensor, capacitive sensor, weight sensor, or other sensor configured to determine whether flow is occurring). As shown in FIGS. 9C and 9D, flow sensor 912 may be physically and electronically attached to flow sensor connector 908, such that flow sensor 912 may send signals via connector 908 (and through wire(s) 901 and connector 904) regarding data measured by flow sensor 912.

In some embodiments, flow sensor 912 may be any sensor configured to measure or otherwise determine whether flow is occurring in a particular part of a flow path, either by making an analog determination as to whether flow is occurring or by measuring a flow rate. In some embodiments, flow sensor 912 may be an optical sensor configured to use the presence, absence, and/or change of fluid in the path of a light beam to determine whether the fluid is flowing through the path; for example, flow sensor 912 may in some embodiments be a bubble sensor configured to determine whether flow is occurring through a translucent or transparent tube running through a path of a light beam of the bubble sensor. In some embodiments, flow sensor 912 may be a capacitive sensor configured to sense the presence of a liquid, it may be a weight sensor configured to sense the weight of a liquid, or it may be a physical sensor configured to be placed in a flow path to measure the speed and/or flow-rate of a fluid.

In some embodiments, by being disposed at on or near cartridge seat 902, flow sensor 912 may be disposed such that it will be near the constriction cartridge when sensor assembly 900 is connected to system 100. For example, when a constriction cartridge is connected to seat 902 such that fluid may flow through the constriction cartridge from right to left with respect to FIG. 9A, flow sensor 912 may be disposed near an inlet of the constriction cartridge, such that the flow sensor may measure flow of fluid through a tube or pipe as it approaches (or alternately, as it flows away from) the constriction cartridge. For example, if the flow sensor is an optical bubble sensor, then it may be configured such that a tube leading to an inlet of the constriction cartridge may be seated in a cavity of the bubble sensor such that the tube is in the optical path from which the sensor draws measurements. In this way, flow sensor 912 take measurements to determine whether fluid (e.g., cell suspension) is flowing toward, away from, and/or through the constriction cartridge while sensor assembly 900 and the chip cartridge are fully assembled to system 100.

Figure 10:
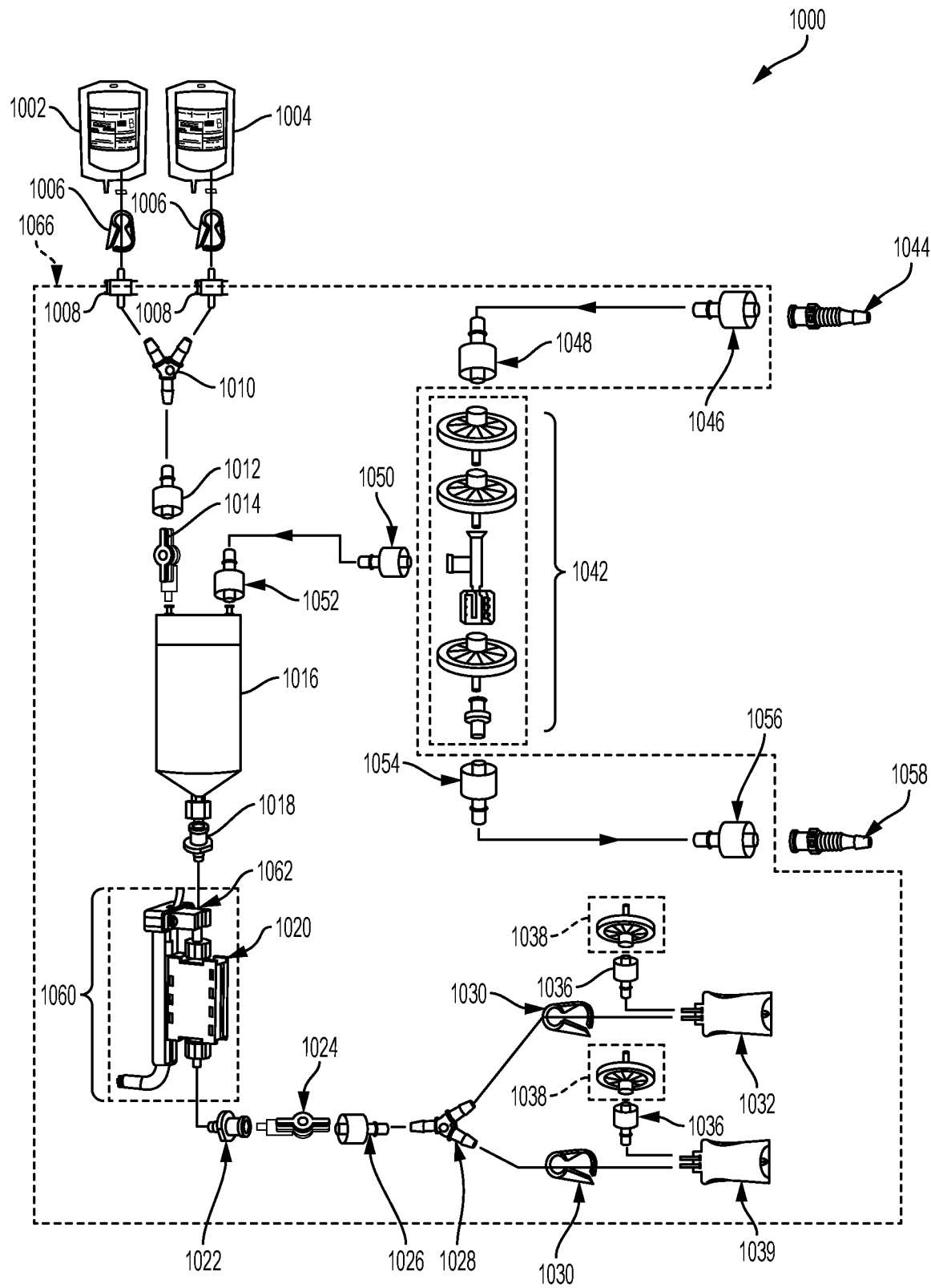
FIG. 10 illustrates schematic diagram of a tabletop system for delivering a payload to a cell, in accordance with some embodiments.

FIG. 10 illustrates a schematic diagram of a tabletop system 1000 for delivering a payload to a cell, in accordance with some embodiments. In some embodiments, system 1000 may share some or all characteristics in common with system 100, and/or with any other system for delivering a payload to a cell discussed herein. Rather than depicting the physical shape of various components of the system for delivering a payload to a cell, FIG. 10 primarily schematically depicts the flow paths and associated components for fluid (e.g., cell suspension, buffer fluid) traveling through the system and for pressurized gas traveling through the system. That is, FIG. 10 depicts the various components through which cell suspension and/or buffer fluid may flow while being processed by the system, and depicts the various components through which gas (e.g., pressurized gas) may flow when being passed through the system. FIG. 10 shows components fluidly connected to one another via arrows and lines connecting the depictions of the components; where not otherwise noted, any suitable tubing or piping may be used to fluidly connect the various components, such as flexible plastic tubing, rigid plastic tubing, PVC tubing, metal tubing, or the like.

System 1000 may comprise cell suspension input bag 1002, which may share some or all characteristics in common with cell suspension input bag 106 discussed above with reference to FIG. 1. In some embodiments, a flow path of liquid flowing through system 1000 may originate (or part of it may originate) with cell suspension input bag 1002.

System 1000 may comprise buffer input bag 1004, which may share some or all characteristics in common with buffer input bag 108 discussed above with reference to FIG. 1. In some embodiments, a flow path of liquid flowing through system 1000 may originate (or part of it may originate) with buffer input bag 1004.

System 1000 may comprise tubing clamps 1006, which may be used to prevent liquid from flowing through the tubing extending from cell suspension input bag 1002 or buffer input bag 1004. In some embodiments, other mechanisms for preventing flow from the bags, such as valves, caps, or the like, may be used alternately or in addition to clamps 1006. In some embodiments, clamps 1006 may be configured to be able to be automatically actuated by an electronic control system, such that manual actuation by a user is not required.

System 1000 may comprise fittings 1008, which may be any fittings 1008, which may be any connector configured to fluidly connect tubing or piping extending from bags 1002 and 1004 to additional components of system 1000 defining a further downstream portion of the flow path. In some embodiments, fittings 1008 may be a connector mechanism configured to provide a sterile connection (e.g., a connector mechanism configured to ensure that the interior of the flow path does not become contaminated from being directly handled as the connection is secured), such as an ASEPTIQUIK® sterile fitting. In some embodiments, in addition to or in place of fittings 1008, one or more connection mechanisms other than fittings may be used, such as tube welding connections, sterile assembly connections, etc.

System 1000 may comprise Y-fitting 1010, which may be any diverter or junction configured to cause the flow path from bag 1002 and the flow path from bag 1004 to converge into a single flow path.

System 1000 may comprise connector 1012, which may be any suitable tubing or piping fitting or connector for connecting tubing or piping of the flow path of system 1000 to valve 1014 such that fluid may flow into valve 1014. In some embodiments, connector 1012 may be a threaded fitting and/or a Luer-style fitting.

System 1000 may comprise valve 1014, which may be any valve configured to control the flow of fluid from connector 1012 toward and into vessel 1016. In some embodiments, valve 1014 may be a syringe valve, a manual valve, an electronic valve, and/or a solenoid valve. In some embodiments, valve 1014 may be configured to be able to be automatically actuated by an electronic control system, such that manual actuation by a user is not required.

System 1000 may comprise vessel 1016, which may share any one or more characteristics in common with preparation vessel 600 discussed above with respect to FIGS. 6A and 6B.

System 1000 may comprise connector 1018, which may share any one or more characteristics in common with connector 1012. Connector 1018 may be configured to connect tubing or piping of the flow path of system 1000 to vessel 1016 such that fluid may flow out of vessel 1016.

System 1000 may comprise constriction cartridge 1020, which may share any one or more characteristics in common with constriction cartridge 700 and/or constriction cartridge 800 described above with respect to FIGS. 7A-7C and 8A-8D. Although system 1000 is shown with only one constriction cartridge 1020, some embodiments of system 1000 (or other systems described herein) may comprise multiple constriction cartridges that may be arranged in parallel and/or in series with one another. In some embodiments, multiple constriction cartridges in the same system may be associated with the same sensor assembly or with separate sensor assemblies; with the same preparation vessel or with separate preparation vessels; and/or with the same set of input/output containers or with separate sets of input/output containers.

System 1000 may comprise connector 1022, which may share any one or more characteristics in common with connector 1012. Connector 1022 may be configured to connect tubing or piping of the flow path of system 1000 to valve 1024 such that fluid may flow from constriction cartridge 1020 toward and into valve 1024.

System 1000 may comprise valve 1024, which may share some or all characteristics in common with valve 1014. Valve 1024 may be configured to control the flow of fluid from connector 1022 toward and into connector 1026, or more broadly from constriction cartridge 1020 toward and into output bags 1032 and 1039.

System 1000 may comprise connector 1026, which may share any one or more characteristics in common with connector 1012. Connector 1026 may be configured to connect tubing or piping of the flow path of system 1000 to valve 1024, such that fluid may flow out of syringe 1024 and toward output bags 1032 and 1039.

System 1000 may comprise Y-fitting 1028, which may be any diverter or junction configured to cause the flow path from connector 1026 to divert into two separate flow paths, one leading toward cell suspension output bag 1032 and the other leading toward buffer output bag 1039.

System 1000 may comprise clamps 1030, which may share any one or more characteristics in common with clamps 1006. In some embodiments, clamps 1030 may be used to prevent liquid from flowing through the tubing leading to cell suspension output bag 1032 or buffer output bag 1039. In some embodiments, other mechanisms for preventing flow to the bags, such as valves, caps, or the like, may be used alternately or in addition to clamps 1030. In some embodiments, clamps 1030 may be configured to be able to be automatically actuated by an electronic control system, such that manual actuation by a user is not required.

System 1000 may comprise cell suspension output bag 1032, which may share any one or more characteristics in common with cell suspension output bag 112 as described above with respect to FIG. 1. In some embodiments, a flow path of liquid flowing through system 1000 may terminate (or part of it may terminate) with cell suspension input bag 1002.

System 1000 may comprise buffer output bag 1039, which may share any one or more characteristics in common with buffer output bag 114 as described above with respect to FIG. 1. In some embodiments, a flow path of liquid flowing through system 1000 may terminate (or part of it may terminate) with buffer output bag 1039.

System 1000 may comprise connectors 1036, which may share any one or more characteristics in common with connector 1012. Connectors 1036 may each connect a gas outlet line that extend from one of output bags 1032 and 1039 to allow gas to be forced out of the output bag before, during, or after the process of causing the cell suspension and/or buffer fluid to flow through system 1000 and into the output bag. For example, because fluid may be forced through system 1000 under the force of pressurized air, it may be necessary for the output bags, which may form a termination point of a flow path for cell suspension and/or buffer fluid through system 1000, to have a gas outlet to prevent the bags from rupturing under pressure.

System 1000 may comprise filters 1038, which may be gas filters each connected to one of connectors 1036, such that air or other gas may flow through one of the output bags, through one of filters 1038, and into the environment exterior to system 1000. In some embodiments, filters 1038 may ensure that gas that is expelled into the environment external to system 1000 is suitable for a sterile environment. In some embodiments, one or both of filters 1038 may share one or more characteristics in common with filter 404, as discussed above with respect to FIG. 4. For example, filters 1038 may be HEPA filters suitable for use in filtering exhaust to be expelled into a sterile laboratory environment.

System 1000 may comprise filter sub-assembly 1042, which may be pre-sterilized or configured to be able to be sterilized (e.g., by autoclaving or by ethylene oxide sterilization). In some embodiments, filter sub-assembly 1042 may be configured to receive gas, such as pressurized sterile gas (e.g., pressurized sterile nitrogen) from an inlet, direct some of the gas into vessel 1016, and direct some of the gas to an outlet. As shown in FIG. 10, filter sub-assembly 1042 may receive gas from gas inlet 1044, may direct some or all of the gas received to vessel 1016, and may direct some or all of the gas received to outlet 1058. In some embodiments, filter sub-assembly 1042 may be used to direct pressurized sterile gas into vessel 1016 in order to cause pressure to be applied to fluid (e.g., cell suspension) in vessel 1016 in order to force the fluid under pressure to flow out of vessel 1016 and through constriction cartridge 1020. As shown in FIG. 10, system 1000 may in some embodiments comprise multiple filters in series, as redundancy may improve reliability and safety. In some embodiments, filter sub-assembly 1042 may be disposed externally to a housing of system 1000 so that filter sub-assembly 1042 may be easily replaced.

System 1000 may comprise gas inlet 1044, which may comprise any suitable flexible or rigid inlet configured to receive a flow of gas, such as pressurized sterile gas. In some embodiments, gas inlet 1044 may be configured to be able to be fluidly connected with flexible tubing for gas and/or rigid tubing for gas. In some embodiments, gas inlet 1044 may be configured to be fluidly connectible to tubing by clamps, threads, Luer-style connectors, or any other suitable connection mechanism.

System 1000 may comprise gas outlet 1058, which may be any suitable flexible or rigid outlet configured to expel a flow of gas, such as pressurized sterile gas. In some embodiments, gas outlet 1058 may be configured to be able to be fluidly connected with flexible tubing for gas and/or rigid tubing for gas. In some embodiments, gas outlet 1058 may be configured to be fluidly connectible to tubing by clamps, threads, Luer-style connectors, or any other suitable connection mechanism.

System 1000 may further comprise connectors 1046, 1048, 1050, 1052, 1054, and 1056, any one or more of which may share any one or more characteristics in common with connector 1012. While connector 1012 may be configured to connect tubing or piping or other flow path elements for a flow path of a liquid, connectors 1046, 1048, 1050, 1052, 1054, and 1056 may be configured to connect tubing or piping or other flow path elements for a flow path of a gas. As shown in FIG. 10, connectors 1046, 1048, 1050, 1052, 1054, and 1056 may be used to connect tubing or piping elements between gas inlet 1044, filter sub-assembly 1042, vessel 1016, and gas outlet 1058. In this way, connectors 1046, 1048, 1050, 1052, 1054, and 1056 may allow gas to flow from the inlet through the filter sub-assembly and to the vessel of the outlet.

System 1000 may comprise sensor assembly 1060, which may share any one or more characteristics in common with sensor assembly 900 discussed above with reference to FIGS. 9A-9D. In some embodiments, sensor assembly 1060 may comprise one or more sensors not depicted in FIG. 10, such as a temperature sensor.

System 1000 may comprise flow sensor 1062, which may in some embodiments be part of sensor assembly 1060. In some embodiments, flow sensor 1062 may share any one or more characteristics in common with flow sensor 912 discussed above with reference to FIGS. 9C and 9D.

In some embodiments, one or more components shown in FIG. 10 may together form all or part of a disposable assembly. For example, the components may be configured for one-time use, such that they may be used to perform a payload delivery process once and then be disposed of. That is, cell suspension may flow through the flow path of system 1000 one time, and then some or all of the elements of system 1000 may be replaced before another payload delivery process is performed. In some embodiments, components of a disposable assembly may be constructed from materials that are suitable for being gamma sterilized in order to suitable for use in a sterile environment. In some alternate embodiments, components of a disposable assembly may be constructed from materials that are suitable for being sterilized by other methods, such as autoclaving or ethylene oxide sterilization. In some embodiments, components of a disposable assembly may be packaged and/or shipped together, such as being packaged and/or shipped in a sealed sterile container. In some embodiments, components of a disposable assembly may be configured to be able to be attached to other components of a system for intracellular payload delivery in a manner suitable for being performed in a sterile environment, such as by being attached by hand, without the use of tools, and/or by using sterile connector mechanisms. In the example of FIG. 10, disposable assembly 1066 may include all components shown inside the dotted box indicated by the 1066 reference numeral.

Figure 11A:
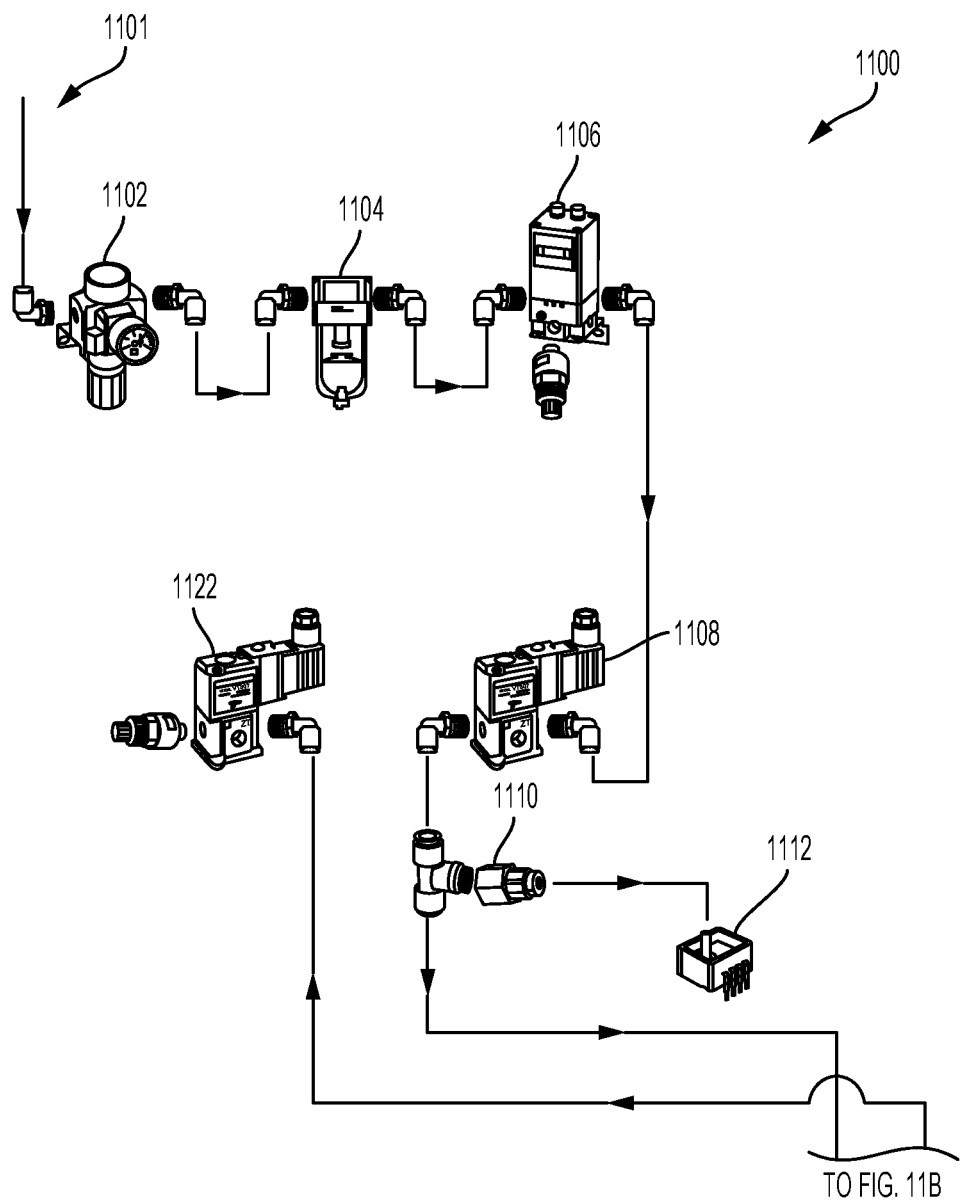
FIGS. 11A and 11B illustrate a schematic diagram of a system for supplying pressurized gas for use in delivering a payload to a cell, in accordance with some embodiments.
Figure 11B:
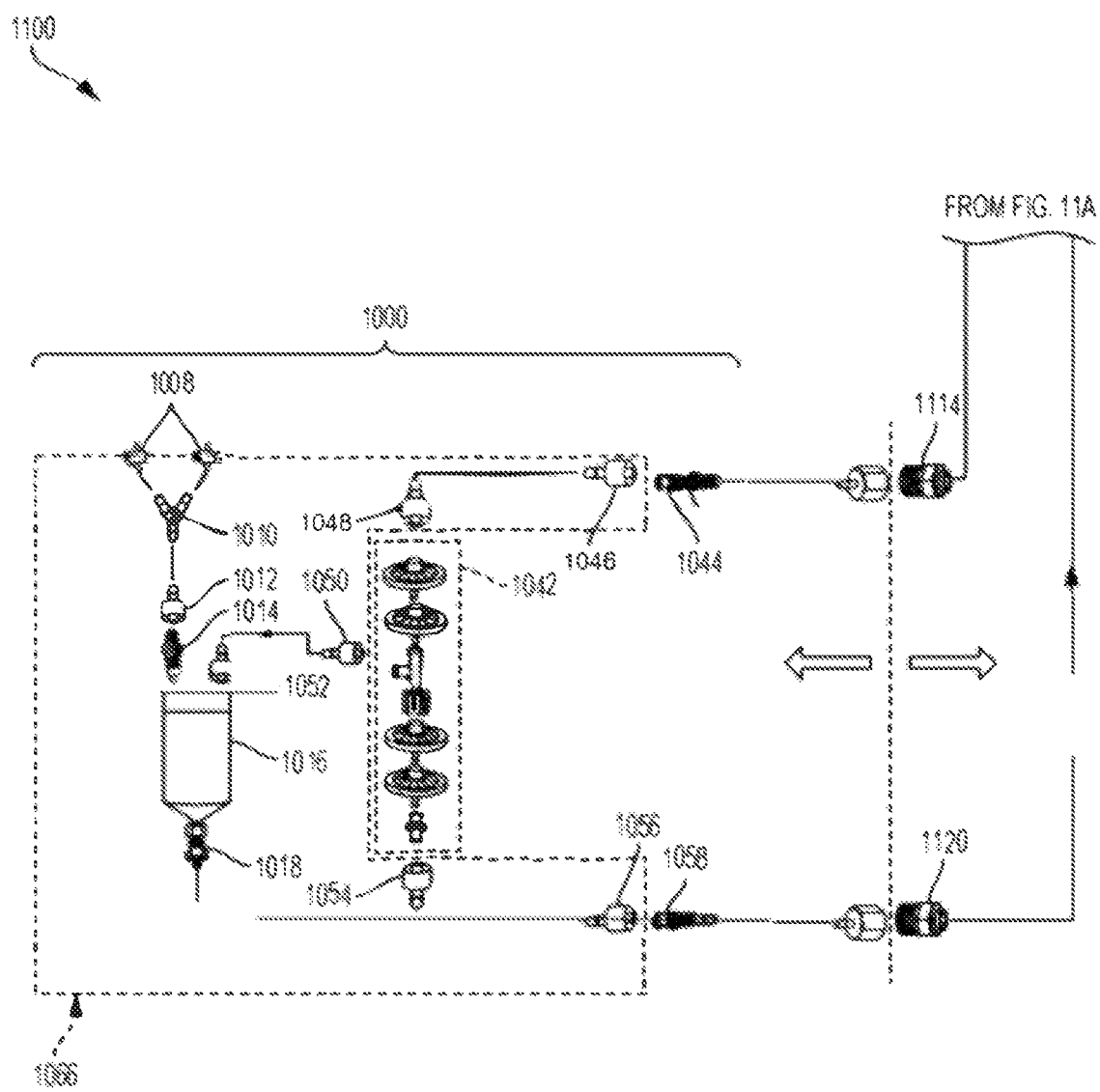

FIGS. 11A and 11B illustrate a schematic diagram of a system 1100 for supplying pressurized gas for use in delivering a payload to a cell, in accordance with some embodiments. In some embodiments, system 1100 may be configured to supply pressurized gas to a system such as system 1000 as discussed above with reference to FIG. 10. In some embodiments, system 1100 may form a part of, or may share some or all characteristics in common with, pressure control module 116 discussed above with respect to FIGS. 1 and 2. As shown in FIGS. 11A and 11B, system 1100 may comprise a flow path for gas, such as pressurized sterile gas (e.g., pressurized sterile nitrogen) to flow from an inlet source toward and into a system having a vessel containing fluid (e.g., cell suspension) and also to flow toward and out of an outlet and into an environment external to system 1100 and/or external to associated systems such as system 1000. In some embodiments, system 1100 may be used to direct pressurized sterile gas into vessel 1016 in order to cause pressure to be applied to fluid (e.g., cell suspension) in vessel 1016 in order to force the fluid under pressure to flow out of vessel 1016 and through constriction cartridge 1020.

FIGS. 11A and 11B show components fluidly connected to one another via arrows and lines connecting the depictions of the components; where not otherwise noted, any suitable tubing or piping may be used to fluidly connect the various components, such as flexible plastic tubing, rigid plastic tubing, PCV tubing, metal tubing, or the like.

As shown in FIG. 11A, system 1100 may comprise inlet 1101, which may be any inlet configured to be fluidly connected to a source of gas, such as pressurized sterile gas (e.g., pressurized sterile nitrogen). In some embodiments, inlet 1101 may comprise any suitable flexible or rigid inlet configured and/or connector configured to receive a flow of gas, such as pressurized sterile gas. In some embodiments, inlet 1101 may be configured to be able to be fluidly connected with flexible tubing for gas and/or rigid tubing for gas, may be configured to be able to be fluidly connected with a pressurized gas canister, and/or may be configured to draw gas from the environment (e.g., from the air). In some embodiments, inlet 1101 may be configured to be fluidly connectible to tubing by clamps, threads, Luer-style connectors, or any other suitable connection mechanism in order to direct the flow of gas toward regulator 1102.

System 1100 may comprise regulator 1102, which may be configured to be fluidly connected to and receive a flow of gas from inlet 1101. In some embodiments, regulator 1102 may be configured to receive a flow of gas and to output the gas at a predetermined pressure. In some embodiments, the pressure of gas output by regulator 1102 may be controlled by a user or may be automatically controlled by the system. In some embodiments, the pressure of gas output by regulator 1102 may be changeable by electronic controls such that manual intervention is not required.

System 1100 may comprise filter 1104, which may be configured to be fluidly connected to and receive a flow of gas from regulator 1102. In some embodiments, filter 1104 may be any filter configured such that gas output by regulator 1102 may pass through it before flowing along the flow path to regulator 1106. For example, filter 1104 may be a HEPA filter such that system 1100 and associated systems may be suitable for use in a sterile environment.

System 1100 may comprise regulator 1106, which may be configured to be fluidly connected to and receive a flow of gas from filter 1104. In some embodiments, regulator 1106 may be configured to receive gas flow at one pressure and to output gas flow at another, lower, user- or system-selectable pressure. In some embodiments, regulator 1106 may be an electro-pneumatic regulator and may share some or all properties in common with regulator 204 as described above with respect to FIG. 2. In some embodiments, regulator 1106 may comprise a silencer for reducing vibration and noise. Use of a silencer for reducing vibration and noise may make system 1100 more suitable for use in a sterile environment in that it may minimize the agitation of particles in the environment. In some embodiments, regulator 1106 may be configured for more precise pressure control over a narrower range than regulator 1102, which may be configured to control pressure more crudely over a broader range.

System 1100 may comprise valve(s) 1108, which may be configured to be fluidly connected to and receive a flow of gas from regulator 1106. Valve(s) 1108 may be configured to block or allow the flow of gas toward diverter 1110. In some embodiments, valve(s) 1108 may be manually and/or electronically actuable, and valve(s) 1108 may be actuated by a user or by an electronic system in accordance with operation of the system and without user intervention.

System 1100 may comprise diverter 1110, which may be configured to be fluidly connected to and receive a flow of gas from valve(s) 1108. In some embodiments, diverter 1110 may be any piping or tubing element configured to divert a single flow path into one or more flow paths. In the example shown in FIG. 11A, diverter 1110 diverts the flow path extending from valve(s) 1108 into two flow paths, one flowing toward pressure sensor 1112 and another flowing toward fitting 1114 in FIG. 11B. In some embodiments, diverter 1110 may comprise one or more valves that may be opened or closed to selectively divert flow of gas along one path or another; in some embodiments, diverter 1110 may be configured such that both downstream flow paths are always open and gas is always directed into both flow paths.

System 1100 may comprise pressure sensor 1112, which may be configured to be fluidly connected to and receive a flow of gas from diverter 1110. In some embodiments, pressure sensor 1112 may be configured to measure a pressure of gas in the flow path of system 1100 between valve(s) 1108 and fitting 1114. In some embodiments, pressure sensor may be configured to generate data representing the pressure measurements taken and to send electronic signals representing the data to one or more other components of system 1100, system 1000, or associated systems. For example, pressure sensor 1112 may send signals regarding the pressure measured to regulator 1106 such that regulator 1106 may make adjustments to the pressure of gas output by regulator 1106 as required. In some embodiments, for example, gas pressure may drop as the cell suspension is forced out of the preparation vessel and into and through the constriction cartridge, and pressure sensor 1112 may sense this decrease in pressure and send signals to a processor of the system (e.g., regulator 1106 and/or another component of a pressure control module) to cause the system to adjust one or more valves to cause the pressure to remain relatively constant as the cell suspension is forced out of the vessel.

As shown in FIG. 11B, system 1100 may comprise fitting 1114, which may be configured to be fluidly connected to and receive a flow of gas from diverter 1110 and direct it toward system 1000. In some embodiments, fitting 1114 may be any connector configured to be fluidly connected with flexible tubing for gas and/or rigid tubing for gas. In some embodiments, fitting 1114 may be configured to be able to be fluidly connected to rigid tubing on an upstream side and to flexible tubing on a downstream side. In some embodiments, fitting 1114 may be configured to be fluidly connectible to tubing by clamps, threads, Luer-style connectors, or any other suitable connection mechanism in order to direct the flow of gas toward system 1000.

As shown in FIG. 11B, fitting 1114 may connect components of system 1100 to one or more components of system 1000. In particular, fitting 1114 may be configured to be fluidly connected (and/or connectible) to a flow path leading to inlet 1044 of system 1000. In some embodiments, gas delivered from system 1100 to system 1000 via fitting 1114 and inlet 1044 may be used to apply pressure to fluid inside vessel 1016, as described above with reference to FIG. 10.

System 1100 may comprise fitting 1120, which may share any one or more characteristics in common with fitting 1114. Fitting 1120 may be configured to be fluidly connected (or connectible) to a flow path leading from outlet 1058 of system 1000. In some embodiments, gas output by outlet 1058 in system 1000 as described with reference to FIG. 10 may flow through fitting 1120 and into the flow path depicted in FIGS. 11A and 11B.

As shown in FIG. 11A, system 1100 may comprise silencer 1122. In some embodiments, silencer 1122 may be configured such that gas may flow through it before being expelled into an environment external to system 1100 (e.g., into the open air). In some embodiments, silencer 1122 may reduce vibration and noise and may make system 1100 more suitable for use in a sterile environment in that it may minimize the agitation of particles in the environment.

Intracellular Payload Delivery and Cell Processing Methods and Techniques

Figure 12:
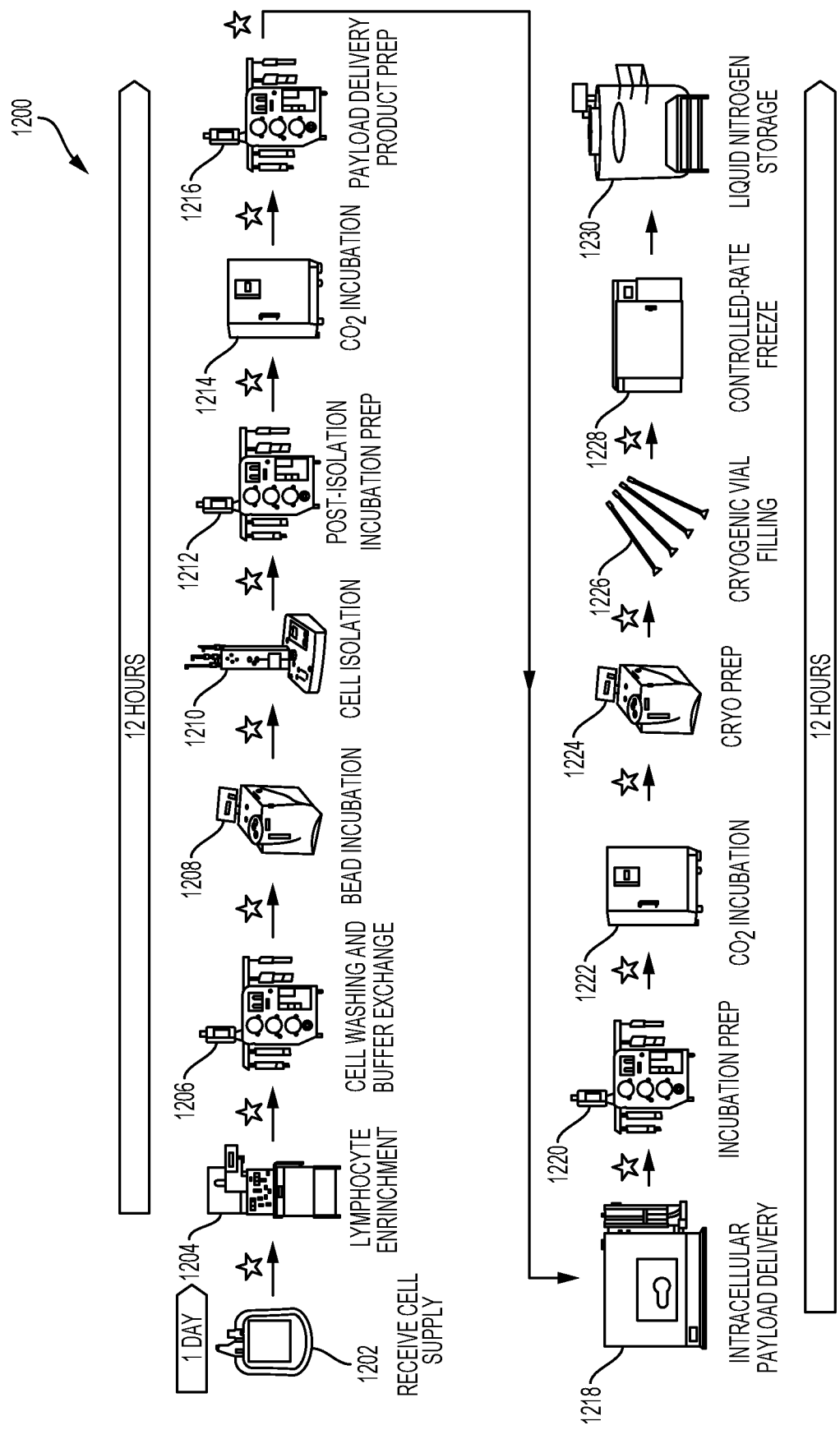
FIG. 12 illustrates a method for processing cells including intracellular payload delivery, in accordance with some embodiments.
Figure 13:
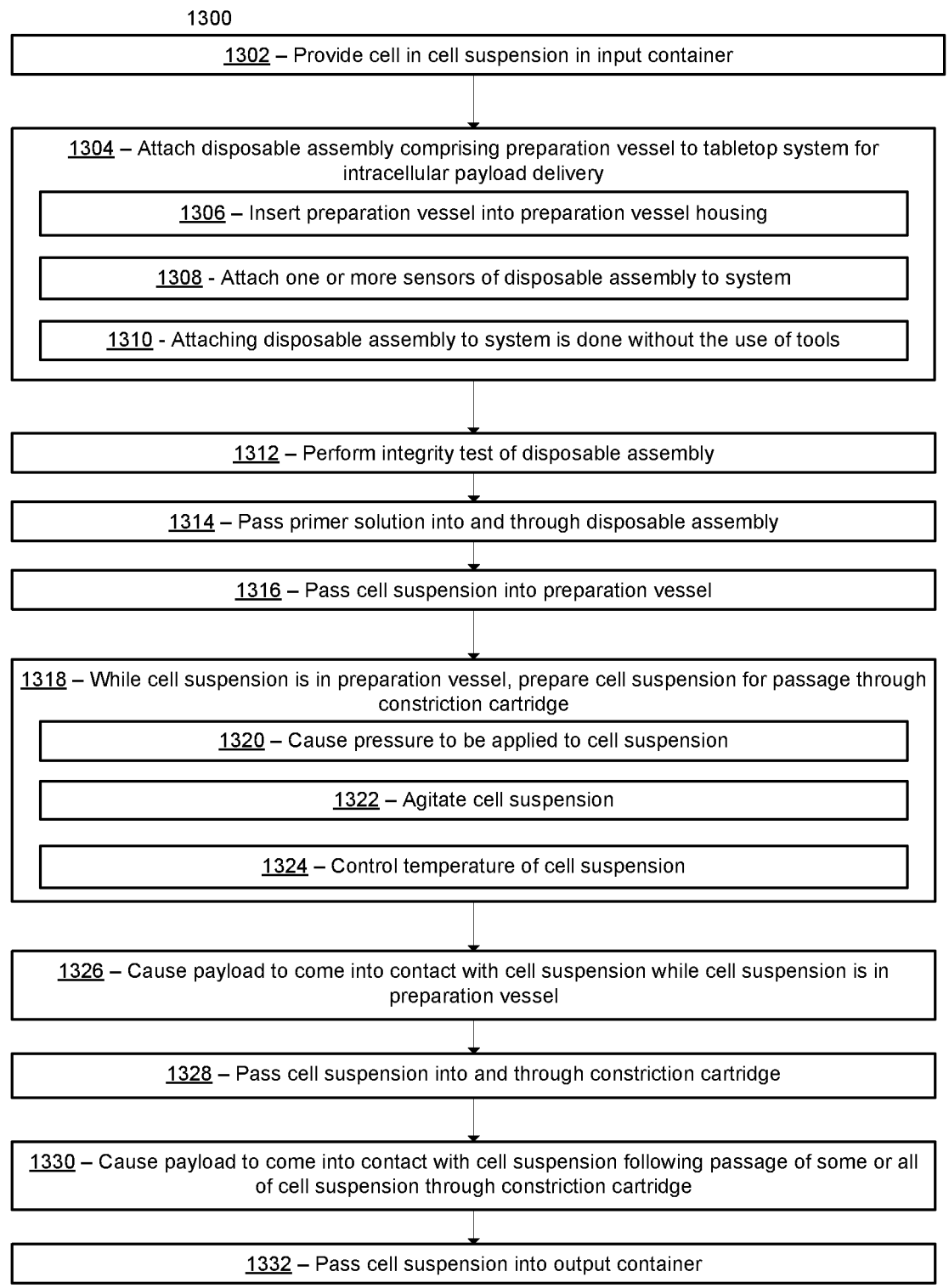
FIG. 13 illustrates a method for intracellular payload delivery, in accordance with some embodiments.

FIGS. 12-13 describe various methods that may be performed, in whole or in part, by one or more of the systems described herein.

FIG. 12 illustrates method 1200 for processing cells including intracellular payload delivery, in accordance with some embodiments. As indicated in FIG. 12, method 1200 may in some embodiments be performed in the course of 24 hours or less. In some alternate embodiments, method 1200 may be performed in 72 hours or less, 36 hours or less, 18 hours or less, or 12 hours or less. In some embodiments, performing method 1200 in less than one of the indicated time-frames may improve throughput and efficiency for cell processing and intracellular payload delivery techniques. In some embodiments, the time-frames contemplated herein may be facilitated by the rapid-throughput intracellular payload delivery techniques made possible by the systems and methods described elsewhere herein.

At step 1202, in some embodiments, a supply of cells is received. In some embodiments, the supply of cells may comprise a variety of blood cells including monocytes, lymphocytes, platelets, plasma, and red cells. In some embodiments, the supply of cells may comprise an enriched leukapheresis product such as a LEUKOPAK®, or a similar product, which may be delivered overnight at room temperature.

At step 1204, in some embodiments, the supply of cells may be processed for lymphocyte enrichment. In some embodiments, lymphocyte enrichment may be performed by an ELUTRA® cell separation system, or by a similar system.

At step 1206, in some embodiments, the cells may be processed for washing and/or buffer exchange. In some embodiments, cell washing and/or buffer exchange may be performed by a LOVO® automated cell processing system, or by a similar system.

At step 1208, in some embodiments, the cells may be incubated. In some embodiments, the incubation may be bead incubation. In some embodiments, the bead incubation may be performed using polymer resin beads. In some embodiments, the bead incubation may be performed using a SEPAX™ system and/or SEPAX™ polymer resin beads, or using similar systems and/or materials.

At step 1210, in some embodiments, target cells may be isolated from the cells. In some embodiments the target cells to be isolated may comprise NK cells, T cells, B cells, and/or other cell types. In some embodiments, the target cells may be isolated using a positive selection process (e.g., tagging the target cells) or a negative selection process (e.g., tagging cells other than the target cells). In some embodiments, the cells may be separated on the basis of their relative density. In some embodiments, isolating target cells may comprise isolating a single type of cells, while in some embodiments it may comprise isolating a plurality of different types of cells that are all target cells. In some embodiments, the target cells may be isolated by a CLINIMACS® automated cell separation system, or by a similar system.

At step 1212, in some embodiments, the target cells may be processed for post-isolation incubation preparation. In some embodiments, the incubation preparation processing may prepare the target cells for $CO_2$ incubation. In some embodiments, the post-isolation incubation preparation processing may be performed by a LOVO® automated cell processing system, or by a similar system.

At step 1214, in some embodiments, the target cells may be incubated. In some embodiments, the incubation may be $CO_2$ incubation at about 37 C°.

At step 1216, in some embodiments, the target cells may be prepared for a payload delivery process, wherein the payload delivery process may comprise causing a perturbation in membranes of the target cells in order to enable a payload material to enter the target cells. In some embodiments, the payload delivery process preparation may comprise removing an original buffer and/or suspending the target cells in a fluid (e.g., a delivery buffer) to create a cell suspension. In some embodiments, the cell suspension may include the payload to be delivered to the cells, while in some embodiments the payload may not be included in the cell suspension (and the payload may instead be caused to come into contact with the cells after the cell suspension is passed through all or part of the system; while the cell suspension is inside the preparation vessel; before all or part of the cell suspension passes through the disposable assembly; before all or part of the cell suspension passes through the constriction cartridge; after all or part of the cell suspension passes through the disposable assembly; after all or part of the cell suspension passes through constriction cartridge; before some or all of the cell membranes are perturbed by being passed through one or more constrictions; after some or all of the cell membranes are perturbed by being passed through one or more constrictions; inside the preparation vessel; inside the constriction cartridge; inside an output bag; and/or inside any one or more other portions of a flow path of the system).

At step 1218, in some embodiments, the target cells may be processed by an intracellular payload delivery system in order to cause a payload to be delivered to the target cells. In some embodiments, the intracellular payload delivery system may pass the target cells through one or more constrictions in order to cause perturbations in the membranes of the target cells and thereby allow entry of the payload into the target cells. In some embodiments, the intracellular payload delivery system may share any one or more properties in common with systems 100, 1000, and/or 1100 as described above. The intracellular payload delivery technique, particularly as it may be performed by a tabletop system for payload delivery, will be discussed in greater detail below with respect to FIG. 13.

In some embodiments where intracellular payload delivery is performed by an intracellular payload delivery system such as system 100, 1000, and/or 1100, the system may be configured to be attached to one or more other cell processing systems or devices described herein and/or used elsewhere in method 1200. For example, in some embodiments, the cell suspension may be configured to flow directly from a separate device into one or more components of an intracellular payload delivery system, such as into an input bag, into a preparation vessel, and/or into a constriction cartridge (with or without first being held in a preparation vessel).

At step 1220, in some embodiments, the target cells with delivered payloads may be processed for post-payload-delivery incubation preparation. In some embodiments, the incubation preparation processing may prepare the target cells for $CO_2$ incubation. In some embodiments, the post-payload-delivery incubation preparation processing may be performed by a LOVO® automated cell processing system, or by a similar system.

At step 1222, in some embodiments, the target cells may be incubated. In some embodiments, the incubation may be $CO_2$ incubation.

At step 1224, in some embodiments, the target cells may be prepared for cryogenic preservation. In some embodiments, the cryogenic preservation preparation may be performed by using a SEPAX™ system, or by a similar system.

At step 1226, in some embodiments, the target cells may be placed in cryogenic vials. In some embodiments, the cryogenic vials may be any sterile vials suitable for cryogenic preservation and storage.

At step 1228, in some embodiments, the cryogenic vials containing the target cells with delivered payloads may be frozen. In some embodiments, the freezing process may be performed at a controlled rate by a controlled-rate freezer system, which may prevent damage to the cells by preventing them from being frozen too quickly.

Lastly, at step 1230, in some embodiments, the frozen cryogenic vials may be stored in a liquid-nitrogen storage system.

FIG. 13 illustrates method 1300 for intracellular payload delivery, in accordance with some embodiments. In some embodiments, all or part of method 1300 may be performed as step 1218 of method 1200 as described above with reference to FIG. 12. In some embodiments, method 1300 may be used to process cells by an intracellular payload delivery system in order to cause a payload to be delivered to the cells. In some embodiments, the intracellular payload delivery system may pass the cells through one or more constrictions in order to cause perturbations in the membranes of the cells and thereby allow entry of the payload into the cells. In some embodiments, the intracellular payload delivery system may share any one or more properties in common with systems 100, 1000, and/or 1100 as described above. Below, method 1300 will be described primarily with reference to components of system 100 as described above in FIGS. 1-9D.

At block 1302, in some embodiments, a cell in a cell suspension may be provided to the intracellular payload delivery system. In some embodiments, the cell in the cell suspension may be provided in the form of a cell suspension fluid provided in a cell suspension input bag such as bag 106 of system 100. Providing the cell in cell suspension may comprise hanging bag 106 from hook 104 and attaching tubing from bag 106 to an inlet of system 100, such as an inlet provided atop preparation vessel housing 110 and/or one of fittings 1008 in system 1000.

As will be discussed in further detail below, the cell may in some embodiments be provided as part of a cell suspension that contains the payload for delivery to the cell. In some other embodiments, the cell may be provided as part of a cell suspension that does not contain the payload for delivery to the cell, and the payload may instead be brought into contact with the cell and/or cell suspension at a later time.

At block 1304, in some embodiments, a disposable assembly comprising a preparation vessel may be attached to the intracellular payload delivery system. In some embodiments, the disposable assembly may comprise a preparation vessel such as preparation vessel 600, a constriction cartridge such as constriction cartridge 700 and/or constriction cartridge 800, and/or a sensor assembly such as sensor assembly 900. In some embodiments, the disposable assembly may comprise any one or more of the components included in disposable assembly 1066 of system 1000. In some embodiments, attaching the disposable assembly to the system may comprise physically, fluidly, and/or electronically/communicatively connecting one or more components of the disposable assembly to the system. For example, a preparation vessel of the disposable assembly may be physically attached to the system by being placed inside a receiver or housing, one or more tubes or pipes of the disposable assembly may be fluidly connected to the system (e.g., by Luer-style connectors) such that liquid and/or gas may flow through the tubes or pipes, and one or more electronic connectors of the sensor assembly may be electronically communicatively coupled to the system such that signals and data from sensors of the sensor assembly may be sent to electronic components of the system.

At block 1306, in some embodiments, attaching the disposable assembly may comprise inserting a preparation vessel of the disposable assembly into a preparation vessel housing. In the example of system 100, preparation vessel 600 may be inserted into housing 110 and the door of housing 110 may be closed and latched. As discussed above, closing and latching the door of housing 110 may cause preparation vessel 600 to be forced into contact with interior walls of housing 110 such that optimized heat transfer between vessel 600 and housing 110 may be achieved. In some embodiments, attaching the preparation vessel may further comprise fluidly connecting one or more connectors, such as inlets 604, to establish a flow path for liquid and/or gas to enter the preparation vessel.

At block 1308, in some embodiments, attaching the disposable assembly may comprise attaching one or more sensors of the disposable assembly to the system or to one of the system components. For example, attaching the disposable assembly may comprise attaching a tube leading from an outlet of the preparation vessel to a flow sensor. In the example of sensor assembly 900, the tube may be attached to the slot of flow sensor 912 such that the sensor may monitor flow through the tube. Alternately or additionally, attaching the disposable assembly may comprise attaching a temperature sensor to the preparation vessel. In the example of sensor assembly 900, temperature sensor 914 may be adhered to an exterior surface of the preparation vessel such that it may monitor a temperature associated with the contents of the preparation vessel.

In addition to providing physical connections, attaching the disposable assembly to the system may further comprise establishing electronic communicative connections such that one or more sensors of the disposable assembly may send data to electronic and control components of the system. In the example of sensor assembly 900, connector 904 may be plugged into an electronic data interface of system 100 in order to send data from the flow sensor and/or the temperature sensor to system 100.

At block 1310, in some embodiments, attaching the disposable assembly may comprise attaching one or more components of the disposable assembly by hand and/or without the use of tools. For example, components of the disposable assembly may be configured to be able to be attached and removed with threads, Luer-style connectors, latches, plugs, and other connection mechanisms that are configured to be operated by hand. In this way, the disposable assembly may be able to be used without tools in a sterile environment, which may increase usability due to the space taken up by tools and the fact that tools may be contaminated and unable to be used in a sterile environment.

At block 1312, in some embodiments, the system may perform an integrity test. In some embodiments, the integrity test is an integrity test for testing the integrity of one or more components of the recently-attached disposable assembly. For example, the integrity test may be performed to determine whether all components of the disposable assembly are physically, fluidly, and electronically connected in a predefined manner, such that the system may use one or more sensors to determine whether components are attached in the predefined manner and may provide an output to a user indicating whether or not they are.

Furthermore, the integrity test may be performed to determine whether one or more components of the disposable assembly are capable of maintaining internal gas pressure at an operating pressure of the system. As discussed above, an operating pressure of the system may be a pressure used to force fluid through a constriction cartridge. In some embodiments, testing pressurization integrity via an integrity test may comprise forcing pressurized gas into the preparation vessel and/or other portions of the flow path of the system and using one or more pressure sensors of the system to monitor the pressure. Once the system is pressurized to the operating pressure, the pressure sensor may monitor the pressure to ensure that the pressure is able to be maintained (e.g., without leaking) for a predetermined period of time. Once the system determines that the system is capable of maintaining the operating pressure, the system may provide an output to a user indicating that the system has passed the pressure integrity test. The system may then be depressurized.

In some embodiments, the predetermined amount of time may be about 10 seconds, 20 seconds, 30 seconds, 60 seconds, or 90 seconds. In some embodiments, an initial pressurization period of about 20 seconds may be followed by a pressure-maintaining period of about one minute. In some embodiments, the system may require that the pressure be successfully maintained within a range of about +/−1 psi, +/−5 psi, or +/−10 psi. In some embodiments, the range may be greater than +/−0.5 psi, +/−1 psi, +/−5 psi, or +/−10 psi. In some embodiments, the range may be less than +/−1 psi, +/−5 psi, +/−10 psi, or +/−15 psi.

In some embodiments, in the event that the system indicates failure of one or more components of an integrity test, the system may display an indication to a user as to what connections or components must be remedied or replaced. In some embodiments, a user may remove the defective disposable assembly and insert a replacement disposable assembly.

At block 1314, in some embodiments, primer solution may be passed through the disposable assembly. In some embodiments, passing primer solution (e.g., buffer fluid) through the assembly before passing the cell suspension through the system may help prevent cells of the cell suspension from sticking to and/or being damaged by the interior surfaces of the flow path of the system. In some embodiments, the primer solution passed through the system may originate at a buffer input bag, such as buffer input bag 108 in system 100.

In some embodiments, a user may provide a buffer input bag to the system in a same or similar manner as the user may provide a cell suspension input bag to the system, such as by suspending the bag from a hook and/or by fluidly connecting the bag to an inlet of the system (e.g., an inlet of a preparation vessel of the system) before performing an integrity check.

In some embodiments, the system may be configured to partially or fully automatically cause the primer solution to flow through the disposable assembly, including by providing and monitoring gas pressure to force the fluid along the flow path and/or by opening and closing valves, clamps, and/or ports accordingly. In some embodiments, the system may be configured to receive an input from a user (e.g., an input executed at a user interface device of the system, such as touch-screen 120 of system 100) and to responsively generate and transmit one or more electronic signals to cause components of the system to cause flow of the primer solution through the disposable assembly.

For example, the system may generate and transmit signals to a pressure control module of the system to pressurize gas in the preparation vessel of the system, such as by activating one or more gas pumps, opening one or more valves, and/or operating one or more regulators in order to cause pressurized gas to flow into the vessel to force the primer solution to flow through the disposable assembly. Additionally, the system may generate and transmit signals to one or more valves (e.g., solenoid valves), clamps, or other flow-control mechanisms disposed along the flow path of the system in order to open the flow path to allow the primer solution to flow through the disposable assembly. For example, any of the valves, clamps, or fittings shown in system 1000 in FIG. 10 may be configured to be electronically controlled to be actuated automatically by the system.

Furthermore, the system may monitor data generated by one or more sensors (e.g., flow sensor 912) to automatically determine when the primer solution has completed flowing through the disposable assembly, and to accordingly perform additional actions and/or notify a user that the priming process has completed.

In some embodiments, primer solution may flow into an output bag such as buffer output bag 114, and may then be removed and/or disposed by a user.

At block 1316, in some embodiments, the cell suspension may be passed into the preparation vessel. In some embodiments, the cell suspension may be passed into the preparation vessel after the primer solution has been passed out of the preparation vessel and through the remainder of the disposable assembly and into an output bag. In some embodiments, the system may be configured to partially or fully automatically cause the primer solution to flow out of the input bag and into the preparation vessel, including by controlling any one or more valves, clamps, pumps, regulators, or other pressure-control and/or flow-control mechanisms, in a same or similar manner as described above with reference to step 1314.

In some embodiments, the system may be configured to receive an input from a user (e.g., an input executed at a user interface device of the system, such as touch-screen 120 of system 100) and to responsively generate and transmit one or more electronic signals to cause components of the system to cause flow of the primer solution through the disposable assembly. In some embodiments, the system may be configured to automatically cause the cell suspension to enter the preparation vessel upon detecting completion of the primer process.

Furthermore, the system may monitor data generated by one or more sensors (e.g., a flow sensor) to automatically determine when the cell suspension has completed flowing into the preparation vessel, and to accordingly perform additional actions and/or notify a user that the process has completed.

At block 1318, in some embodiments, while the cell suspension is in the preparation vessel, the cell suspension may be prepared for passage through the constriction cartridge. In some embodiments, preparing the cell suspension for passage through the constriction cartridge may include taking one or more manual or automated actions to change (or to maintain) one or more properties of the cell suspension. For example, the cell suspension may in some embodiments be prepared for passage through the constriction cartridge by cooling the cell suspension, heating the cell suspension, agitating the cell suspension, and/or causing pressure to be applied to the cell suspension. In some embodiments, the preparation process may involve performing one of temperature control, pressure control, and/or agitation simultaneously, while in some embodiments it may involve performing one or more of them one after another. For example, the temperature control process may take significantly longer than the pressurization process, so the temperature control process may in some embodiments be performed before the pressurization process (e.g., the system may only begin pressurizing the vessel once the system determines that the cell suspension has reached a target temperature range). While discussion herein may contemplate performing the preparation processes simultaneously, they may be performed in some embodiments simultaneously and/or in any sequential order.

At block 1320, in some embodiments, preparing the cell suspension for passage through the constriction cartridge may comprise causing pressure to be applied to the cell suspension. As discussed above, pressurized gas may be used to apply pressure to liquid in a flow path of the system to force the liquid to flow along the flow path. In some embodiments, when the cell suspension is sitting inside the preparation vessel, the space above the cell suspension in the preparation vessel may be filled with pressurized sterile gas in order to apply force to the liquid that may be used to force it toward the outlet at the bottom of the preparation vessel. In the example of system 100, preparation vessel 600 may be partially filled with the cell suspension, and pressurized sterile gas such as nitrogen may then be caused to flow into the vessel through one of vessel inlets 604. In the example of system 1000, pressurized gas may flow into vessel 1016 through connector 1052 in order to cause pressure to be applied to the cell suspension in the vessel.

In some embodiments, the system may be configured to receive an input from a user (e.g., an input executed at a user interface device of the system, such as touch-screen 120 of system 100) and to responsively generate and transmit one or more electronic signals to cause components of the system to cause pressurization of gas inside the preparation vessel. In some embodiments, the system may be configured to automatically cause pressurization of gas inside the preparation vessel upon detecting that the cell suspension has completely flowed into the vessel.

In some embodiments, the system may be configured to partially or fully automatically cause pressurization of gas inside the preparation vessel, including by controlling any one or more valves, pumps, regulators, or other pressure-control mechanisms, in a same or similar manner as described above with reference to step 1314. In some embodiments, the system may monitor the pressure inside the preparation vessel or may monitor gas pressure at another location in a pressure control assembly in order to determine whether the pressure inside the preparation vessel needs to be increased, decreased, or maintained in order to achieve a desired operating pressure. In some embodiments, the system may use a pump to increase pressure to a desired pressure (e.g., operating pressure) from a low pressure source. In some embodiments, the operating pressure may be about 20 psi, about 30 psi, about 50 psi, about 70 psi, about 90 psi, about 110 psi, or about 130 psi. In some embodiments, the operating pressure may be greater than 10 psi, 20 psi, 50 psi, 70 psi, 90 psi, 110 psi, or 130 psi. In some embodiments, the operating pressure may be less than 20 psi, 50 psi, 70 psi, 90 psi, 110 psi, 130 psi, or 150 psi.

While block 1320 above contemplates causing pressure to be applied to the cell suspension, alternate or additional techniques may in some embodiments be used to cause flow of the cell suspension out of a preparation vessel and/or to and through a constriction cartridge. For example, in some embodiments, alternately or in addition to pressurization of gas in a preparation vessel, the cell suspension may be caused to flow out of the preparation vessel and/or to and through a constriction cartridge by gravity, by vacuum force, by centrifugation, and/or by force applied by a pump.

At block 1322, in some embodiments, preparing the cell suspension for passage through the constriction cartridge may comprise agitating the cell suspension. In some embodiments, agitating the cell suspension may ensure even distribution of the cells throughout the suspension and prevent the cells from becoming unevenly distributed in the cell suspension before the suspension is passed through the constriction cartridge. In some embodiments, the agitation may be achieved by causing the preparation vessel to shake or vibrate. In the example of system 100, preparation vessel 600 may be agitated due to shaking of shaker plate 304 as shown in FIG. 3. In some embodiments, a user may be able to set an agitation rate, intensity, and/or duration. In some embodiments, the system may automatically determine and/or set an agitation rate, intensity, and/or duration. In some embodiments, a user may be able to select whether or not agitation is used as part of the cell suspension preparation process.

In some embodiments, the system may be configured to receive an input from a user (e.g., an input executed at a user interface device of the system, such as touch-screen 120 of system 100) and to responsively generate and transmit one or more electronic signals to cause components of the system to agitate the cell suspension inside the preparation vessel. In some embodiments, the system may be configured to automatically cause agitation of the cell suspension inside the preparation vessel upon detecting that the cell suspension has completely flowed into the vessel.

In some embodiments, the system may be configured to partially or fully automatically cause agitation of the cell suspension inside the preparation vessel, including by controlling any one or more shaker plates, vibrating devices, stirring devices, sonic agitation devices, peristaltic pump devices, gas/diaphragm devices, or other mechanisms configured to cause shaking/vibration of the preparation vessel and/or agitation/circulation of the cell suspension inside the vessel. In some embodiments, methods other than agitation may be used to prevent the cells from falling out of suspension, to re-suspend the cells, and/or to homogenize the cell suspension, such as segmented intake (e.g., a small aliquot of input may be added over time to keep the cells in suspension). In the example of system 100, the system may be configured to automatically electronically control motor 302 and/or belt drive 306 in order to control the shaking of shaker plate 304.

At block 1324, in some embodiments, preparing the cell suspension for passage through the constriction cartridge may comprise controlling a temperature of the cell suspension. In some embodiments, controlling a temperature of the cell suspension may comprise cooling the cell suspension, heating the cell suspension, or ensuring that a temperature of the cell suspension remains unchanged. In some embodiments, the payload delivery process may be most effective at a specific predetermined temperature or temperature range, and the system may therefore be configured to be able to heat or cool the cell suspension to that predetermined temperature or temperature range before causing the suspension to flow through the constriction cartridge. In some embodiments, the system may be configured such that the cell suspension is heated and/or cooled to have a temperature greater than about 0, 1, 2, 3, 4, 5, 10, 20, 30, 35, 37, or 40 degrees Celsius. In some embodiments, the system may be configured such that the cell suspension is heated and/or cooled to have a temperature less than about 1, 2, 3, 4, 5, 10, 20, 30, 35, 37, 40, or 45 degrees Celsius. In some embodiments, the system may be configured to bring the cell suspension from room temperature or storage temperature to the target temperature range within 30 minutes or less, 60 minutes or less, 90 minutes or less, or 120 minutes or less. In some embodiments, the system may be configured to operate at room temperature. In some embodiments, the system may be configured to operate between about 22 and 24 degrees Celsius, between about 21 and 25 degrees Celsius, between about 20 and 26 degrees Celsius, or between about 18 and 28 degrees Celsius.

In some embodiments, the system may be configured to receive an input from a user (e.g., an input executed at a user interface device of the system, such as touch-screen 120 of system 100) and to responsively generate and transmit one or more electronic signals to cause components of the system to adjust a temperature of the cell suspension inside the preparation vessel. In some embodiments, the system may be configured to automatically adjust a temperature of the cell suspension inside the preparation vessel upon detecting that the cell suspension has completely flowed into the vessel.

In some embodiments, the system may be configured to partially or fully automatically adjust a temperature of the cell suspension inside the preparation vessel, including by controlling any one or more suitable heating device or cooling device, optionally in conjunction with any suitable temperature sensor as discussed elsewhere herein. In some embodiments a temperature control device may comprise one or more forced-air heaters, one or more forced-air coolers, one or more thermoelectric cooling devices (e.g., Peltier coolers), one or more resistive heating devices, or the like. In the example of system 100, a temperature control device may be a part of temperature control module 118. In some embodiments, a temperature control device of the system may be in physical contact with a preparation vessel housing, such as preparation vessel housing 110, or the temperature control device may be otherwise configured to heat and/or cool the preparation vessel housing. By heating and/or cooling the preparation vessel housing while the preparation vessel is contained in the housing, heat may be transferred to or from the preparation vessel, and in turn to or from the cell suspension inside the preparation vessel, thereby achieving heating and/or cooling of the cell suspension.

In some embodiments, in order to achieve a predetermined target temperature, the system may be configured to continuously monitor a temperature of the cell suspension while the temperature control process is ongoing. For example, system 100 may be configured to continuously monitor a temperature associated with the cell suspension via temperature sensor 914, which may be adhered to an exterior surface of preparation vessel 600. Temperature sensor 914 may send data to temperature control module 118 and/or one or more other processors of system 100, and system 100 may determine on the basis of the data received whether the target temperature has been achieved, whether the temperature control process needs to continue, and whether a heating or cooling device being used in the temperature control process needs to be adjusted (e.g., to a higher temperature or to a lower temperature).

In some embodiments, one or more temperature sensors of the system may be configured to read both a PID (proportional-integral-derivative) temperature and an NTC (negative temperature coefficient) temperature, and to calculate, on the basis of both of those readings, an effective temperature. The system may determine whether the calculated effective temperature falls within a target temperature range. In the event that the effective temperature does not fall within the target temperature range, the system may adjust one or more heating or cooling elements and/or may wait for a predetermined amount of time before calculating a new effective temperature based on new PID and NTC temperature readings and checking whether the new effective temperature falls within a target range. When it is determined that the effective temperature falls within the target range, then the system may indicate to a user that the temperature control process is complete and/or may conclude the temperature adjustment process. In some embodiments, if a predetermined amount of time passes and the effective temperature still has not reached the target temperature range, then the system may return a time-out error and may indicate to the user that the temperature control process has failed.

In some embodiments, rather than heating or cooling the cell suspension as part of the preparation process inside the preparation vessel, the cell suspension may instead be heated or cooled before entering the preparation vessel. For example, the cell suspension may in some embodiments be heated or cooled while inside an input bag or in another portion of a flow path upstream of a preparation vessel. Alternately or additionally, the cell suspension may in some embodiments be heated or cooled to a target temperature range as part of a batch temperature-control process where a large volume of cell suspension, suitable for use in multiple payload delivery processes, is heated or cooled at once. By heating or cooling cell suspension in a large batch volume, overall throughput time for multiple payload delivery processes may be improved as time may be saved by not needing to individually (and sequentially) heat or cool each small batch of cell suspension. In some embodiments, heating or cooling may be performed both before the cell suspension arrives at the preparation vessel and during the time in which the cell suspension is in the preparation vessel; for example, large adjustments to suspension temperature may be made before the preparation vessel while fine adjustments to temperature may be performed while the suspension is in the preparation vessel.

At step 1326, in some embodiments, the payload may be caused to come into contact with the cell suspension while the cell suspension is in the preparation vessel. In some embodiments, the payload may include one or more peptides, nucleic acids, proteins, carbohydrates, lipids, small molecules, complexes, and/or nanomaterials, which may be included as part of a suspension. In some embodiments, this may occur before, during, or after any one or more of the cell suspension preparation steps discussed above with respect to steps 1318-1324. In any event, it should be noted that, in some embodiments, the payload may be caused to come into contact with the cell suspension before the cell suspension is passed through the constriction cartridge. On the other hand, in some embodiments such as those discussed below with reference to step 1330, the payload may be caused to come into contact with the cell suspension only after the cell suspension is passed through the constriction cartridge. In embodiments where the payload is mixed with the cell suspension before passage through the constriction cartridge, the payload may be passed through the constriction cartridge along with the cell suspension.

In some embodiments in which the payload is caused to come into contact with cell suspension while in the preparation vessel, the payload may be mixed in as part of the cell suspension in the input bag, or the payload may be separately inserted into the preparation vessel through an inlet to the preparation vessel. In some embodiments, the payload may be provided in a dedicated input bag and may flow into the preparation vessel and mix with the cell suspension. In any of these embodiments, flow of the payload through the system may be electronically controlled by the system (e.g., by automatically opening valves, applying pressure, etc.) in any of the same ways as discussed above with respect to controlling the flow of the cell suspension itself.

At step 1328, in some embodiments, the cell suspension may be passed through the constriction cartridge. As discussed elsewhere herein, the cell suspension may be forced under pressure to flow through the constriction cartridge, which may cause the cell suspension to flow through one or more cell-constricting microfluidic channels and/or one or more cell-constricting filters. When cells of the cell suspension are forced through the constrictions of the cell-constricting microfluidic channels and/or cell-constricting filters, the cell membranes may be perturbed, and the perturbation may facilitate entry of the payload into the cell.

In some embodiments, the system may be configured to partially or fully automatically cause the cell suspension to flow out of the preparation vessel and into and through the constriction cartridge, including by controlling any one or more valves, clamps, pumps, regulators, or other pressure-control and/or flow-control mechanisms, in a same or similar manner as described above with reference to step 1314. In some embodiments, gas inside the preparation vessel has been pressurized, the system may electronically open an outlet of the preparation vessel in order to allow the gas pressure to force the cell suspension to flow out of the preparation vessel. In the example of system 100, a valve associated with outlet 606 may be opened. In the example of system 1000, a valve associated with connector 1018 may be opened.

In some embodiments, the system may be configured to receive an input from a user (e.g., an input executed at a user interface device of the system, such as touch-screen 120 of system 100) and to responsively generate and transmit one or more electronic signals to cause components of the system to cause flow of the cell suspension out of the cell preparation vessel and into and through the constriction cartridge. In some embodiments, the system may be configured to automatically cause flow of the cell suspension out of the cell preparation vessel and into and through the constriction cartridge upon detecting completion of the primer cell suspension preparation process. In some embodiments, the system may be configured such that the cell suspension is caused to flow into and through the constriction cartridge over a period of about 30 seconds, 1 minute, 2 minutes, or 3 minutes. In some embodiments, the period may be greater than 10 seconds, 30 seconds, 1 minute, 2 minutes, or 3 minutes. In some embodiments, the period may be less than about 30 seconds, 1 minute, 2 minutes, 3 minutes, or 5 minutes. In some embodiments, the systems and techniques disclosed herein may enable passing up to about 1 billion cells per minute, 1.5 billion cells per minute, or 2 billion cells or more per minute through a constriction cartridge.

Furthermore, the system may monitor data generated by one or more sensors (e.g., a flow sensor) to automatically determine when the cell suspension has completed flowing into and through the constriction cartridge, and to accordingly perform additional actions and/or notify a user that the process has completed. In the example of system 100, flow sensor 912 may be configured to optically monitor a tube extending from preparation vessel 600 to a constriction cartridge to determine when flow of the cell suspension through the tube has ceased.

At step 1330, in some embodiments, the payload may be caused to come into contact with the cell suspension following passage of the cell suspension through the constriction cartridge. As discussed above with respect to step 1326, the payload may in some embodiments be caused to come into contact with the cell suspension before the cell suspension is passed through the constriction cartridge. On the other hand, in some other embodiments, the payload may be caused to come into contact with the cell suspension only after the cell suspension is passed through the constriction cartridge. In some embodiments, the payload may effectively enter cells of the cell suspension even when they are only brought into contact after the cell suspension has passed through the constriction cartridge; that is, the perturbations caused to the cell membranes may enable effective payload entry for a period of time after the perturbations have been induced by a constriction.

In some embodiments in which the payload is caused to come into contact with the cell suspension only after the cell suspension is passed through the constriction cartridge, an independent source of payload suspension may be caused to flow into a same flow path, reservoir, or vessel as the cell suspension. For example, in some embodiments, the payload may be mixed in with the cell suspension during or after the cell suspension flows into an output bag such as output bag 112 of system 100. Thus, in some embodiments, some of the cell suspension may come into contact with the payload (e.g., in the output bag) after part of the suspension has flowed through the constriction cartridge, but this may occur while some of the cell suspension is still in the preparation vessel and/or has not yet flowed through the constriction cartridge. In any of these embodiments, flow of the payload through the system to come into contact with the cell suspension may be electronically controlled by the system (e.g., by automatically opening valves, applying pressure, etc.) in any of the same ways as discussed above with respect to controlling the flow of the cell suspension itself.

At step 1332, in some embodiments, the cell suspension may be passed into an output container. In the example of system 100, the output container may be output bag 112, which may be disconnected from system 100 and removed for further processing by a user after being filled.

In some embodiments, one or more computing devices of the intracellular payload-delivery system may monitor one or more characteristics or properties of the cell suspension during all or part of method 1300. In some embodiments, the system may monitor a time elapsed during all or part of method 1300, such as a time elapsed for a primer process, a time elapsed for an integrity check, a time elapsed for a cell suspension preparation process (e.g., cooling, air pressurization, etc.), a time elapsed for the cell suspension to flow through the constriction cartridge, a total time elapsed for the entire process, and/or a time elapsed for a combination of any two or more of any of the above. In some embodiments, the system may monitor a pressure of the system over time during any one or more portions of the overall process. In some embodiments, the system may monitor a temperature of the cell suspension over time during any one or more portions of the overall process.

In some embodiments, any of the characteristics or properties that are monitored may be stored as part of one or more log files or databases locally at the system; may be transmitted to remote electronic devices for storage, processing, or display; and/or may be displayed on a display (e.g., display 120 of system 100) at a local or remote electronic system.

User Interfaces

Figure 14A:
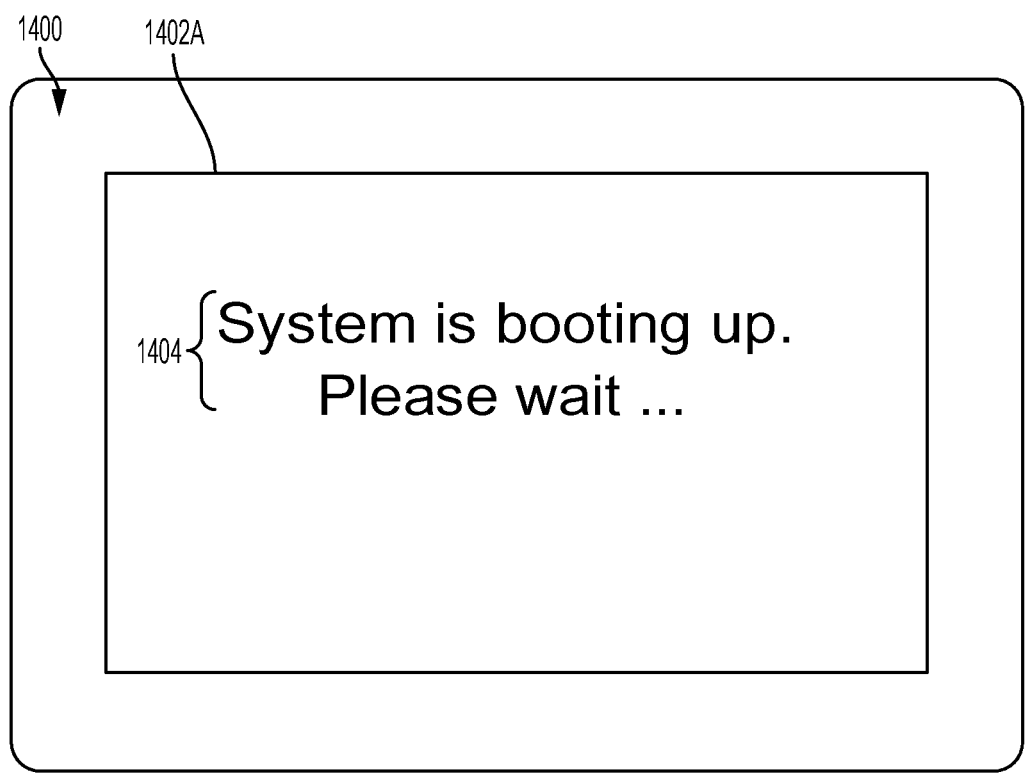
FIGS. 14A-14V illustrate user interfaces for controlling a tabletop system for delivering a payload to a cell, in accordance with some embodiments.
Figure 14B:
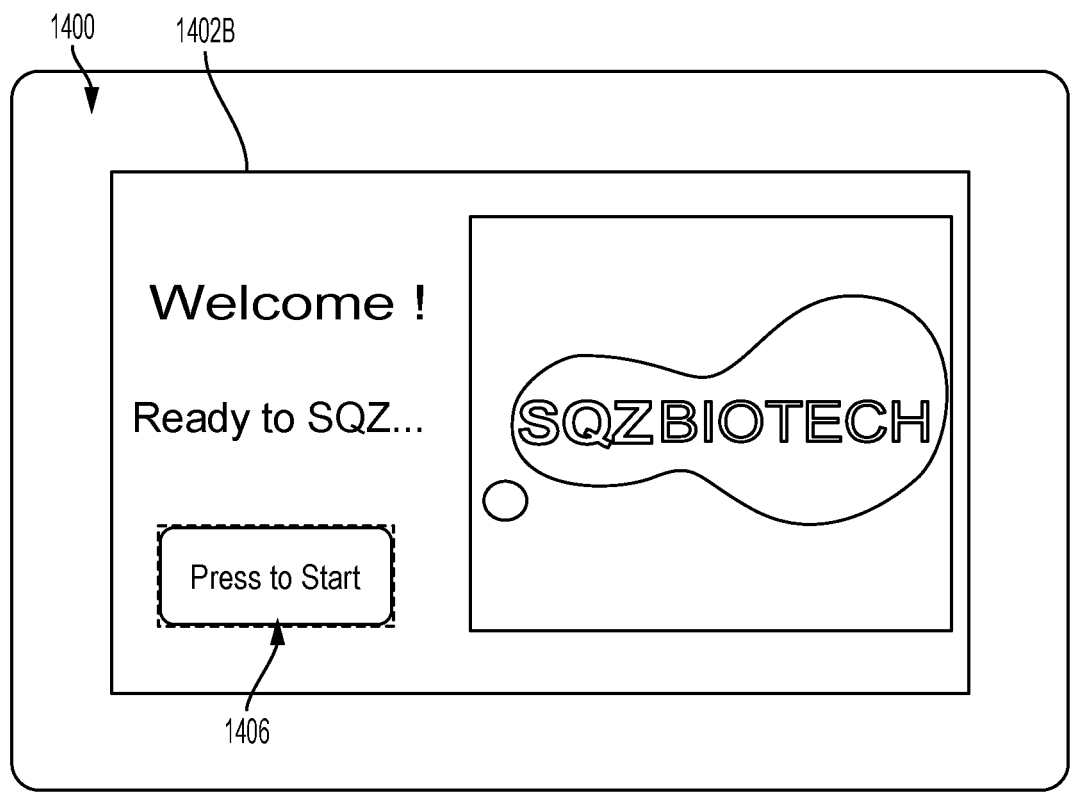
Figure 14C:
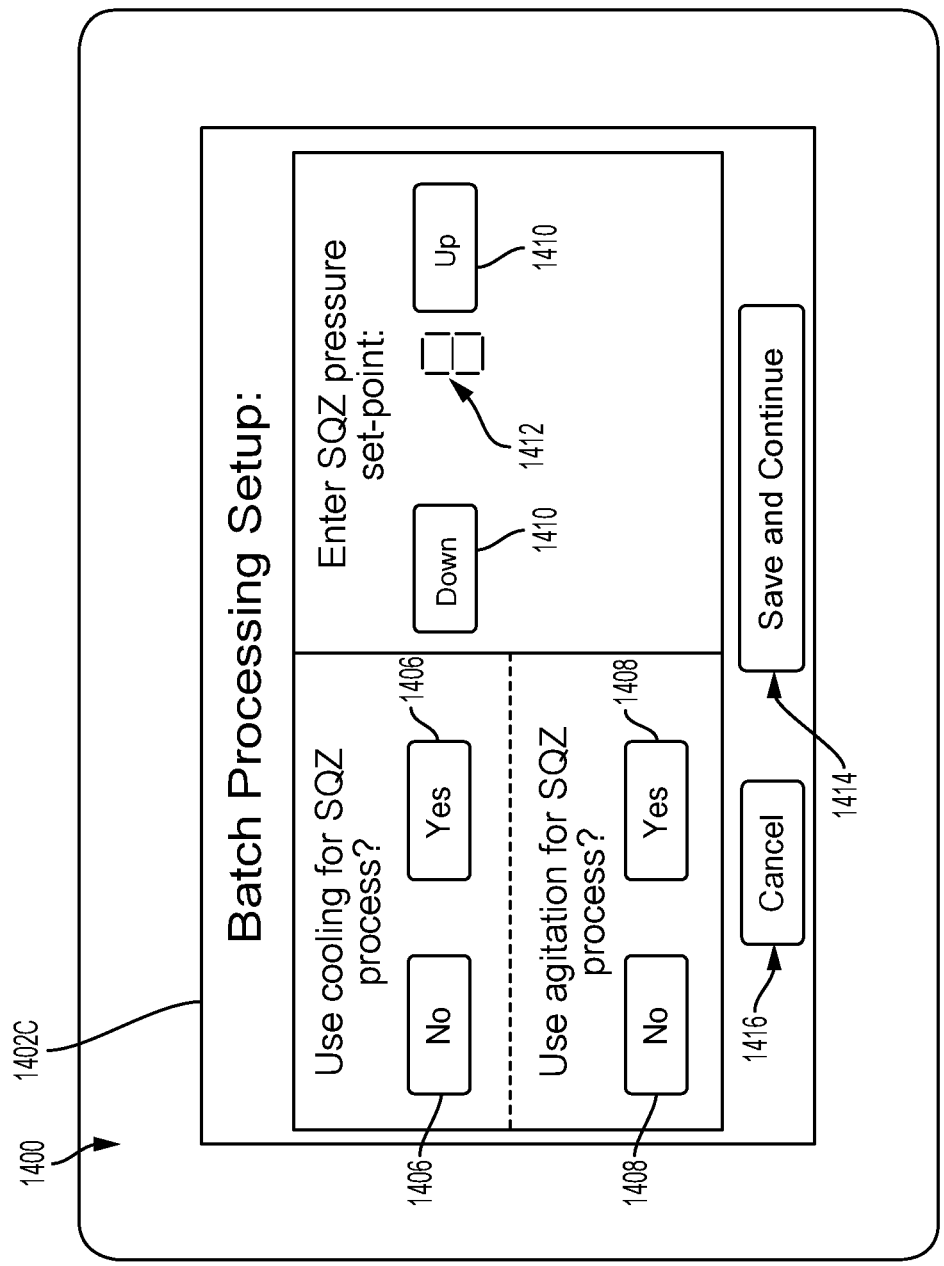
Figure 14D:
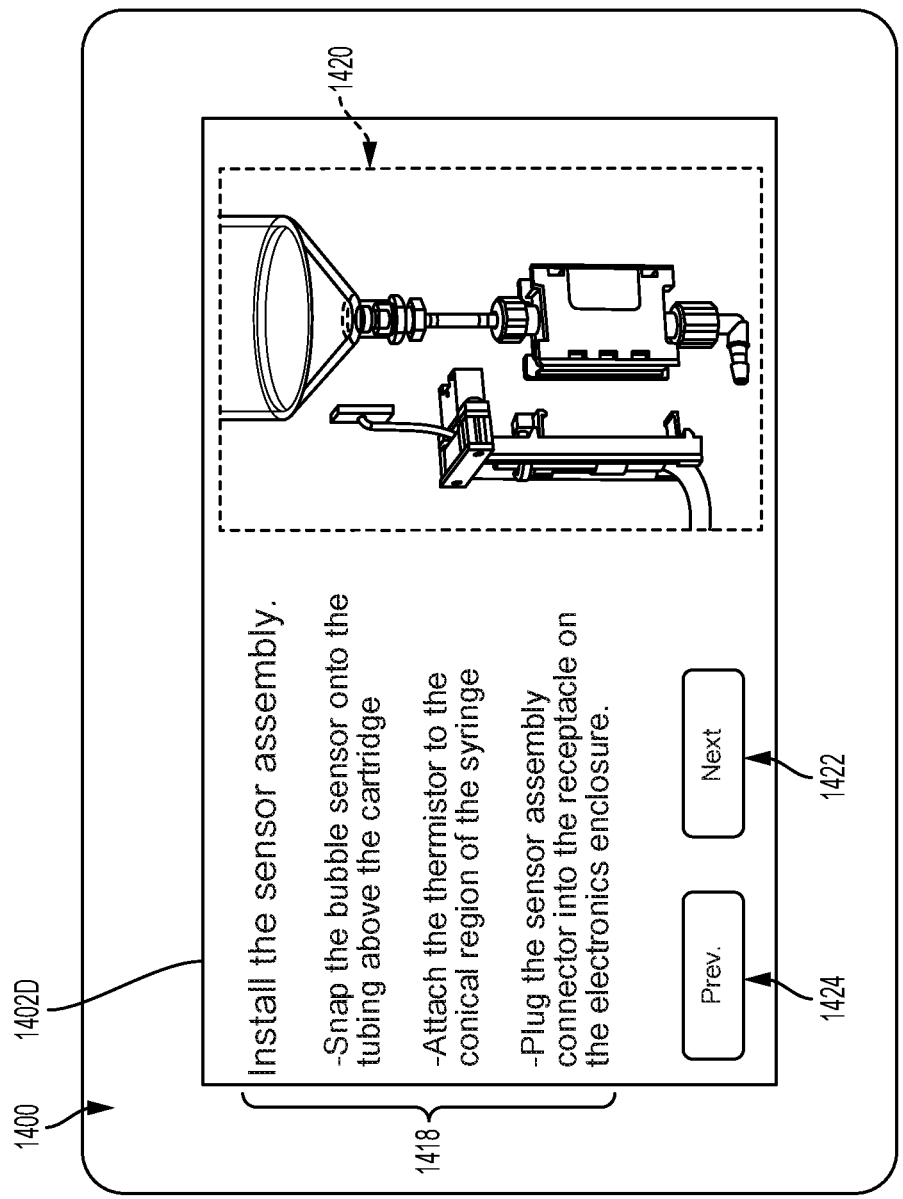
Figure 14E:
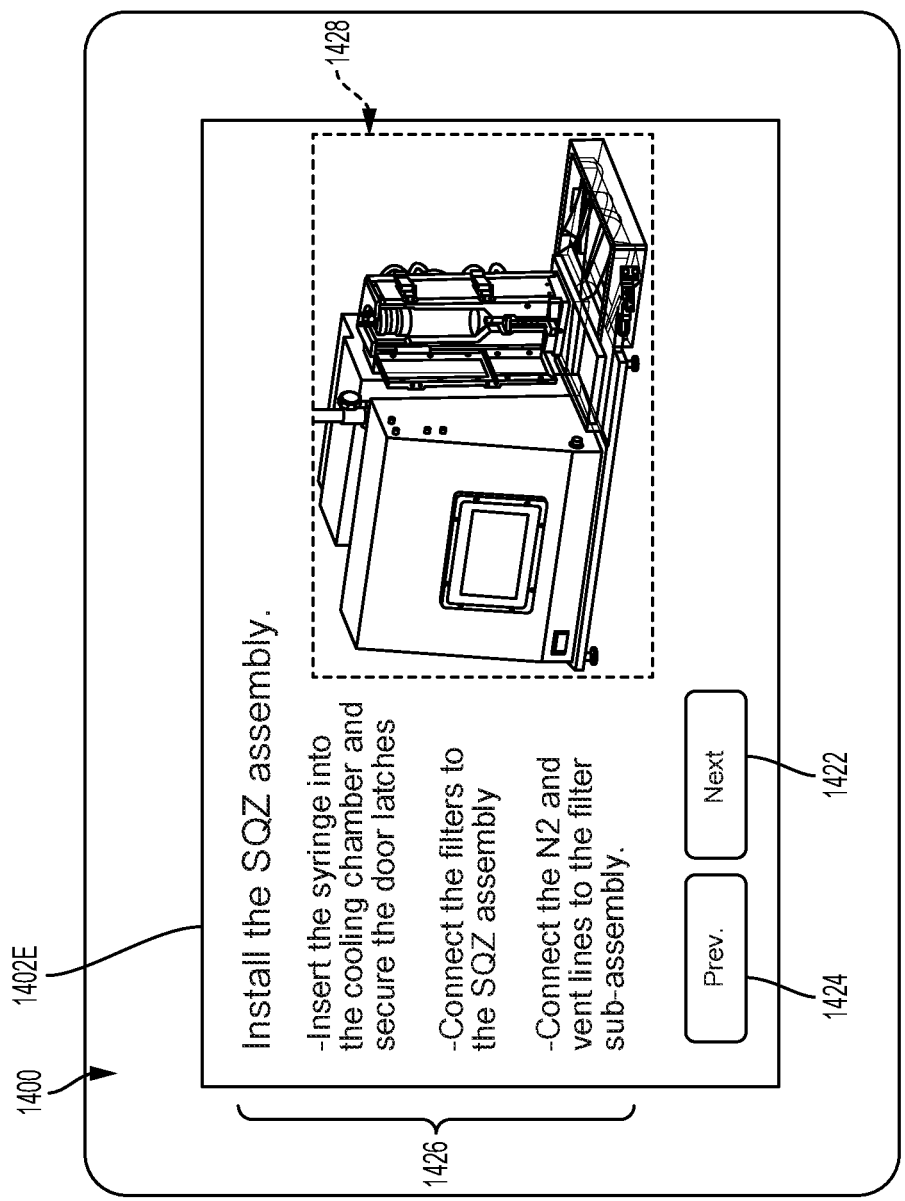
Figure 14F:
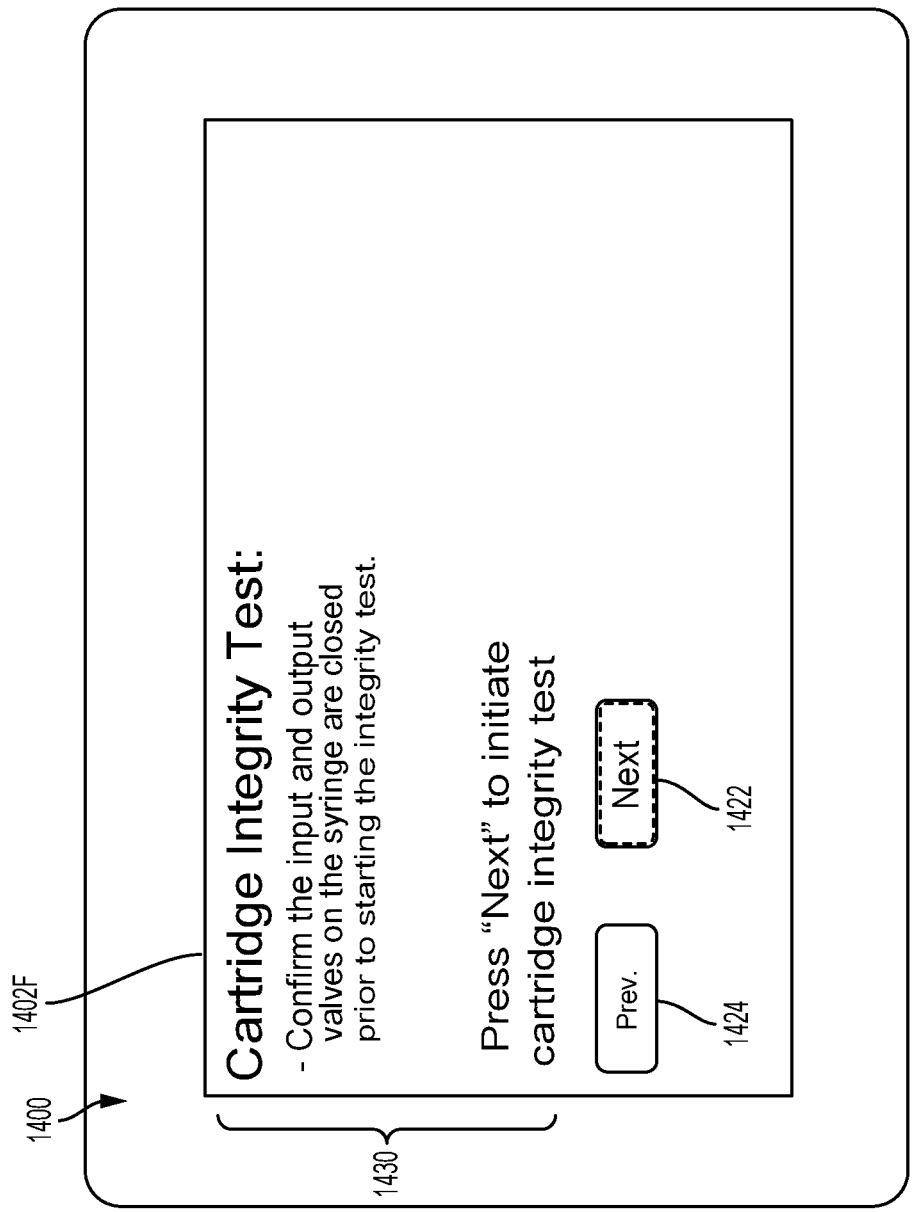
Figure 14G:
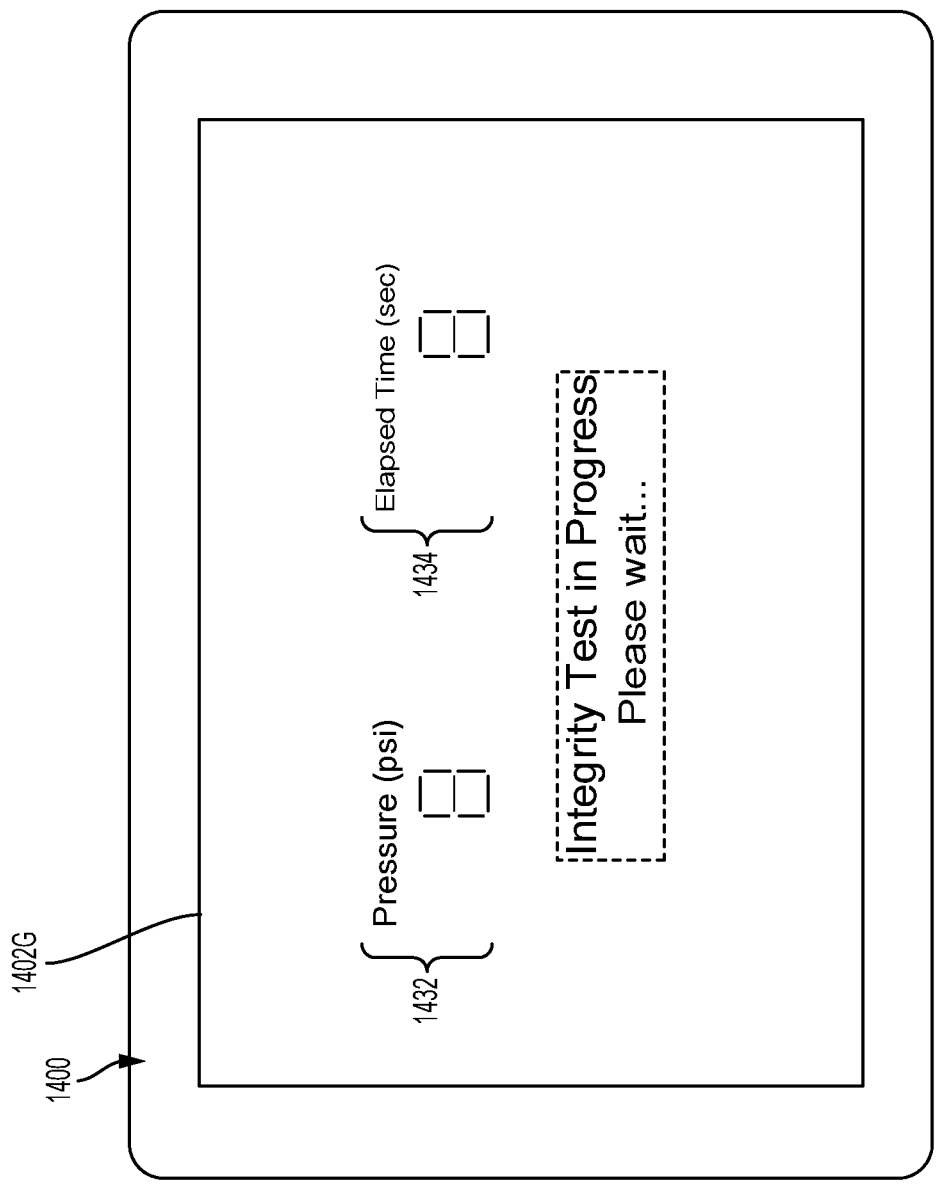
Figure 14H:
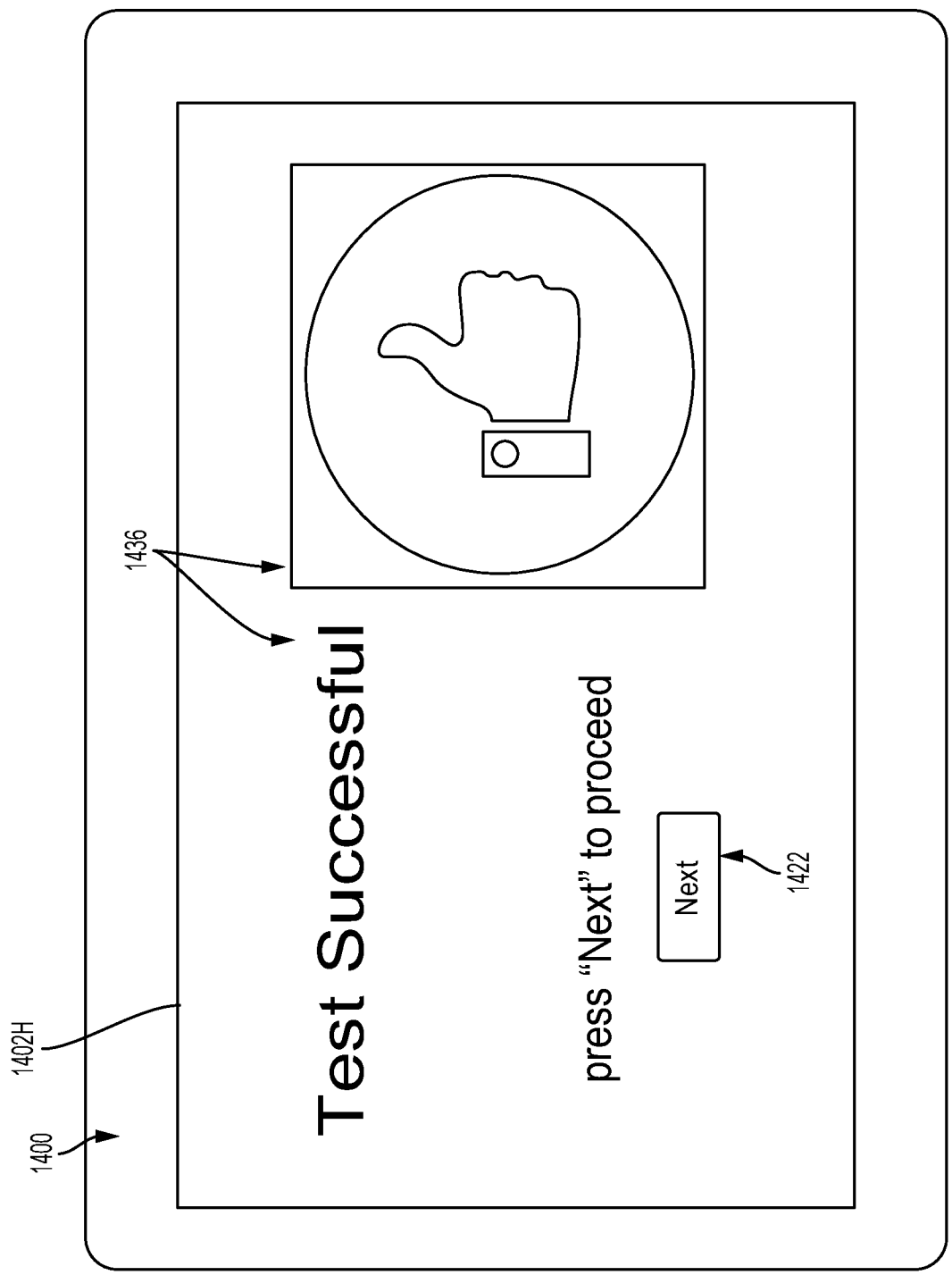
Figure 14I:
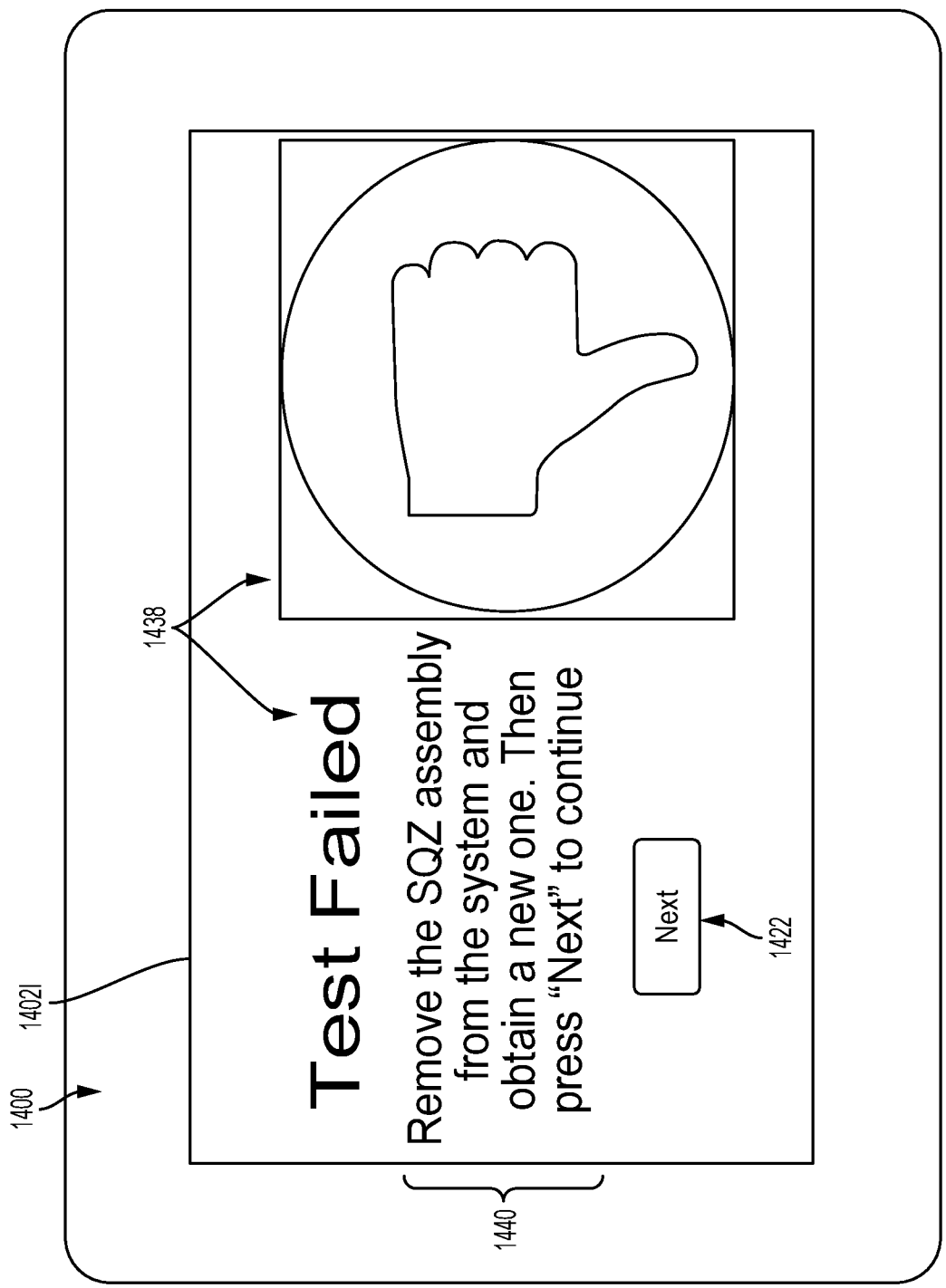
Figure 14J:
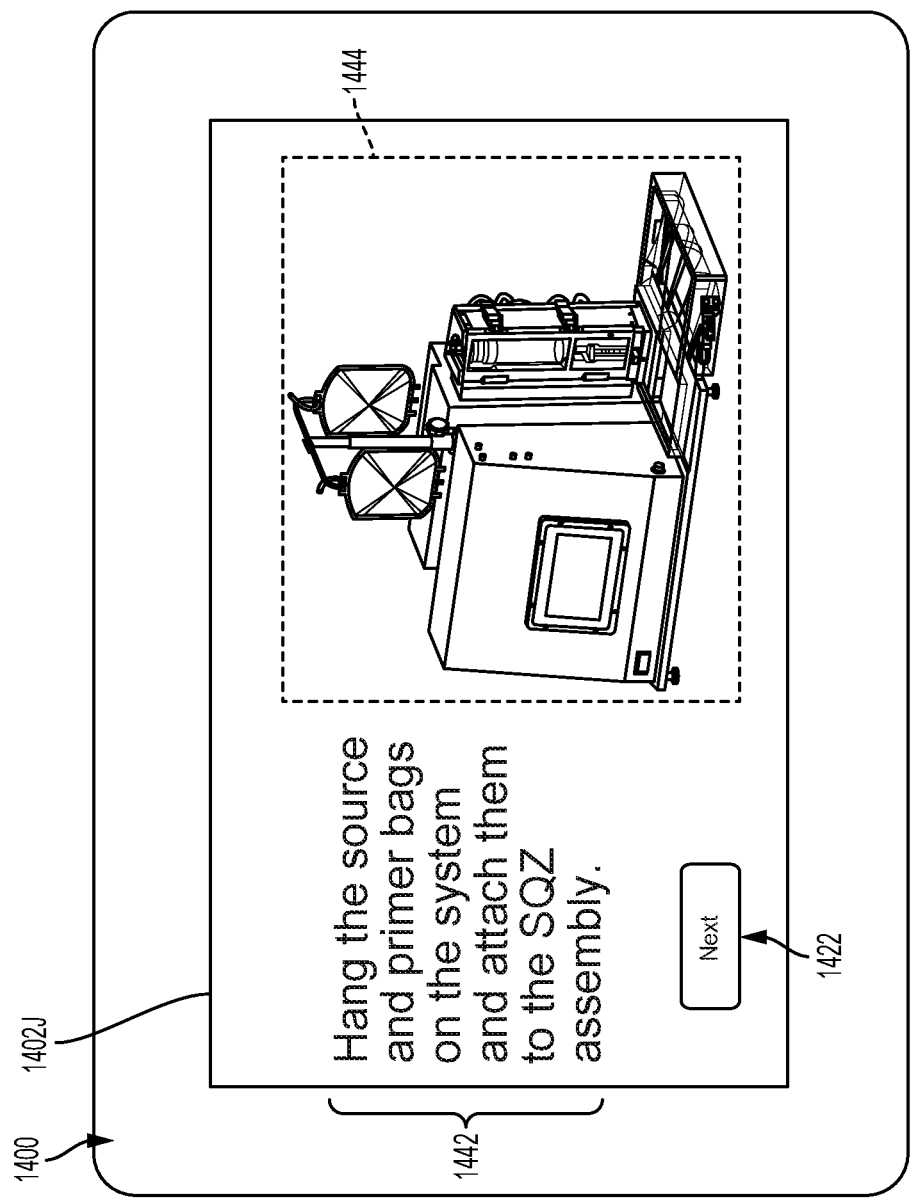
Figure 14K:
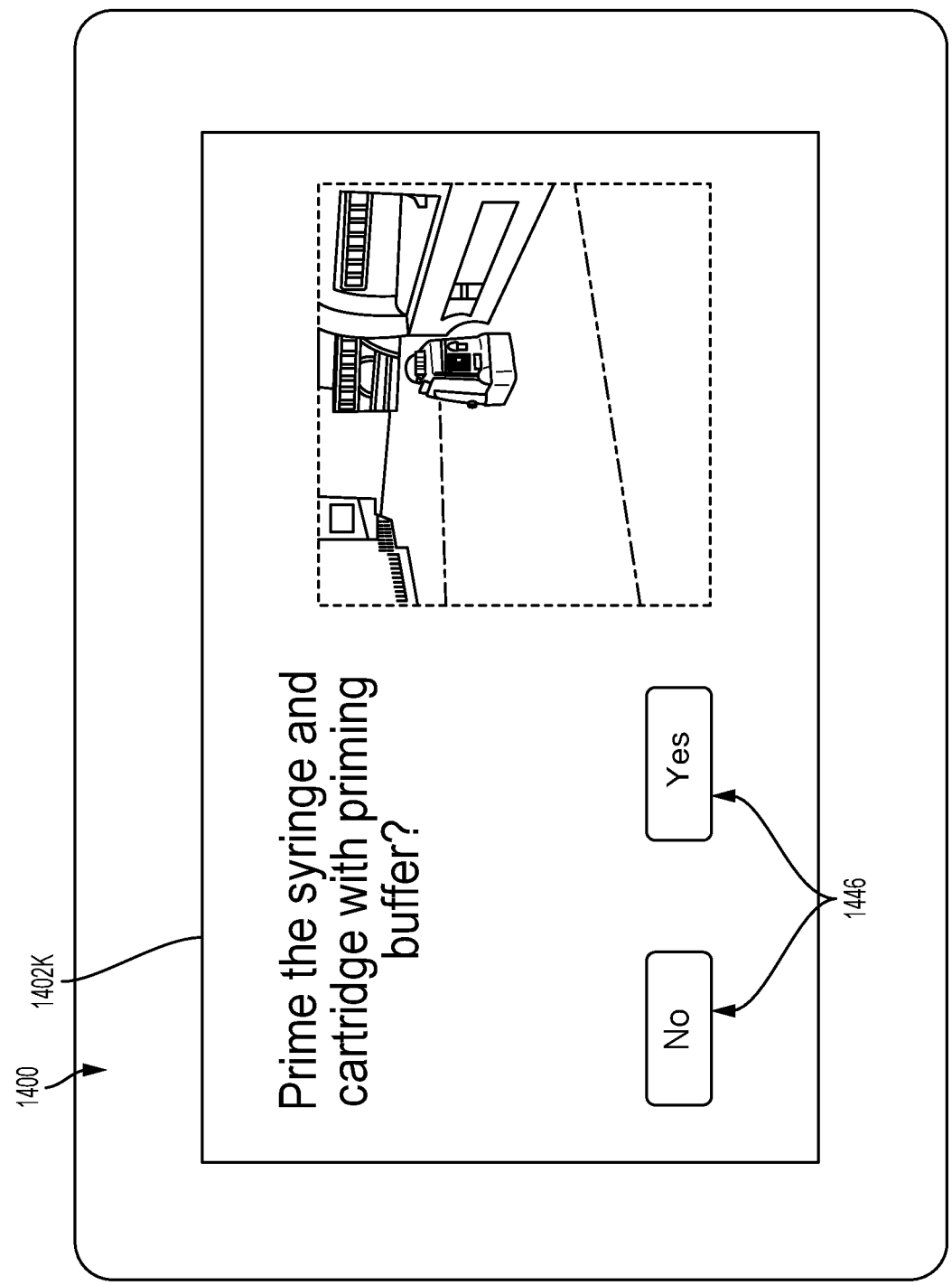
Figure 14L:
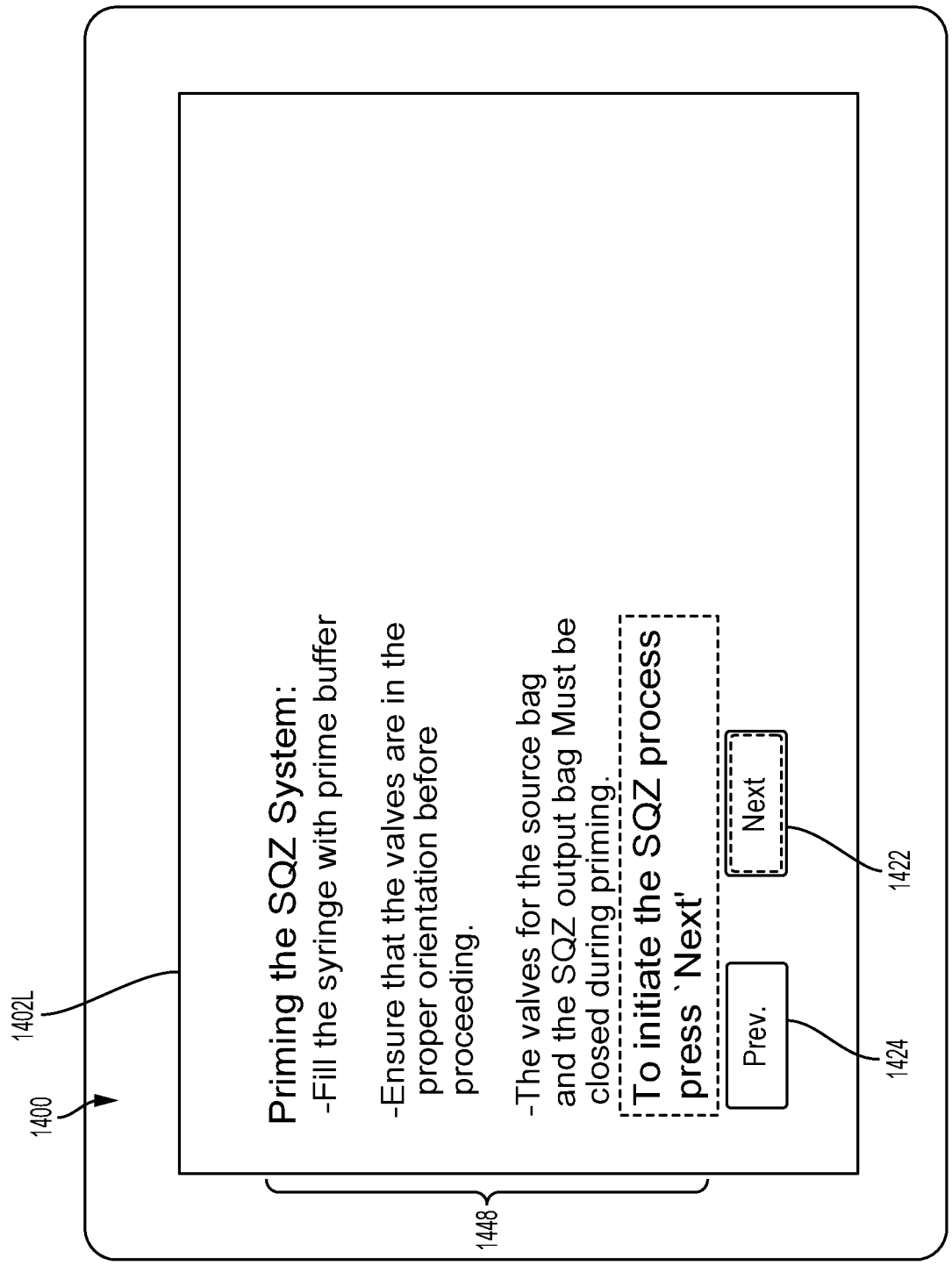
Figure 14M:
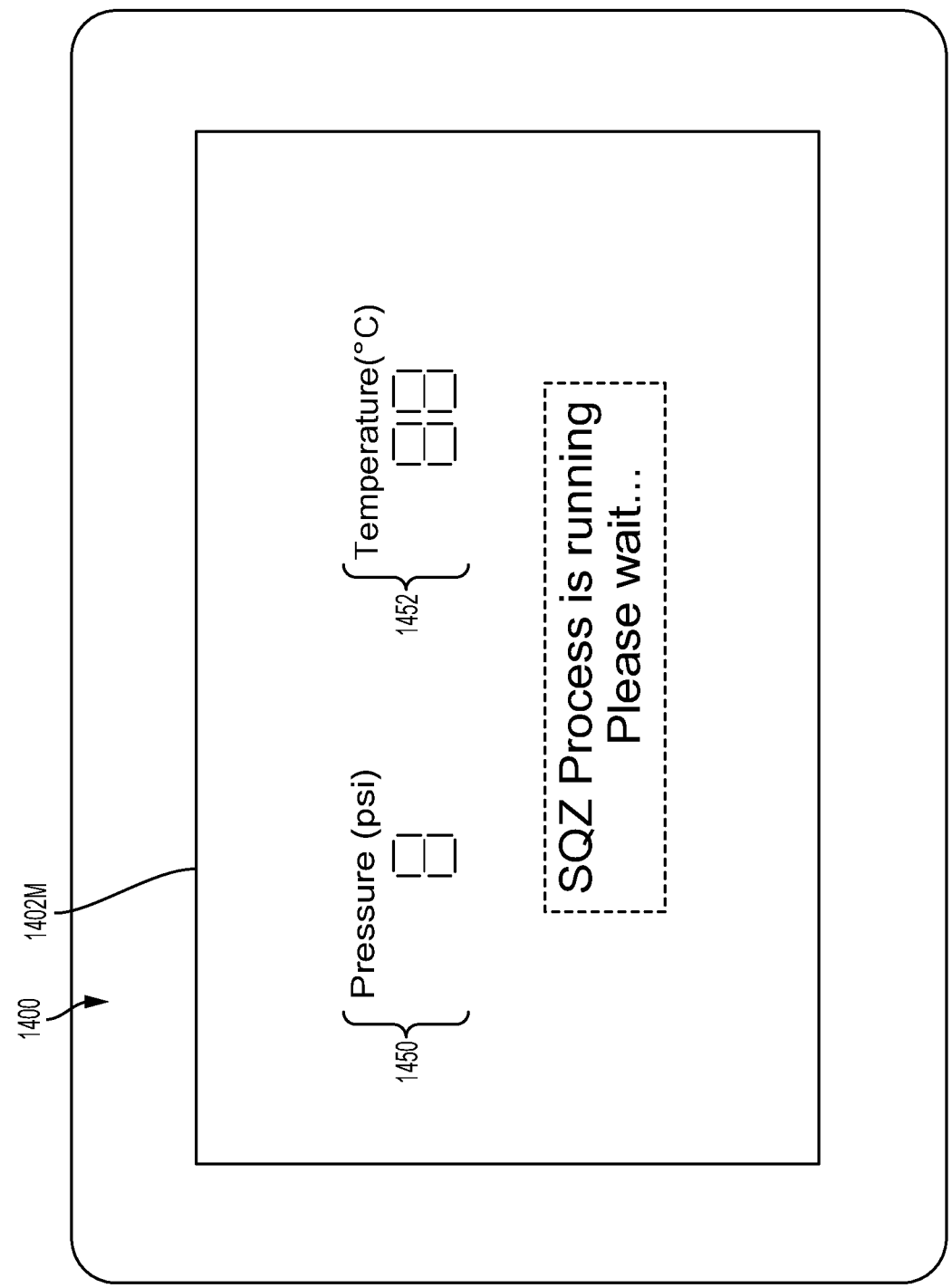
Figure 14N:
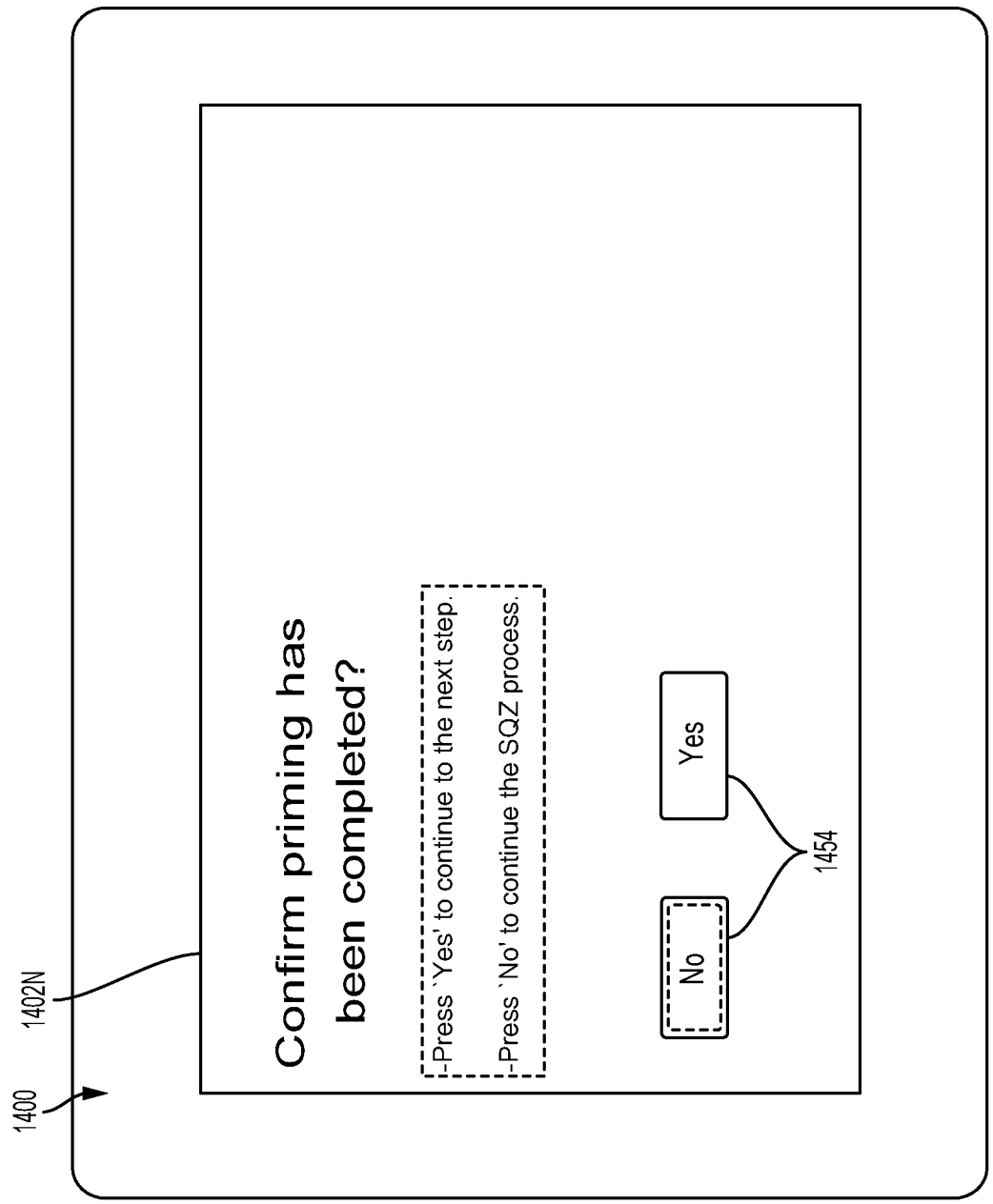
Figure 14O:
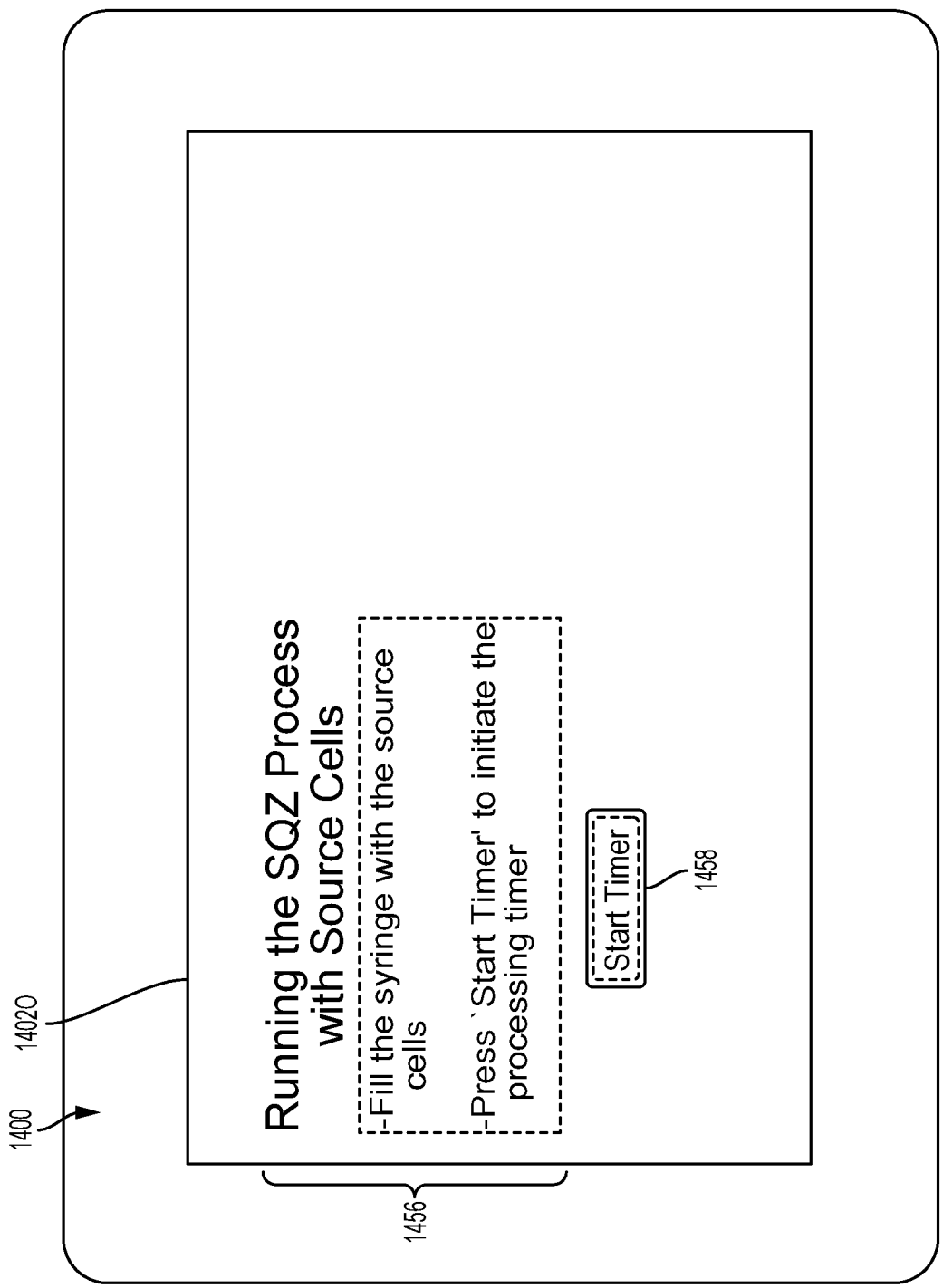
Figure 14P:
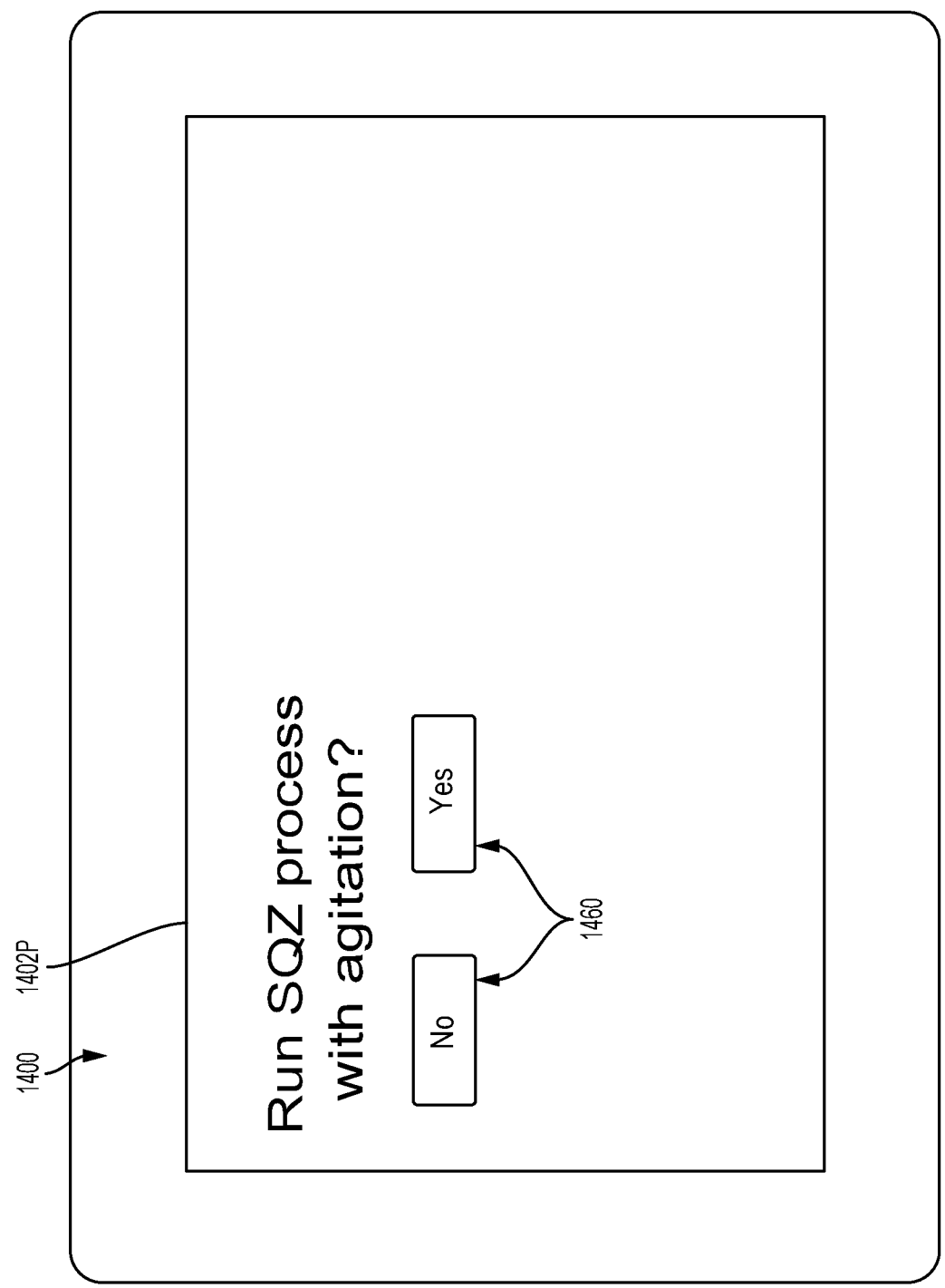
Figure 14Q:
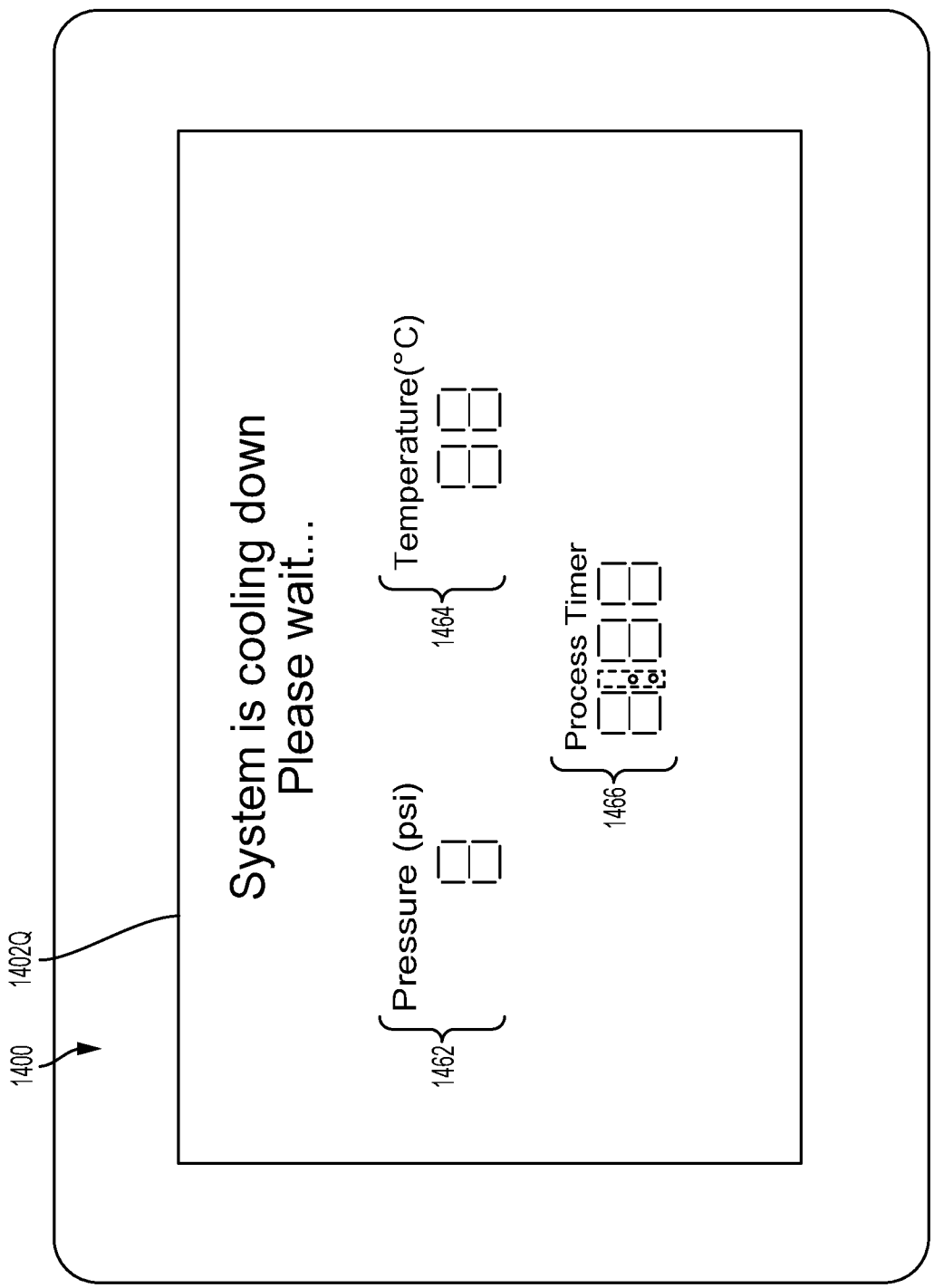
Figure 14R:
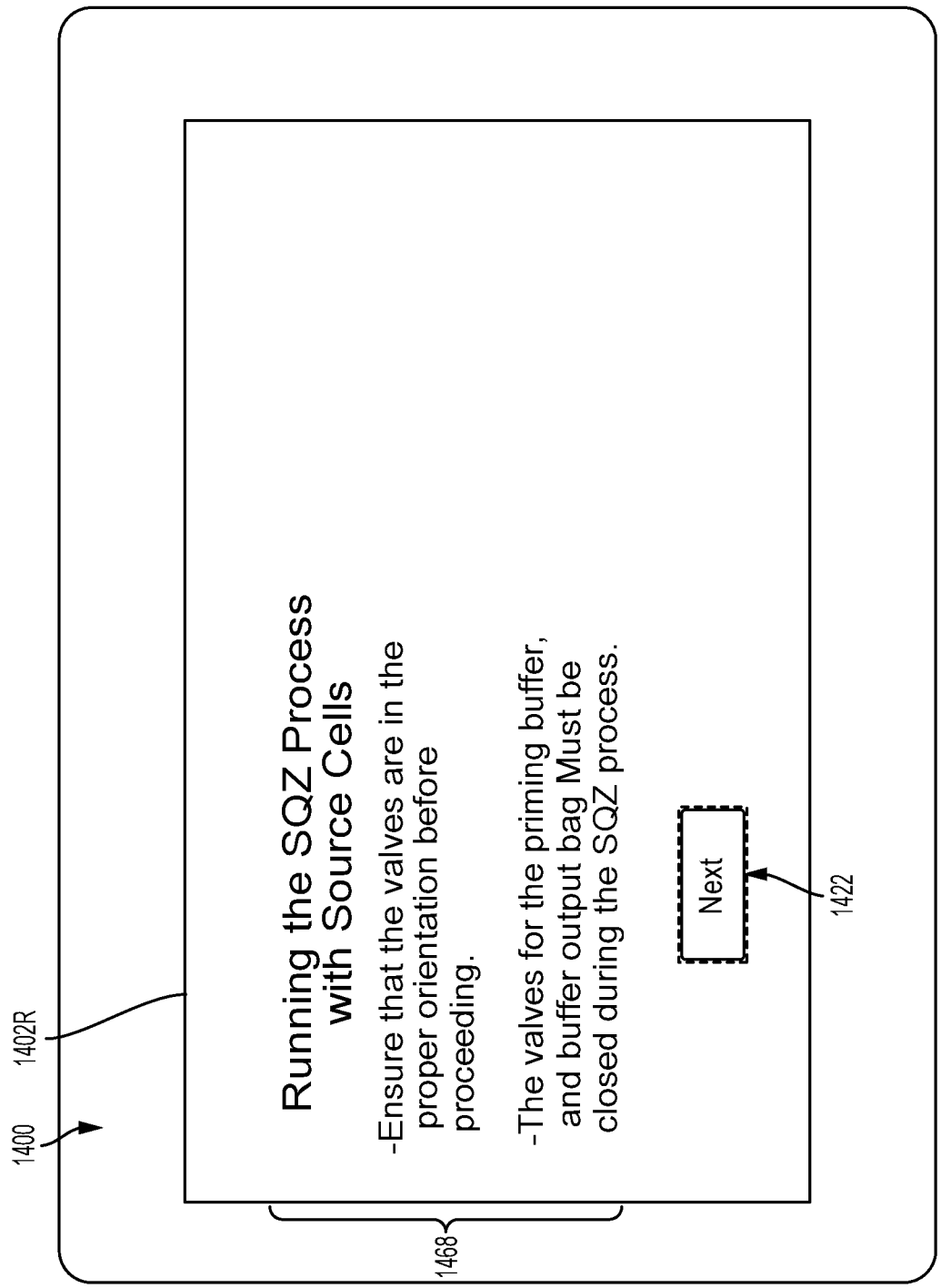
Figure 14S:
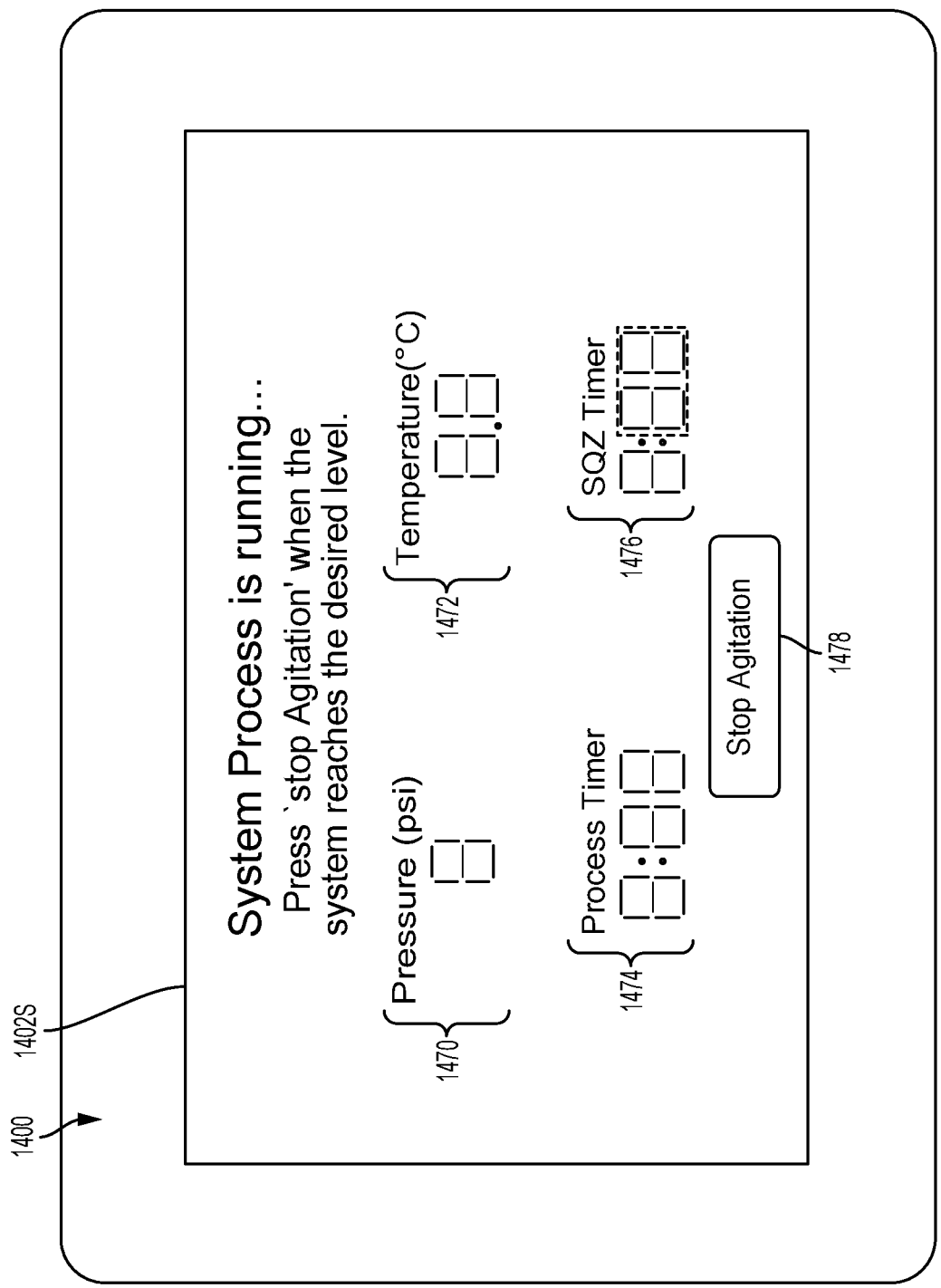
Figure 14T:
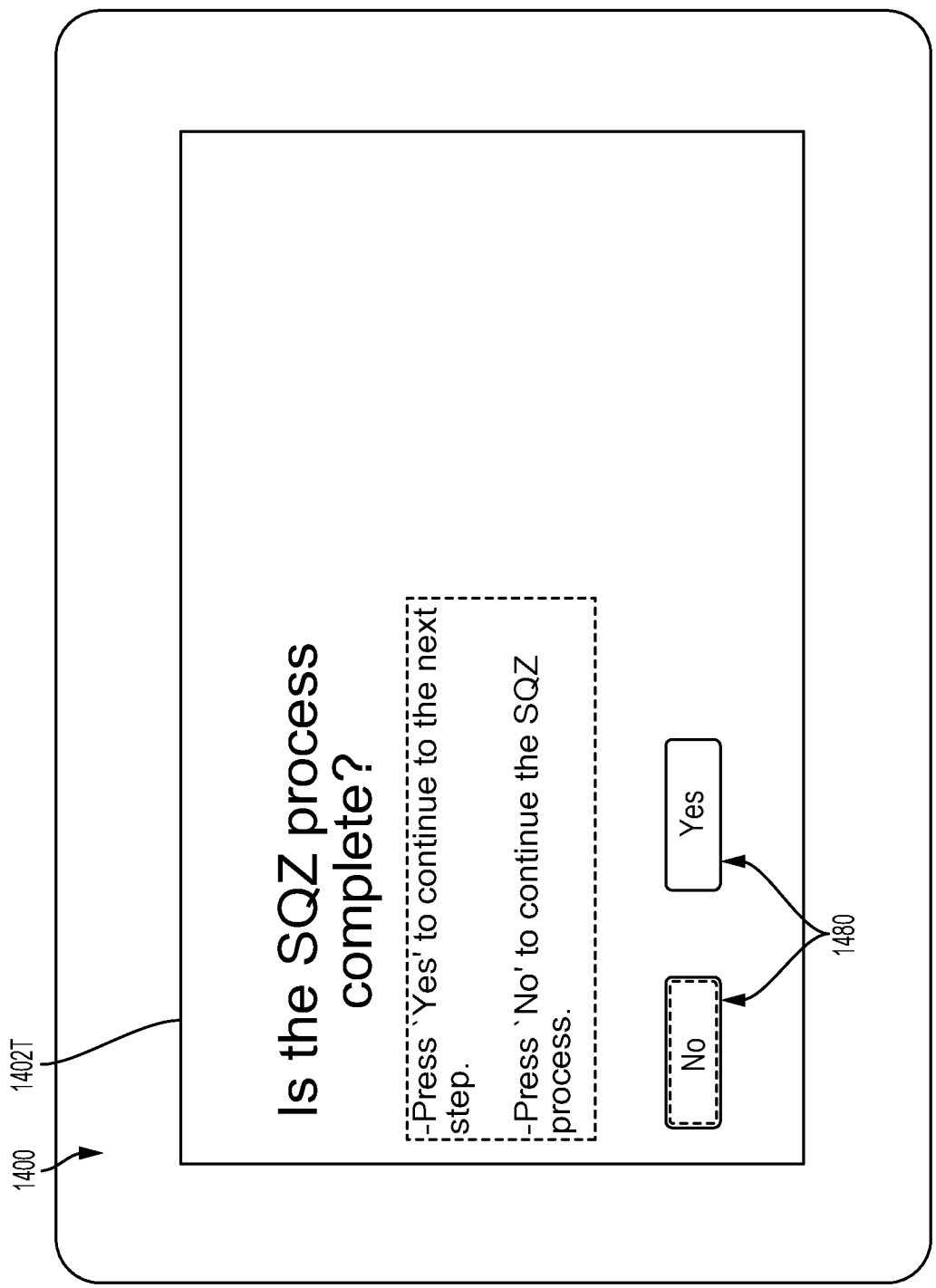
Figure 14U:
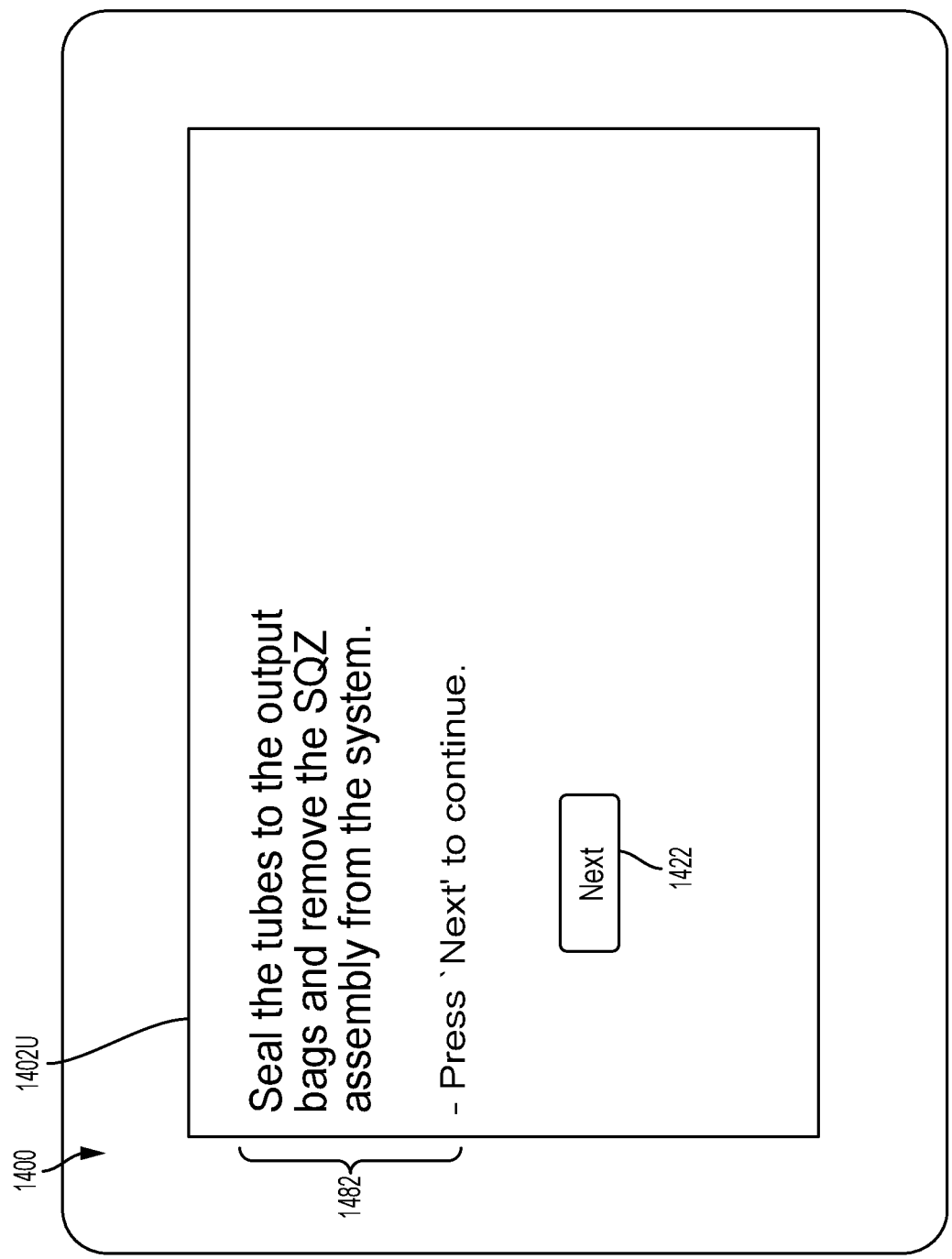
Figure 14V:
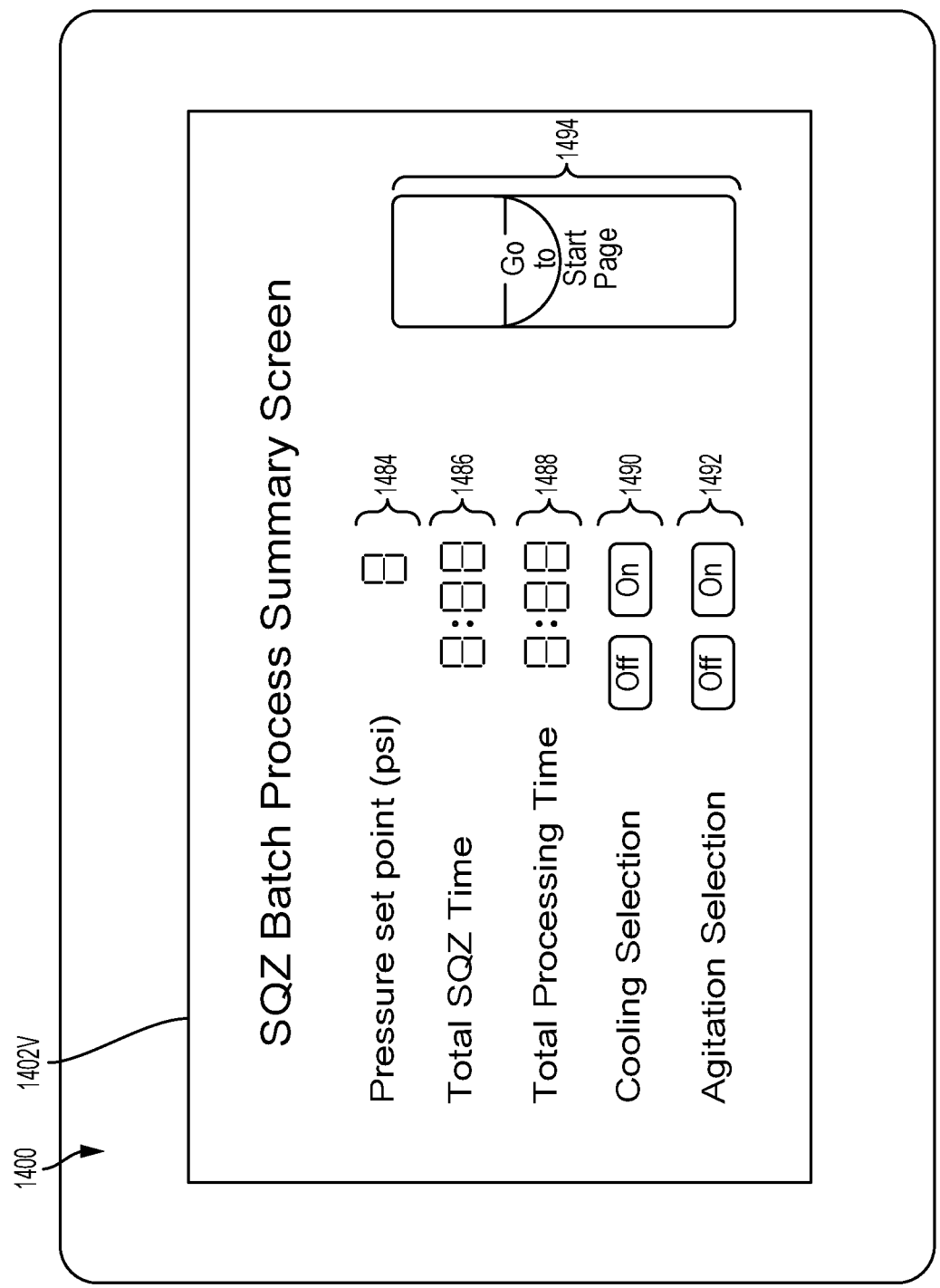

FIGS. 14A-14V illustrate user interface display 1400 for controlling a tabletop system for delivering a payload to a cell, in accordance with some embodiments. In some embodiments, user interface display 1400 may be displayed by any suitable display device, such as display 120 of system 100, which may be located locally to an intracellular payload delivery system (e.g., integrated into a body of the device or attached to the device by a wired electronic communication) or remotely from an intracellular payload delivery system (e.g., configured to communicate with the system by wireless electronic communication). In some embodiments, user interface display 1400 may be configured for use with a touch-screen display, such that a user may touch or tap on displayed buttons or icons of the interface with a finger or stylus; in some embodiments, user interface display 1400 may be configured for use with a non-touch-screen display, such that a user may use a mouse, keyboard, keypad, buttons, pressure-sensitive devices, knobs, joysticks, motion sensing, voice-control, and/or other input devices to navigate and interact with the interface.

In the exemplary embodiments shown in FIGS. 14A-14V, screens 1402A-1402V are displayed on display 1400, where display 1400 may be any local or remote touch-screen display, and may share some or all characteristics in common with display 120 of system 100. As shown and explained below, screens 1402A-1402V may be displayed during various parts of an intracellular payload delivery process, such as method 1300 explained above. As the intracellular payload delivery process progresses, an intracellular payload delivery system may accept various inputs from a user and display various instructions, alerts, and measurements to the user via user interface display 1400.

FIG. 14A illustrates screen 1402A displayed on display 1400. Screen 1402A comprises boot-up message 1404, which may be any graphical and/or textual alert that may be displayed to a user to indicate that the intracellular payload delivery system is booting up.

FIG. 14B illustrates screen 1402B displayed on display 1400. Screen 1402B may be displayed when the intracellular payload delivery system is in an idle state, such as after booting up, or such as when the system is not currently performing any intracellular payload delivery processes. Screen 1402B may comprise intracellular payload delivery process start icon 1406, which may be tapped on or clicked on by a user in order to generate an input to direct the system to begin an intracellular payload delivery process.

FIG. 14C illustrates screen 1402C displayed on display 1400. Screen 1402C may comprise various options for setting up or preparing for an intracellular payload delivery process, including by setting various settings to be used during the process. For example, screen 1402C may enable a user to direct the device whether to use a cooling process, whether to use an agitation process, and what gas pressure should be used for the process.

Screen 1402C may comprise cooling process selection icons 1406, which may allow a user to tap or click the appropriate icon to generate an input to instruct the system to use a cooling (or heating) process or alternately to refrain from using a cooling (or heating) process. In some embodiments, one or more additional icons or user interface elements may be displayed to allow the user to execute inputs to generate instructions to set a target temperature or target temperature range. Once the user makes a selection using icons 1406, the setting may be saved and applied to one or more future payload delivery processes carried out by the system.

Screen 1402C may comprise agitation process selection icons 1408, which may allow a user to tap or click the appropriate icon to generate an input to instruct the system to use an agitation process or alternately to refrain from using an agitation process. In some embodiments, one or more additional icons or user interface elements may be displayed to allow the user to execute inputs to generate instructions to set an agitation rate, intensity, and/or duration. Once the user makes a selection using icons 1408, the setting may be saved and applied to one or more future payload delivery processes carried out by the system.

Screen 1402C may comprise pressure selection icons 1410, which may allow a user to tap or click the appropriate icon to generate an input to instruct the system as to what gas pressure should be used for the payload delivery process. Screen 1402C may also comprise pressure setting display 1412, which may display a pressure that is currently selected by the user, such as by displaying the pressure in pounds per square inch. Once the user makes a selection using icons 1410, the setting may be saved and applied to one or more future payload delivery processes carried out by the system.

Screen 1402C may comprise cancel icon 1416 that may cancel the payload delivery process or may operate as a back button to cause the system to display a previously displayed screen. Screen 1402C may comprise save/continue icon 1414, which may be tapped or clicked by a user in order to save the any settings or inputs made at the current screen and to progress to the next screen and/or next phase in the payload delivery process.

FIG. 14D illustrates screen 1402D displayed on display 1400. Screen 1402D may be a screen displayed to instruct a user to install and/or attach all or part of a disposable assembly, such as a sensor assembly. In some embodiments, the disposable assembly may be associated with a code, identification number, barcode, QR code, or the like, which may be used to ensure single-use and/or regulatory compliance. In some embodiments, the system may prompt (e.g., by display 1400) a user to input or otherwise present a code or identification information of the disposable assembly to the system, such that the system may verify the disposable assembly. In some embodiments, the system may display instructions for disposable assembly installation for every time a payload delivery process is executed, such as when the disposable assemblies are configured for one-time-use only. In some embodiments, the system may read data from one or more sensors to determine whether the disposable assembly is already attached, and may only display attachment/installation instructions if the assembly is not already attached.

As shown, screen 1402D may comprise sensor assembly instructions 1418, which may be any graphical and/or textual instructions regarding how to install and attach the sensor assembly. Similarly, screen 1402D may comprise sensor assembly installation image 1420, which may be an image or video illustrating one or more parts of the instructed installation/attachment process. In the example of FIG. 14D, the sensor assembly instructions instruct the user to run the tubing from the preparation vessel through the bubble sensor, to clip the constriction cartridge into the seat, and to plug the electronic connector of the sensor assembly into an electronic interface of the system. In some embodiments, the instructions displayed may depend on the settings selected by the user at one or more previous screens.

Screen 1402D may comprise next icon 1422 and previous icon 1424, which may be tapped or clicked by a user to move to a next or previous screen, respectively. In some embodiments, the system may automatically display a next screen when it detects that installation of the sensor assembly is complete.

FIG. 14E illustrates screen 1402E displayed on display 1400. Screen 1402E may be a screen displayed to instruct a user to install and/or attach all or part of a disposable assembly, such as a preparation vessel assembly, filter assembly, and/or gas assembly. In some embodiments, the system may display instructions for disposable assembly installation for every time a payload delivery process is executed, such as when the disposable assemblies are configured for one-time-use only. In some embodiments, the system may read data from one or more sensors to determine whether the disposable assembly is already attached, and may only display attachment/installation instructions if the assembly is not already attached.

As shown, screen 1402E may comprise disposable assembly instructions 1426, which may be any graphical and/or textual instructions regarding how to install and attach the sensor assembly. Similarly, screen 1402E may comprise disposable assembly installation image 1428, which may be an image or video illustrating one or more parts of the instructed installation/attachment process. In the example of FIG. 14E, the disposable assembly instructions instruct the user to insert the preparation vessel in its housing, connect a filter to the system, and connect a pressurized sterile gas source and vent lines to the filter assembly. In some embodiments, the instructions displayed may depend on the settings selected by the user at one or more previous screens.

Like screen 1402D, screen 1402E may comprise next icon 1422 and previous icon 1424, which may be tapped or clicked by a user to move to a next or previous screen, respectively. In some embodiments, the system may automatically display a next screen when it detects that installation of the disposable assembly is complete.

FIG. 14F illustrates screen 1402F displayed on display 1400. Screen 1402F may comprise integrity test instructions 1430, which may comprise any graphical and/or written instructions to the user to prepare the system for an integrity test such as a cartridge integrity test. In the example of FIG. 14F, the integrity test instructions instruct the user to confirm that certain input and output valves of the system are closed such that the system may be pressurized without gas leaking into other system components.

Like screen 1402D, screen 1402F may comprise next icon 1422 and previous icon 1424, which may be tapped or clicked by a user to move to a next or previous screen, respectively. In some embodiments of screen 1402F, selecting next icon 1422 may cause the system to initiate the integrity test by causing pressurized gas to flow into the flow path of the system.

FIG. 14G illustrates screen 1402G displayed on display 1400. Screen 1402G may be a screen that is displayed by the system while one or more integrity tests are being carried out. During an integrity test of one or more system components, pressurized gas may be caused to flow into the one or more system components, and a pressure inside the one or more system components may be monitored. As discussed above, if a target pressure is able to be achieved and maintained, then the system may determine that the integrity test has been passed; if the target pressure is not able to be achieved or maintained for at least a predetermined period of time, then the system may determine that the integrity test has been failed, and one or more settings may be required to be changed and/or one or more system components may be required to be adjusted or replaced.

Screen 1402G may comprise dynamic pressure indicator 1432, which may display a dynamic indication of a current internal pressure of the system component or components (e.g., preparation vessel, constriction cartridge, etc.) being subject to the integrity test. Screen 1402G may comprise dynamic elapsed time indicator 1434, which may display a dynamic indication of a current elapsed time for the integrity test being performed.

In some embodiments, the system may automatically display a next screen when it detects that the integrity test is complete.

FIG. 14H illustrates screen 1402H displayed on display 1400. Screen 1402H may be displayed if the system determines that the integrity test was successful in that all components passed the integrity test. Screen 1402H may comprise integrity test success message 1436, which may be any graphical and/or textual indication to alert the user that the integrity test has been passed.

Screen 1402H may comprise next icon 1422, which may be tapped or clicked by a user to move to a next screen. In some embodiments of screen 1402H, the system may automatically display a next screen after a predetermined period of time after beginning to display screen 1402H.

FIG. 14I illustrates screen 1402I displayed on display 1400. Screen 1402I may be displayed if the system determines that the integrity test was not successful in that one or more components did not pass the integrity test. Screen 1402H may comprise integrity test failure message 1438, which may be any graphical and/or textual indication to alert the user that the integrity test has not been passed.

Screen 1402I may further comprise component replacement instructions 1440, which may be any graphical and/or textual instructions indicating to the user that one or more system components needs to be adjusted or replaced and/or that one or more system settings needs to be changed before proceeding (such as by re-running an integrity test with a new disposable assembly). In the example of FIG. 14I, component replacement instructions 1440 instruct the user to remove part of the disposable assembly and obtain a new one.

Screen 1402I may comprise next icon 1422, which may be tapped or clicked by a user to move to a next screen. In some embodiments of screen 1402I, the system may display instructions for installing new components that a user has been instructed to remove after a user taps or clicks next icon 1422. In some embodiments, the system may automatically display new instructions for component installation in response to the system detecting that the failed component has been removed or detached from the system.

FIG. 14J illustrates screen 1402J displayed on display 1400. Screen 1402J may be displayed following a successful integrity test. For example, screen 1402J may be displayed following screen 1402H. In some embodiments, screen 1402J may provide instructions to the user for installing/attaching an input source for fluid material, such as buffer/primer, cell suspension, and/or payload material, to flow through the system during the payload delivery process. For example, a user may be instructed to suspend input bags from hooks of the system and to attach tubing connectors to inlets of the preparation vessel.

As shown, screen 1402J may comprise fluid input source assembly instructions 1442, which may be any graphical and/or textual instructions regarding how to install and attach one or more fluid input sources. Similarly, screen 1402J may comprise fluid input source installation image 1444, which may be an image or video illustrating one or more parts of the instructed installation/attachment process. In the example of FIG. 14J, the fluid input source installation instructions instruct the user to hang the source and primer input bags from the hooks and to attach tubing to inlets of the preparation vessel. In some embodiments, the instructions displayed may depend on the settings selected by the user at one or more previous screens.

Screen 1402J may comprise next icon 1422, which may be tapped or clicked by a user to move to a next screen. In some embodiments, the system may automatically display a next screen when it detects that installation of the fluid input source(s) is complete.

FIG. 14K illustrates screen 1402K displayed on display 1400. Screen 1402K may be an interface that allows a user to select whether the system should use a priming process as part of the payload delivery process. Screen 1402K may comprise priming process selection icons 1446, which may allow a user to tap or click the appropriate icon to generate an input to instruct the system as to whether to use a priming process by passing primer solution through the flow path of the system before passing the cell suspension through the flow path of the system. In some embodiments, screen 1402K may further comprise one or more icons or other user interface object to allow a user to enter parameters or settings for the priming process, such as a source of the primer solution or a pressure or temperature to be used for the priming process. Once the user makes a selection using icons 1446, the setting may be saved and applied to one or more future payload delivery processes carried out by the system.

FIG. 14L illustrates screen 1402L displayed on display 1400. Screen 1402L may be displayed in some embodiments in response to a user using icons 1446 to indicate that a priming process should be performed. Screen 1402L may comprise priming preparation instructions 1448, which may comprise any graphical and/or written instructions to the user to prepare the system for a priming process. In the example of FIG. 14L, priming preparation instructions 1448 instruct the user to fill the preparation vessel with primer/buffer solution, ensure that valves are in the proper orientation, and ensure that valves to the cell suspension source bag are closed. It should be noted that it some embodiments, these or other steps that the system instructs the user to perform may instead be automatically performed by the system, such as by electronically actuating valves.

Like screen 1402D, screen 1402L may comprise next icon 1422 and previous icon 1424, which may be tapped or clicked by a user to move to a next or previous screen, respectively. In some embodiments of screen 1402L, selecting next icon 1422 may cause the system to initiate the priming process by actuating one or more valves or other system components to cause primer/buffer solution to flow through the flow path of the system.

FIG. 14M illustrates screen 1402M displayed on display 1400. Screen 1402M may be displayed as the system completes a priming process. Screen 1402M may comprise dynamic pressure indicator 1450, which may display a dynamic indication of a current internal pressure of one or more system components or contents (e.g., preparation vessel, constriction cartridge, etc.) during the priming process. In some embodiments, screen 1402M may comprise dynamic temperature indicator 1452, which may display a dynamic indication of a current temperature of one or more system components or contents (e.g., a calculated effective temperature of the primer solution) during the priming process. In some embodiments, screen 1402M may comprise a dynamic elapsed time indicator (not shown), such as dynamic elapsed time indicator 1434, which may display a dynamic indication of a current elapsed time during the priming process.

In some embodiments, the system may automatically display a next screen when it detects that the priming process is complete.

FIG. 14N illustrates screen 1402N displayed on display 1400. Screen 1402N may be displayed when the system detects that a priming process has been completed. For example, when a flow sensor (e.g., flow sensor 912 of system 100) detects that primer/buffer solution is no longer flowing through one or more tubes of the system, the system may determine that the priming process has been completed and may display screen 1402N. Screen 1402N may in some embodiments prompt a user to confirm that the priming process has been completed.

Screen 1402N may comprise priming completion confirmation icons 1454, which may be which may be tapped or clicked by a user to indicate whether the priming process has been completed. In some embodiments, indicating that the priming process has been completed (e.g., by tapping a "Yes" icon) may cause the system to progress to the next step and display the next screen. In some embodiments, indicating that the priming process has not been completed may cause the system to continue the priming process for a predetermined period of time, until a user indicates otherwise, or until the system again detects that the priming process has been completed. In some embodiments, confirming that the priming process has been completed may cause the system to actuate one or more valves or other system components to close a primer/buffer solution flow path and/or to open a flow path for the cell suspension, and may cause the system to proceed to a next screen.

FIG. 14O illustrates screen 1402O displayed on display 1400. Screen 1402O may comprise cell suspension flow process setup instructions 1456, which may comprise any graphical and/or written instructions to the user to prepare the system for a cell suspension flow process in which the cell suspension is caused to flow through the preparation vessel, constriction cartridge, and/or other components of the system. In the example of FIG. 14O, cell suspension flow process preparation instructions 1456 instruct the user fill the preparation vessel with the cell suspension and to press a button to start the cell suspension flow process. It should be noted that it some embodiments, these or other steps that the system instructs the user to perform may instead be automatically performed by the system, such as by electronically actuating valves.

Screen 1402O may comprise cell suspension flow process start icon 1458, which may be tapped or clicked by a user to signal an instruction to cause the system to begin the cell suspension flow process, such as by actuating one or more valves or other system components to cause the cell suspension to flow into and through the preparation vessel, be prepared while in the preparation vessel, flow into and through the constriction cartridge, and flow into an output bag. In some embodiments, selecting icon 1458 to start the cell suspension flow process may also cause the system to begin monitoring one or more characteristics of the system and/or cell suspension, such as an elapsed time, pressure, temperature, and/or agitation state, and may cause the system to proceed to a next screen.

FIG. 14P illustrates screen 1402P displayed on display 1400. Screen 1402P may comprise agitation process selection icons 1460, which may allow a user to tap or click the appropriate icon to generate an input to instruct the system to use an agitation process or alternately to refrain from using an agitation process. In some embodiments, one or more additional icons or user interface elements may be displayed to allow the user to execute inputs to generate instructions to set an agitation rate, frequency, intensity, amplitude, and/or duration. Once the user makes a selection using icons 1408, the setting may be saved and applied to one or more future payload delivery processes carried out by the system. In some embodiments, agitation selection icons 1460 may differ from agitation selection icons 1408 on screen 1402C in that icons 1408 may be used to set a general system setting to be applied by default to all payload delivery processes, whereas icons 1460 may be used to set a specific setting to be applied only to the current payload delivery process.

In some embodiments, selecting either of the agitation selection icons 1460 may cause the system to display a next screen and to proceed with the cell suspension flow process with or without agitation, as indicated.

FIG. 14Q illustrates screen 1402Q displayed on display 1400. Screen 1402Q may be displayed, in some embodiments, while the cell suspension is being prepared inside the preparation vessel, such as by being cooled, agitate, and/or subject to increasing gas pressure.

Screen 1402Q may comprise dynamic pressure indicator 1462, which may display a dynamic indication of a current internal pressure of the system component or components (e.g., preparation vessel, constriction cartridge, etc.) during the cell suspension preparation process. Screen 1402Q may comprise dynamic temperature indicator 1464, which may display a dynamic indication of a current temperature of one or more system components or contents (e.g., a calculated effective temperature of the cell suspension) during the cell suspension preparation process. Screen 1402Q may comprise dynamic process timer indicator 1466, which may display a dynamic indication of a current elapsed time for the payload delivery process, cell suspension flow process, and/or cell suspension preparation process.

In some embodiments, the system may automatically progress to a next screen after a predetermined period of time, when the system detects that the preparation process is complete (such as by detecting that the dynamic pressure of the system has reached and/or sustained the target pressure and/or that the dynamic temperature of the system has reached and/or sustained the target temperature).

FIG. 14R illustrates screen 1402R displayed on display 1400. Screen 1402R may, in some embodiments, be displayed after the cell suspension preparation process is completed. Screen 1402R may comprise post-preparation instructions 1468, which may comprise any graphical and/or written instructions to the user to prepare the system for the remainder of the cell suspension flow process following preparation of the cell suspension in the preparation vessel, such as by adjusting valves or other system components in advance of the cell suspension being caused to flow under pressure through the constriction cartridge. In the example of FIG. 14R, post-preparation instructions 1468 instruct the user to ensure that valves are in the proper orientation and that the valves for the primer/buffer solution output bag are closed. It should be noted that in some embodiments, these or other steps that the system instructs the user to perform may instead be automatically performed by the system, such as by electronically actuating valves.

Screen 1402R may comprise next icon 1422, which may be tapped or clicked by a user to move to a next screen. In some embodiments of screen 1402L, selecting next icon 1422 may cause the system to initiate the remaining portion of the cell suspension flow process, such as by causing the cell suspension to flow under pressure through the constriction cartridge. In some embodiments, the next screen may be automatically displayed and the system may automatically cause the remaining portion of the cell suspension flow process to initiate in accordance with the system detecting that the cell suspension preparation is complete and/or that system components such as various valves are in the correct orientation for the cell suspension to flow through the constriction cartridge and into the correct output bag.

FIG. 14S illustrates screen 1402S displayed on display 1400. Screen 1402S may be displayed, in some embodiments, during all or part of the cell suspension flow process, such as during the time period when the cell suspension is flowing through the constriction cartridge.

Screen 1402S may comprise dynamic pressure indicator 1470, which may display a dynamic indication of a current internal pressure of the system component or components (e.g., preparation vessel, constriction cartridge, etc.) during the cell suspension flow process. Screen 1402S may comprise dynamic temperature indicator 1472, which may display a dynamic indication of a current temperature of one or more system components or contents (e.g., a calculated effective temperature of the cell suspension) during the cell suspension flow process.

Screen 1402S may comprise first dynamic process timer indicator 1474, which may display a dynamic indication of a first current elapsed time for the payload delivery process, cell suspension flow process, and/or any one or more other sub-processes of the overall payload delivery process. Screen 1402S may comprise second dynamic process timer indicator 1476, which may display a dynamic indication of a second current elapsed time for the payload delivery process, cell suspension flow process, and/or any one or more other sub-processes of the overall payload delivery process. The second current elapsed time may be different from the first current elapsed time; for example, in FIG. 14S, first dynamic time indicator 1474 shows a time for the overall process (e.g., starting from priming or cell suspension preparation), while second dynamic time indicator 1476 shows a time for the cell suspension flow process (e.g., starting from the cell suspension preparation process or the time at which the cell suspension begins flowing through the constriction cartridge). In some embodiments, one time indicator may indicate a total time that cells are in the system while the other time indicator may indicate a total time that pressure has been applied to the cells.

Screen 1402S may comprise agitation stop icon 1478, which may be tapped or clicked by a user to stop an agitation process of the system, such as by causing the system to send a signal to cause a shaker plate or other agitation device to stop agitating the cell suspension. In some embodiments, a user may desire to stop the agitation process, for example, if there is a small volume of fluid left in the preparation vessel and continued agitation would risk passing bubbles through the constriction cartridge, or if there is a large volume of fluid and agitation could cause spillage out of the preparation vessel.

In some embodiments, the system may automatically display a next screen when it detects that the cell suspension flow process is complete. This detection may be performed in accordance with any one or more of the sensors discussed herein, such as a bubble sensor monitoring flow, or by monitoring sample volume (e.g., volume of fluid in the preparation vessel) during the cell suspension flow process.

FIG. 14T illustrates screen 1402T displayed on display 1400. Screen 1402T may be displayed when the system detects that a cell suspension flow process has been completed. For example, when a flow sensor (e.g., flow sensor 912 of system 100) detects that the cell suspension is no longer flowing through one or more tubes of the system, the system may determine that the cell suspension flow process has been completed and may display screen 1402T. Screen 1402T may in some embodiments prompt a user to confirm that the cell suspension flow process has been completed.

Screen 1402T may comprise cell suspension flow completion confirmation icons 1480, which may be which may be tapped or clicked by a user to indicate whether the cell suspension flow process has been completed. In some embodiments, indicating that the cell suspension flow process has been completed (e.g., by tapping a "Yes" icon) may cause the system to progress to the next step and display the next screen. In some embodiments, indicating that the cell suspension flow process has not been completed may cause the system to continue the cell suspension flow process for a predetermined period of time, until a user indicates otherwise, or until the system again detects that the cell suspension flow process has been completed. In some embodiments, confirming that the cell suspension flow process has been completed may cause the system to actuate one or more valves or other system components to close a cell suspension flow path.

FIG. 14U illustrates screen 1402U displayed on display 1400. Screen 1402U may be a screen displayed to instruct a user to remove all or part of a disposable assembly, such as a preparation vessel assembly, filter assembly, and/or gas assembly. In some embodiments, the system may display instructions for disposable assembly removal for every time a payload delivery process is executed, such as when the disposable assemblies are configured for one-time-use only. In some embodiments, the system may read data from one or more sensors to determine whether the disposable assembly is already removed, and may only display detachment/removal instructions if the assembly is not already removed.

As shown, screen 1402U may comprise disposable assembly removal instructions 1482, which may be any graphical and/or textual instructions regarding how to detach and remove the disposable assembly. In some embodiments, screen 1402U may comprise a disposable assembly removal image (not shown), which may be an image or video illustrating one or more parts of the instructed removal process. In the example of FIG. 14U, the disposable assembly removal instructions instruct the user to seal tubes to the output bags (which in some embodiments may be done automatically by electronic valves) and to remove the disposable assembly from the system. In some embodiments, the instructions displayed may depend on the settings selected by the user at one or more previous screens.

Screen 1402U may comprise next icon 1422, which may be tapped or clicked by a user to move to a next screen. In some embodiments, the system may automatically display a next screen when it detects that removal of the disposable assembly is complete.

FIG. 14V illustrates screen 1402V displayed on display 1400. Screen 1402V may be a process summary screen displayed after completion of the payload delivery process.

Screen 1402V may comprise pressure indicator 1484, which may display an indication of pressure set-point that was used for the payload delivery process that was just completed. Alternately or additionally, pressure indicator 1484 may indicate one or more actual pressure measurements taken during the payload delivery process, such as a highest pressure, lowest pressure, and/or average pressure measured during the process.

Screen 1402V may comprise first static time indicator 1486, which may display an indication of a total elapsed time for the total payload delivery process. Screen 1402V may comprise second static time indicator 1488, which may display an indication of a total elapsed time for the cell suspension flow process (or for any one or more other sub-processes included in the overall payload delivery process). The second total time may be different from the first total elapsed time; for example, in FIG. 14V, first static time indicator 1486 shows a time for the overall process (e.g., starting from priming or cell suspension preparation), while second static time indicator 1488 shows a time for the cell suspension flow process (e.g., starting from the cell suspension preparation process or the time at which the cell suspension begins flowing through the constriction cartridge). In some embodiments, one time indicator may indicate a total time that cells are in the system while the other time indicator may indicate a total time that pressure has been applied to the cells.

Screen 1402V may comprise temperature control selection indicator 1490, which may indicate whether a temperature control process was selected by a user and/or executed by the system during the process that was just completed. In some embodiments, screen 1402V may also display information about the temperature control process, such as a time elapsed during the process, starting and ending temperatures during the process, average temperature during the process, and/or a graph depicting temperatures over time during the process.

Screen 1402V may comprise agitation selection indicator 1492, which may indicate whether an agitation process was selected by a user and/or executed by the system during the process that was just completed. In some embodiments, screen 1402V may also display information about the agitation process, such as a rate, duration, intensity, and/or indication as to whether and when a user stopped the agitation process.

In some embodiments, screen 1402V may comprise temperature indicator (not shown), which may display an indication of temperature set-point that was used for the payload delivery process that was just completed. Alternately or additionally, the temperature indicator may indicate one or more actual temperature measurements taken (or effective temperatures calculated) during the payload delivery process, such as a highest temperature, lowest temperature, and/or average temperature measured during the process.

Screen 1402V may comprise start-page return icon 1494, which may be tapped or clicked by a user to signal an input to instruct the system to return to a start screen such as screen 1402B. In some embodiments, a start-page return icon such as icon 1494 may be included on any one or more of the other screens discussed herein with respect to FIGS. 14A-14V.

In some embodiments, screen 1402V may comprise a dedicated icon or other user interface object (not shown) for storing or transmitting data detected and/or logged by the system during the payload delivery process that was just completed. In some embodiments, the system may be configured to automatically log data regarding temperature, pressure, agitation, flow rate, processing time, impedance, light-based sensor data, cell concentration, and/or membrane disruption, based on information detected by any one or more sensors during the payload delivery process. In some embodiments, the system may be configured to automatically store and/or transmit the logged information upon completion of the process, upon a user executing an instruction to do so, and/or upon a user tapping or clicking start-page return icon 1494.

In some embodiments, any one or more of the inputs made by a user via interface 1400 may be replaced by the user's indication of a pre-set routine or recipe, which may predetermine multiple settings (e.g., temperature settings, pressure settings, agitation settings, etc.) and cause the system to execute the payload delivery process in accordance with the pre-set routine or recipe.

Additional Intracellular Payload Delivery Systems

FIGS. 15-20 illustrate exemplary embodiments of tabletop laboratory systems and associated devices and components for intracellular payload delivery, including flexible bags usable therein, wherein the systems and devices may be used in conjunction with the methods, techniques, and user interfaces described herein. The systems described in FIGS. 15-20 may share any one or more characteristics in common with the systems described above in FIGS. 1-11, including sharing common components, sharing common characteristics, and/or being usable in the all or part of the same methods and/or techniques as described herein. Components, features, and applications described with respect to FIGS. 15-20 may be combined with components, features, and applications described with respect to FIGS. 1-11. As with the systems described in FIGS. 1-11, the systems described in FIGS. 15-20 may be usable in the methods described with respect to FIGS. 11 and 12, and/or may be usable in conjunction with the user interface described with respect to FIG. 14.

Figure 15A:
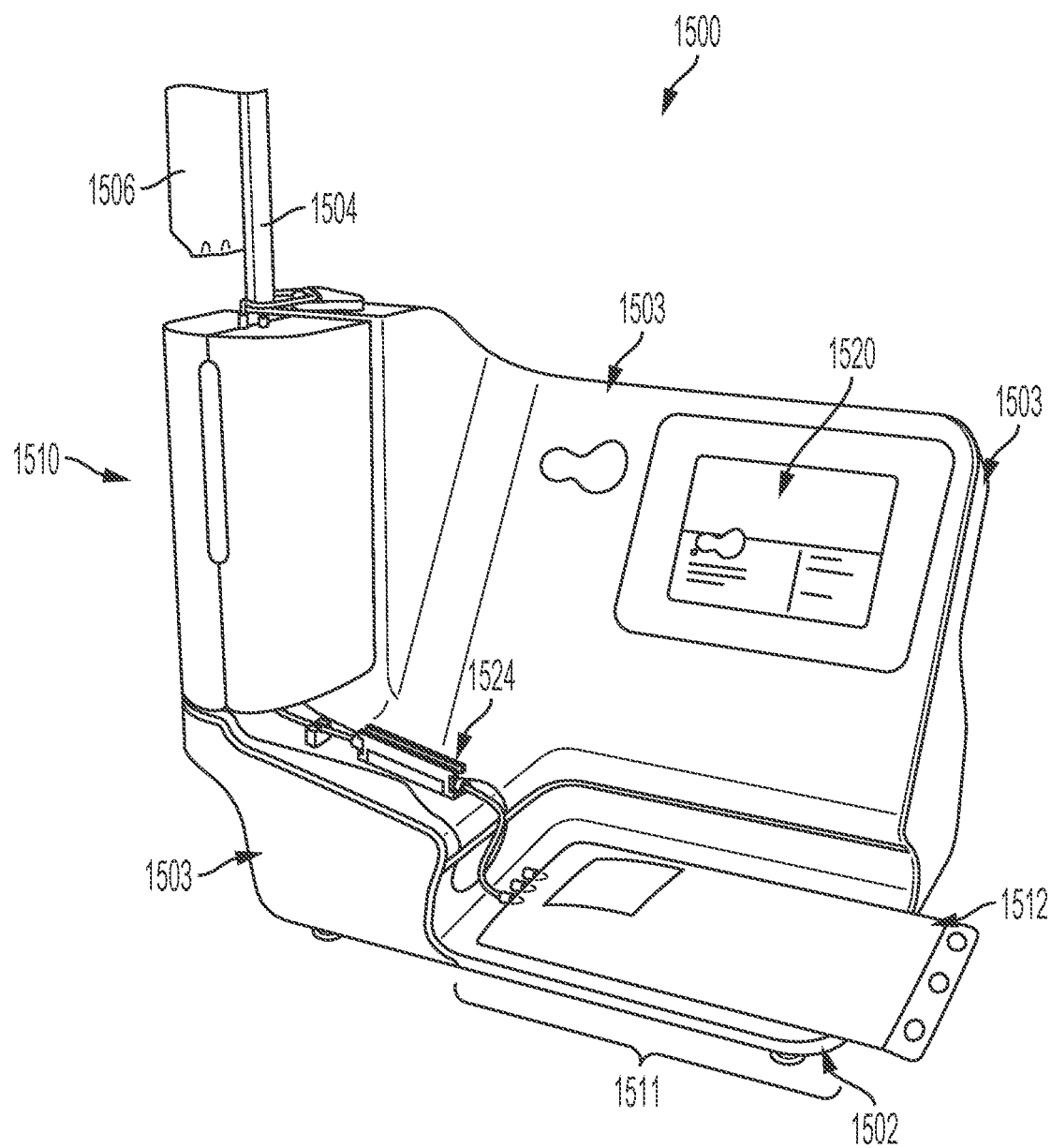
FIGS. 15A-15C illustrate a tabletop system for delivering a payload to a cell, in accordance with some embodiments.
Figure 15B:
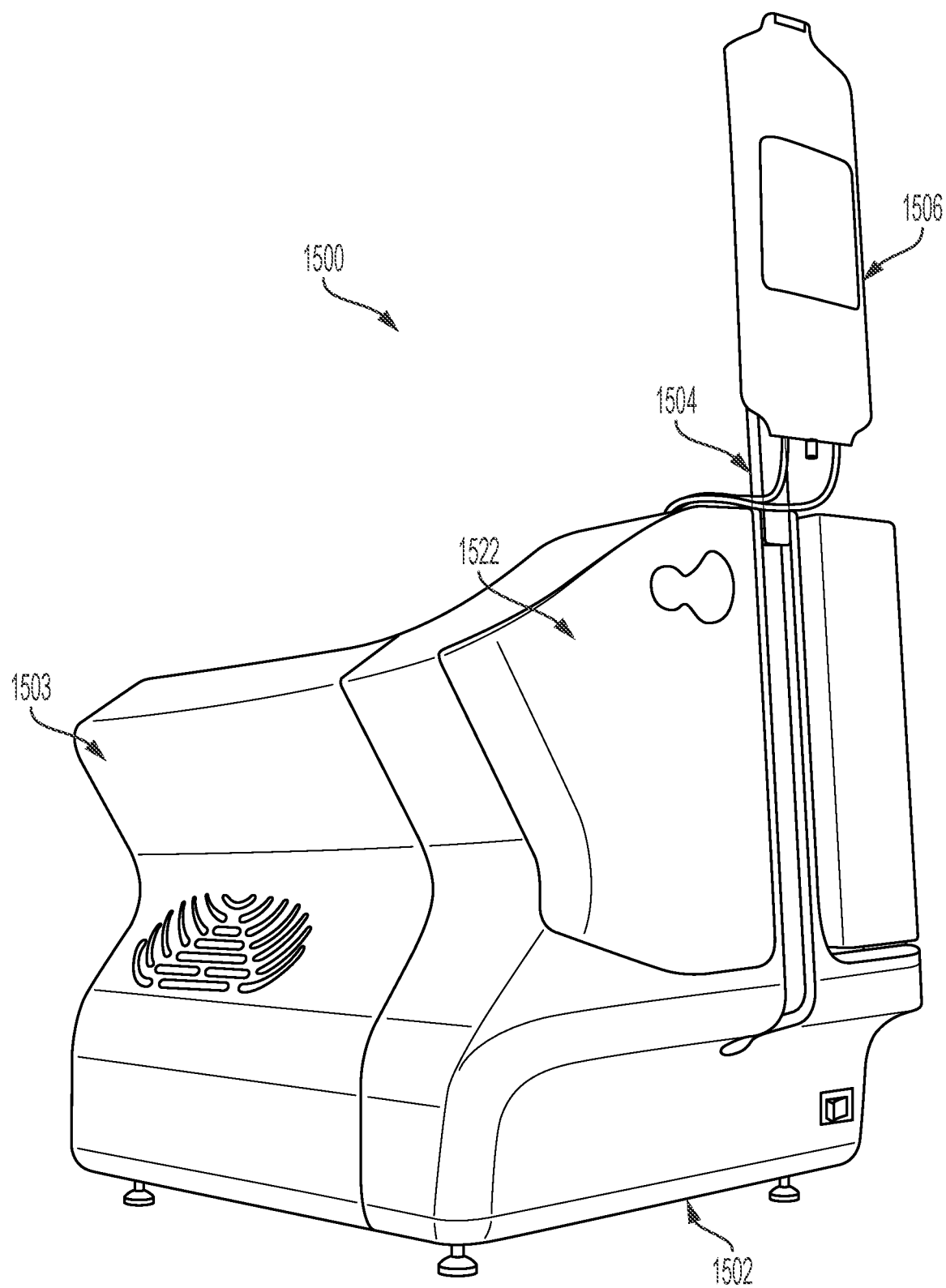
Figure 15C:
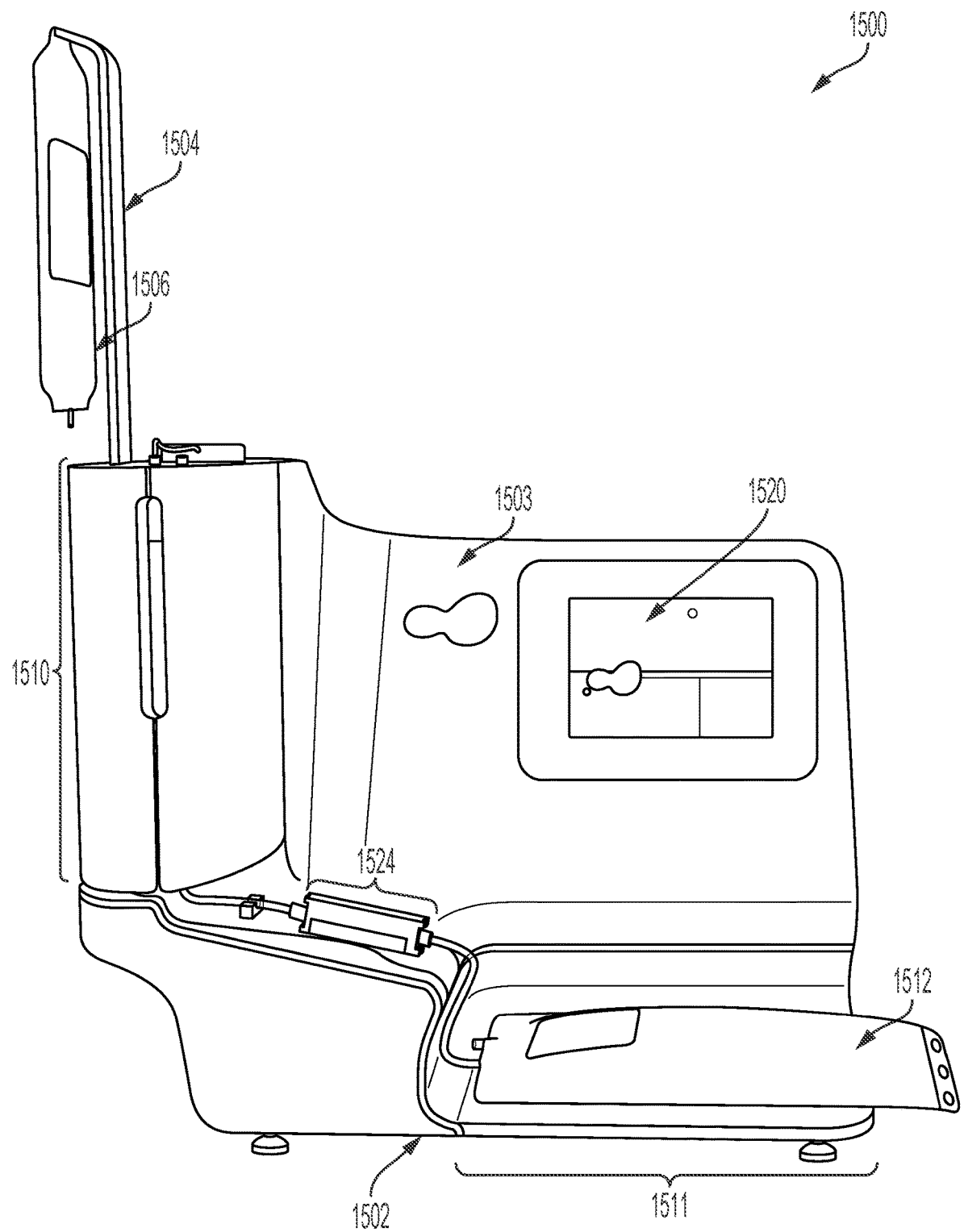

FIGS. 15A-15C illustrate a tabletop system 1500 for delivering a payload to a cell, in accordance with some embodiments. Like system 100 described above with respect to FIG. 1 (and other figures making reference to system 100), system 1500 may be a tabletop system, such as a piece of laboratory equipment, configured to accept cellular suspension fluid and to process the cellular suspension fluid to deliver a payload to the cells of the cellular suspension. System 1500 and its components/features may share any one or more characteristics in common with system 100 and/or its respective components/features and/or with system 1000 and its respective components/feature, and system 1500 may be used in all or part of any of the same manners, methods, and/or techniques As shown in FIGS. 15A-15C and described herein, system 1500 may differ from system 100 and/or system 1000 in several ways. Namely, system 1500 may have a different physical shape from system 100 defined by the housing of system 1500, may have different temperature control systems from system 100, and/or may a different preparation vessel and preparation vessel housing from system 100. Regarding the preparation vessel and preparation vessel housing, system 1500 may make use of a flexible preparation bag inside a rigid preparation housing, rather than the rigid preparation vessel of system 100. As described below, using a flexible bag in place of a rigid preparation vessel may improve cooling functionality of the system, because heat-transfer to and from liquid inside a flexible bag may be more efficient than heat transfer to and from liquid inside a rigid plastic vessel.

As shown in FIG. 15A, system 1500 may comprise base plate 1502, housing 1503, hook 1504, input bag 1506, preparation vessel housing 1510, output bag tray area 1511, output bag 1512, display 1520, and constriction cartridge 1524.

Base plate 1502 may be a platform upon which one or more components of system 1500 are mounted. For example, system 1500 may be a tabletop system mounted atop base plate 1502. Base plate 1502 may share any one or more characteristics in common with platform 102 described above with respect to FIG. 1. In some embodiments, base plate 1502 may be independent from one or more other components of system 1500, while in some embodiments it may be integrated (e.g., formed as a single piece) with one or more other components of system 1500. Base plate 1502 may be made of any suitable material, including metal or plastic; metal may be preferred in order to ensure that base plate 1502 is sufficiently sturdy and heavy in order to give system 1500 a low center of gravity.

Housing 1503 may be any outer housing for system 1500, and may define the outer shape of system 1500 and protect internal components from damage and/or contamination. Housing 1503 may be made of one piece or made of two or more separate pieces. In the example shown in FIGS. 15A-15C, housing 1503 comprises a lower/back portion and an upper/front portion, and the two portions may assemble together (e.g., by snapping together, being screwed together, or being bonded together by adhesive) to form housing 1503. Housing 1503 may be made of any suitable material, including metal or plastic; metal may be preferred to ensure that system 1500 is sufficiently durable; plastic may be preferred to ensure that system 1500 is not overly heavy and to ensure that the center of gravity of system 1500 is not excessively elevated from base plate 1502; materials suitable for use in a clean-room environment may be preferred.

In some embodiments, housing 1503 may share any one or more characteristics in common with the housings of pressure control module 116, temperature control module 118, and/or preparation vessel housing 110. In some embodiments, housing 1503 may contain any one or more of the components of system 100 described above with respect to FIG. 1, including components located inside or outside one or more of pressure control module 116, temperature control module 118, and/or preparation vessel housing 110. In some embodiments, system 1500 may provide a more streamlined structure as compared to system 100, where more internal components may be located inside a single housing structure rather than a plurality of separate housing structures.

Hook 1504 may be a structure configured to suspend one or more bags, such as bags containing cell suspension and/or other media. As shown in FIG. 15, hook 1504 is configured to suspend input bag 1506, which may share any one or more features in common with bags 106 and/or 108 described above with respect to FIG. 1. Hook 1504 may similarly share any one or more features in common with hook 104 described above with respect to FIG. 1. Similar to system 100, a flow path in system 1500 may originate at input bag 1506 and lead through one or more pipes or flexible tubes toward other system components, including (in system 1500) one or more flexible bags inside preparation vessel housing 1510.

In some embodiments, hook 1504 may be movable between an extended position and a collapsed position. In the extended position, hook 1504 may extend upward above preparation vessel housing 1510 in order to suspend bag 1506, while in a collapsed position hook 1504 may be located in a position closer to other system components, such that system 1500 takes up less space overall when hook 1504 is in the collapsed position. In some embodiments, hook 1504 may move between the extended and collapsed positions by rotating on a hinge, sliding along a slide track, or detaching from system 1500 and reattaching in the extended position. In some embodiments, hook 1504 may collapse into housing 1503 in the collapsed position, or may lie parallel with and/or flush with one or more walls of housing 1503 in the collapsed position.

Preparation vessel housing 1510 may be any structure or component configured to house a preparation vessel. Preparation vessel housing 1510 may share any one or more features in common with preparation vessel 110 described above with respect to FIG. 1, including being configured to house a preparation vessel containing cell suspension fluid as it is prepared for passage through a constriction component, wherein the constriction component defines a part of the flow path configured to cause perturbations in membranes of the cells of the cell suspension fluid in order to facilitate entry of the payload into the cells through the membranes, including by holding the cell suspension while the suspension is cooled (or heated), agitated, as the cell suspension has air pressure applied to it, and/or as the cell suspension is otherwise manipulated or controlled to be forced through a constriction component.

As described in greater detail below with respect to FIGS. 15-19, a preparation vessel may comprise a flexible bag, such as a flexible plastic bag, in place of and/or in addition to a rigid vessel such as vessel 600 described above with respect to FIG. 6A and/or system 100. Preparation vessel housing 1510 may thus differ from preparation vessel 100 in that preparation vessel housing 1510 may be configured to house a preparation vessel in the form of a flexible bag, rather than in the form of a rigid vessel. Preparation vessel housing 1510 may be configured to house a preparation vessel in the form of a flexible bag by having an internal cavity in the shape of a filled flexible bag. In this way, when the flexible bag is filled with fluid and/or pressurized gas, it may press against the internal walls of preparation vessel housing 1510, in such a way that preparation vessel housing 1510 may create a bag-lined cavity.

One advantage of using a preparation vessel in the form a flexible bag may be increased efficiency in heat transfer to and/or from fluid inside the bag while it is inside preparation vessel housing 1510. Because the walls of a flexible bag (e.g., a plastic flexible bag) may be significantly thinner than the walls of a rigid vessel, and because the walls of a flexible bag may deform to increase the surface area of contact between the bag and the interior walls of preparation vessel housing 1510, heat transfer to and from the fluid inside the bag may be more efficient and faster than with thicker walls and less surface area contact.

In order to facilitate this efficient heat transfer, preparation vessel housing 1510 may comprise a temperature control system. In some embodiments, the temperature control system of preparation vessel housing 1510 may share any one or more characteristics in common with any of the components of and/or associated with temperature control module 118 discussed above with respect to FIG. 1. In some embodiments, the temperature control system of preparation vessel housing 1510 may comprise any one or more components configured to heat and/or cool fluid inside a preparation vessel inside preparation vessel housing 1510, such as one or more forced-air heaters, one or more forced-air coolers, one or more thermoelectric cooling devices (e.g., Peltier coolers), one or more resistive heating devices, one or more liquid heating devices, one or more liquid cooling devices, or the like.

In some embodiments, one or more thermoelectric cooling devices (e.g., cooling plates) may be integrated into preparation vessel housing 1510 such that they may form part of one or more inner walls of preparation vessel housing 1510. A flexible bag or other preparation vessel inside preparation vessel housing 1510 may then come into contact with the thermoelectric cooling device(s) (e.g., cooling plate(s)), thereby drawing heat from the fluid inside the vessel and cooling the fluid therein. In some embodiments, a flexible bag (as described in greater detail below) may have a front side and a back side which form large flat areas at which the bag may come into contact with a thermoelectric cooling plate. In some embodiments, preparation vessel housing 1510 may comprise a first thermoelectric cooling plate configured to contact a front side of a flexible bag, and a second thermoelectric cooling plate, positioned opposite the first plate inside thermoelectric cooling plate, configured to contact the back side of the flexible bag.

Preparation vessel housing 1510 may comprise one or more openable doors. The one or more doors may be movable between open positions and closed position, for example by being movably mounted on hinges. Opening one or more doors of preparation vessel housing 1510 may allow removal and/or replacement of a preparation vessel (e.g., a flexible bag) (and/or any other component) located inside preparation vessel housing 1510. In some embodiments, one or more thermoelectric cooling devices (e.g., cooling plates) may be integrated into a door of preparation vessel housing 1510, such that closing the door may cause the one or more thermoelectric cooling devices to press against a preparation vessel positioned inside preparation vessel housing 1510.

In some embodiments, system 1500 may be configured such that positive pressure inside a flexible bag vessel inside preparation vessel housing 1510 may be used to ensure that the exterior walls of the flexible bag are pressed into contact with the interior walls of preparation vessel housing 1510, thereby ensuring an effective surface area for temperature control, even as fluid is evacuated from the flexible bag. To supply positive pressure inside the flexible bag, a gas (such as a sterile gas or pressurized air) may be pumped inside the flexible bag at a pressure sufficient to cause the bag to expand and/or press against the interior walls of preparation vessel housing 1510. In some embodiments, the pressure sufficient to cause the bag to expand and/or press against the interior walls of preparation vessel housing 1510 may be greater than 2 psi, 5 psi, 10 psi, 25 psi, 40 psi, 80 psi, 100 psi, 120 psi, 140 psi, or 160 psi. In some embodiments, the pressure sufficient to cause the bag to expand and/or press against the interior walls of preparation vessel housing 1510 may be less than 2 psi, 5 psi, 10 psi, 25 psi, 40 psi, 80 psi, 100 psi, 120 psi, 140 psi, or 160 psi.

In some embodiments, one or more thermoelectric cooling devices, such as one or more cooling plates, may be positioned inside preparation vessel housing 1510 such that they may contact fluid inside a flexible bag inside preparation vessel housing 1510 even when the fluid level is low. For example, cooling plates may be positioned at or near the bottom of preparation vessel housing 1510, such that even when the fluid level in the vessel is below 50%, below 25%, below 10%, or below 5%, all or some of the surface area of the one or more cooling plates may still come into contact with all or part of the portion of the vessel that is in contact with the fluid remaining in the vessel.

In some embodiments, where the one or more thermoelectric cooling devices comprise one or more cooling plates, the plates may be surrounded by insulation on the back and/or to the sides; in some embodiments, the insulation may be 3D-printed to fit the plates snugly.

In some embodiments, one or more individual thermoelectric cooling plates used in preparation vessel housing 1510 may have a functional surface area of greater than 10,000 mm$^2$, 12,100 mm$^2$, 14,400 mm$^2$, 16,900 mm$^2$, or 19,600 mm$^2$. In some embodiments, one or more individual thermoelectric cooling plates used in preparation vessel housing 1510 may have a functional surface area of less than 10,000 mm$^2$, 12,100 mm$^2$, 14,400 mm$^2$, 16,900 mm$^2$, or 19,600 mm$^2$.

In some embodiments, one or more temperature control devices used in preparation vessel housing 1510 may comprise a temperature probe, such as a hot-side temperature probe configured to measure coolant temperature entering a radiator for fan control of the device. In some embodiments, one or more temperature control devices used in preparation vessel housing 1510 may comprise a cold-side temperature probe, such as one embedded in a cooling plate, configured to take a temperature reading of the cooling plate.

In some embodiments, one or more temperature control devices used in preparation vessel housing 1510 may be configured to heat and/or cool fluid inside a vessel inside preparation vessel housing 1510 in accordance with any one or more of the temperature ranges and/or time ranges discussed above with respect to block 1324. In some embodiments, system 1500 may be configured to cool fluid inside preparation vessel housing 1510 from greater than 20 degrees Celsius, 22 degrees Celsius, 24 degrees Celsius, 30 degrees Celsius, 34 degrees Celsius, 36 degrees Celsius, or 38 degrees Celsius to less than 8 degrees Celsius, 6 degrees Celsius, 5 degrees Celsius, or 4 degrees Celsius, 2 degrees Celsius, or 1 degree Celsius; in some embodiments, system 1500 may be configured to cool fluid inside preparation vessel housing 1510 over one or more of these ranges in a time period of less than 1 hour, 45 minutes, 30 minutes, 15 minutes, 10 minutes, or 5 minutes.

Once fluid inside preparation vessel housing 1510 has been prepared for passage out of preparation vessel housing 1510 (e.g., toward and through a constriction cartridge), the fluid may be forced out of an outlet of a flexible bag in preparation vessel housing 1510 and through one or more tubes or pipes toward a downstream component such as a constriction cartridge. As discussed above with respect to system 100, fluid may be forced out of the preparation vessel of system 1500 by pressurizing gas inside the preparation vessel. Because the preparation vessel in system 1500 may be a flexible bag, preparation vessel housing 1510 may provide a rigid structure (e.g., a shell) that prevents the flexible bag preparation vessel from rupturing or otherwise failing when the bag is pressurized. In some embodiments, gas pressures the same or similar to those discussed above with respect to forcing fluid out of vessel 600 in system 100 may be used.

In some embodiments, preparation vessel housing 1510 may comprise (and/or be provided alongside with) one or more of (a) a flow sensor (e.g., a bubble sensor) upstream of the preparation vessel, which may be used to monitor when all liquid has entered the preparation vessel from an upstream component such as an input bag; (b) a flow sensor (e.g., a bubble sensor) downstream of the preparation vessel, which may be used to monitor when all liquid has exited the preparation vessel and flowed toward downstream components such as the constriction cartridge; and (c) one or more level sensors on and/or in preparation vessel housing 1510 configured to sense a level of fluid in the preparation vessel while it is in preparation vessel housing 1510. In some embodiments, one or more of these components may be used to sense flow of fluid to and/or from preparation vessel housing 1510 and/or to sense a level of fluid in a preparation vessel inside preparation vessel housing 1510. Sensing these characteristics may, in some embodiments, be used to implement one or more automated aliquot functionalities, such as when it is desired to process some of the fluid in an input bag and/or preparation vessel at one time in one manner and to process the rest of the fluid at another time and/or in another manner.

Constriction cartridge 1524 may be any structure configured to contain or to house a component having a constricting component, such as a constricting filter (containing one or more constricting microfluidic pores) or a constricting microfluidic chip (containing one or more constricting microfluidic channels). In some embodiments, constriction cartridge 1524 may share any one or more characteristics in common with any one or more constriction cartridges discussed above with reference to FIGS. 1, 5A, and/or 5B; constriction cartridge 700 discussed above with reference to FIGS. 7A-7C; and/or constriction cartridge 800 discussed above with reference to FIGS. 8A-8D. As with other constriction cartridges discussed herein, constriction cartridge 1524 may receive the flow of prepared cell suspension downstream from a preparation vessel and cause the cell suspension to flow through one or more constricting components, such as any component containing a constricting channel, passage, or other small opening, such as a constricting filter or constricting chip contained inside constriction cartridge 1524. After passing through the constricting component, the suspension may flow out of the constriction cartridge toward one or more downstream components of system 1500, such as an output bag.

Output bag 1512 may be fluidly connected to constriction cartridge 1524 and configured to receive flow of fluid, such as cell suspension fluid, from constriction cartridge 1524. Output bag 1512 may share any one or more characteristics in common with output bags 112 and 114, as discussed above with reference to system 100 and FIG. 1.

Output bag tray area 1511 may be a platform, flat space, or other area included in system 1500 configured to allow an output bag, such as output bag 1512, to rest on the area during use of system 1500, including before, during, and/or after the output bag is filled. In some embodiments, output bag tray area 1511 may share any one or more characteristics in common with output bag tray 111, as discussed above with reference to system 100 and FIG. 1. As shown in FIG. 15A, output bag tray area may be formed integrally as part of housing 1503; alternately or additionally, in some embodiments, an output bag tray area may be formed as part of a base plate such as base plate 1502.

In some embodiments, output bag tray area 1511 may comprise a temperature control system. In some embodiments, the temperature control system of output bag tray area 1511 may share any one or more characteristics in common with any of the components of and/or associated with temperature control module 118 discussed above with respect to FIG. 1 and/or with the temperature control system of preparation vessel housing 1510 discussed above with respect to FIG. 15. In some embodiments, the temperature control system of output bag tray area 1511 may comprise any one or more components configured to heat and/or cool fluid inside output bag 1512 while output bag 1512 rests on output bag tray area 1511, such as one or more forced-air heaters, one or more forced-air coolers, one or more thermoelectric cooling devices (e.g., Peltier coolers), one or more resistive heating devices, one or more liquid heating devices, one or more liquid cooling devices, or the like. In some embodiments the temperature control system of output bag tray area 1511 may comprise a heating plate, which may be disposed on the surface of and/or integrated into the flat surface of output bag tray area 1511. A heating plate, or other temperature control component integrated into or associated with output bag tray area 1511, may in some embodiments be used to heat the output sample to at or greater than room temperature, 35 degrees Celsius, 37 degrees Celsius, 39 degrees Celsius, and/or to any temperature greater than the temperature at which the cells are processed by system 1500.

In some embodiments, output bag tray area 1511 may comprise a cover configured to cover output bag 1512, thereby shielding it from physical contact, airborne contaminants, and/or light. In some embodiments, a cover for an output bag tray may be a removable and/or replaceable lid, such as a lid mounted on a hinge and/or a slide track.

In some embodiments, output bag tray area 1511 may comprise, and/or system 1500 may comprise, one or more agitation devices configured to agitate output bag 1512 while it rests on output bag tray area 1511. In some embodiments, the one or more agitation devices may share any one or more characteristics in common with other agitation devices discussed herein, including but not limited to one or more shaker plates, vibrating devices, stirring devices, sonic agitation devices, peristaltic pump devices, gas/diaphragm devices, or other mechanisms configured to cause shaking/vibration of output bag 1512 and/or agitation/circulation of the fluid therein.

Display 1520 may be any display, such as a touch-screen display, configured to display one or more graphical elements and/or graphical user interfaces regarding operation of system 1500. In some embodiments, display 1520 may share any one or more characteristics in common with display 120 discussed above with reference to FIG. 1. Display 1520 may be used, in some embodiments, to control any one or more functions of system 1500, including by displaying and/or including by accepting user inputs, as discussed above, via the user interface described with respect to FIG. 14.

As shown in FIG. 15B, system 1500 may comprise door 1522, which may be any door, access hatch, or the like that is configurable to be movable between an open and closed position to allow access to one or more components located inside housing 1503. In the example of FIG. 15B, door 1522 is located on the side and/or rear of housing 1503.

Figure 16:
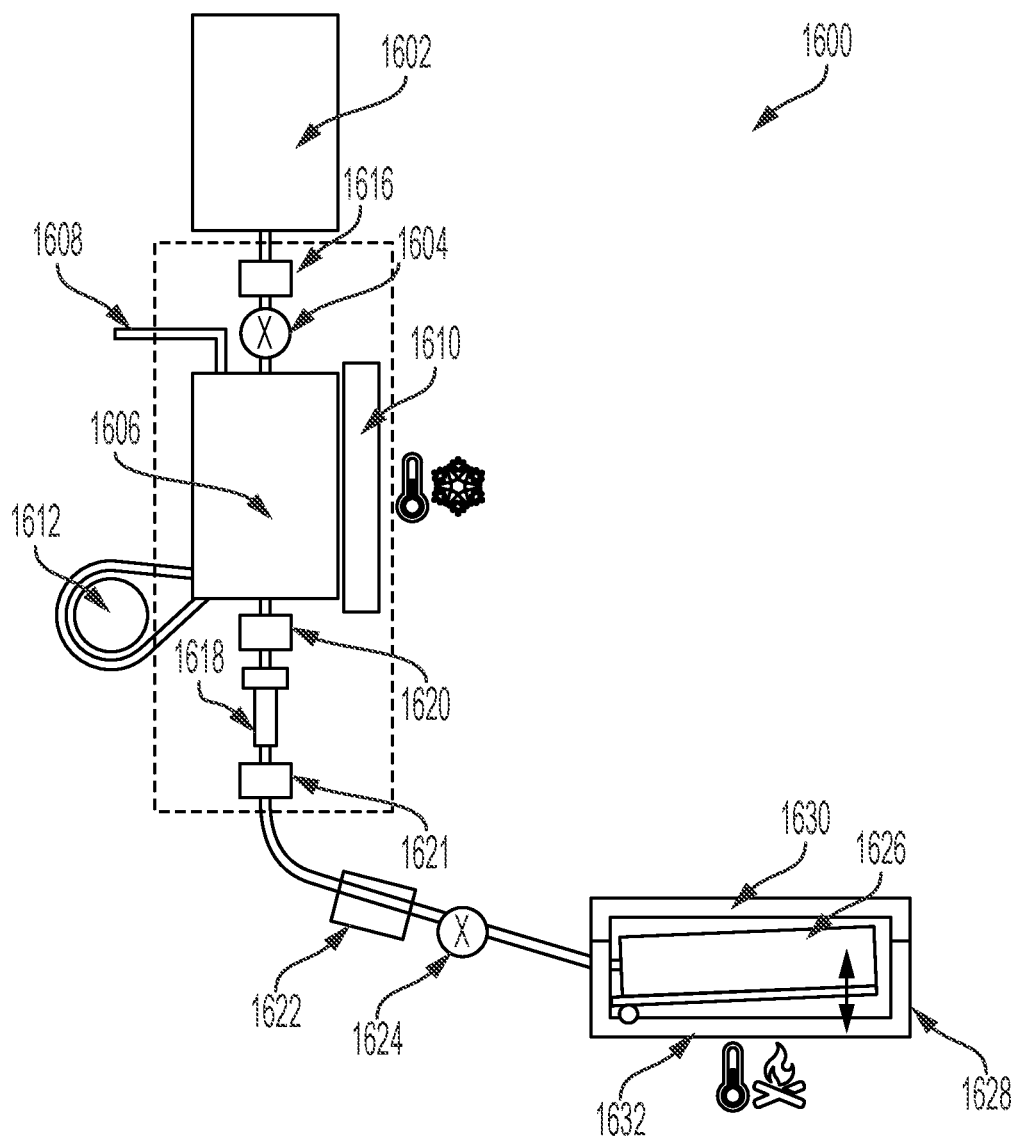
FIG. 16 illustrates a schematic representation of a tabletop system for delivering a payload to a cell, in accordance with some embodiments.

FIG. 16 illustrates a schematic representation of a tabletop system 1600 for delivering a payload to a cell, in accordance with some embodiments. In some embodiments, system 1600 may share some or all characteristics in common with system 100 described above with respect to FIG. 1 and/or with system 1000 described above with respect to FIG. 10.

Rather than depicting the physical shape of various components of the system for delivering a payload to a cell, FIG. 16 primarily schematically depicts the flow paths and associated components for fluid (e.g., cell suspension, buffer fluid) traveling through the system and for pressurized gas traveling through the system. That is, FIG. 16 depicts the various components through which cell suspension and/or buffer fluid may flow while being processed by the system, and depicts the various components through which gas (e.g., pressurized gas) may flow when being passed through the system. FIG. 16 shows components fluidly connected to one another via representation of tubing, piping, or the like connecting the representations of the components; where not otherwise noted, any suitable tubing or piping may be used to fluidly connect the various components, such as flexible plastic tubing, rigid plastic tubing, PVC tubing, metal tubing, or the like.

System 1600 may comprise input bag 1602, which may share some or all characteristics in common with input bag 1506, and/or with any other input bag described herein. In some embodiments, an input bag may be 1 L in volume, 2 L in volume, 3 L in volume. In some embodiments, a flow path of liquid flowing through system 1600 may originate (or part of it may originate) with input bag 1602.

System 1600 may comprise first flow sensor 1616, which may share any one or more characteristics in common with flow sensor 912 discussed above with reference to FIGS. 9C and 9D and/or with flow sensor 1062 discussed above with respect to FIG. 10. Flow sensor 1616 may be configured to detect when flow of fluid has stopped, thereby allowing system 1600 to determine when an input bag is empty and/or when all of a fluid sample has flowed from an input bag (e.g., bag 1602) into a preparation vessel (e.g., bag 1606).

System 1600 may comprise upper automated tubing occlusion 1604, which may be any valve, clamp, cap, or the like used to control flow of fluid from input bag 1602. Automated tubing occlusion 1604 may be automatically (e.g., electronically) controlled to allow or disallow flow of fluid in accordance with instructions executed by a processor of system 1500, such that manual actuation by a user is not required. In some embodiments, manual tubing occlusions operated by hand may be used.

System 1600 may comprise reservoir bag 1606, which may share some or all characteristics in common with the preparation vessel in the form of a flexible bag discussed above with reference to system 1500 in FIG. 15; with any of the flexible bags described below with reference to FIGS. 17, 18, and/or 19; and/or with any flexible bag serving as a preparation vessel described herein. As shown by the dotted lines surrounding reservoir bag 1606, reservoir bag 1606 and several other components, reservoir bag 1606 may be located inside a preparation vessel housing such as preparation vessel housing 1510.

System 1600 may comprise gas pressure inlet 1608, which may be any opening or inlet configured to allow gas to flow into reservoir bag 1606. As discussed above, a preparation vessel in the form of a flexible bag may be filled with pressurized gas (e.g., sterile gas and/or air) in order to cause the bag to expand and to contact the interior walls of a preparation vessel housing. Gas pressure inlet 1608 may be used to direct the flow of gas into reservoir bag 1606 for said pressurization and subsequent flow through a constriction cartridge.

System 1600 may comprise temperature control system 1610, which may share some or all characteristics in common with the temperature control system of preparation vessel housing 1510 described above with respect to FIG. 15, and/or with any other temperature control system described herein. In some embodiments, temperature control system 1610 may be a cooling system, such as a thermoelectric cooling system, configured to cool cell suspension fluid while the fluid is inside reservoir bag 1606.

System 1600 may comprise peristaltic pump 1612, which may be configured to drive the flow of fluid through a circulation loop fluidly connected to reservoir bag 1606. By pumping fluid from reservoir bag 1606 through circulation loop and back into reservoir bag 1606, peristaltic pump 1612 may circulate fluid inside reservoir bag 1606 during preparation of the fluid, such as during a cooling process. Circulation of the fluid may promote cell mixing and/or prevent cells from settling out of suspension during the cooling process, during other preparation processes, and/or during a system pause. This may lead to more consistent performance and more uniform cell concentrations as the cell suspension fluid flows through constriction cartridge 1622.

System 1600 may comprise second flow sensor 1620, which may share some or all characteristics in common with first flow sensor 1616 described above, and/or with any one or more other flow sensors described herein. Flow sensor 1620 may be configured to detect when flow of fluid has stopped, thereby allowing system 1600 to determine when a preparation vessel/bag has been emptied, and/or when all fluid has flowed into a downstream component such as constriction cartridge 1622. In some embodiments, system 1600 may stop a system run (and/or other system process), for example by ceasing pressurization of a preparation vessel and/or by closing one or more valves, when sensor 1620 detects that flow of liquid from the preparation vessel has slowed or stopped.

System 1600 may comprise filter 1618, which may be a filter configured to remove or break up cellular aggregates and/or other debris from prepared cell suspension while allowing other fluid and single cell suspensions to pass through filter 1618 and toward constriction cartridge 1622. In some embodiments, filter 1618 may comprise a filter element housed inside an external housing, wherein filter element and external housing are configured to withstand high pressures of fluid being forced through filter 1618, including maximum pressures of greater than 40 PSI or more, 80 PSI or more, 120 PSI or more, or 160 PSI or more. In some embodiments, filter 1618 may be configured to sustain a maximum pressure of less than 40 PSI or more, 80 PSI or more, 120 PSI or more, or 160 PSI. In some embodiments, the filter element may be removable from the external housing, such that a used filter element may be removed and replaced without the need to replace the external housing as well. In some embodiments, this filtering process enabled by filter 1618 may reduce clogging of a constriction in a constricting chip and/or in a constricting filter. In some embodiments, this filtering process may reduce the occurrence of clogging by a factor of 10 or more, by a factor of 50 or more, or by a factor of 100 or more. Reducing clogging may, in some embodiments, improve system throughput (a) by preventing throughput from being reduced as system components become partially clogged, and (b) by reducing or preventing the need to abort or pause a system process to repair or replace a component that has become substantially or completely clogged.

System 1600 may comprise third flow sensor 1621, which may share some or all characteristics in common with first flow sensor 1616 and/or second flow sensor 1620 described above, and/or with any one or more other flow sensors described herein. Flow sensor 1621 may be configured to detect when flow of fluid has stopped, thereby allowing system 1600 to determine when a tubing has been emptied of fluid, and/or when all fluid has flowed through any upstream component, such as filter 1618. In some embodiments, flow sensor 1621 may be used when flushing system 1600, such as after a run is complete, to ensure that there is no longer any fluid remaining in the tubing of the system.

System 1600 may comprise constriction cartridge 1622, which may share some or all characteristics in common with constriction cartridge 1524 described above with reference to FIG. 15; with any one or more constriction cartridges discussed above with reference to FIGS. 1, 5A, and/or 5B; with constriction cartridge 700 discussed above with reference to FIGS. 7A-7C; and/or with constriction cartridge 800 discussed above with reference to FIGS. 8A-8D. As shown in FIG. 16, fluid (e.g., cell suspension fluid) may flow from filter 1618 toward and into constriction cartridge 1622, where the fluid may be forced through one or more constrictions. The fluid may then flow out of constriction cartridge 1622 and toward and into output bag 1630.

System 1600 may comprise lower automated tubing occlusion 1624, which may share some or all characteristics in common with upper automated tubing occlusion 1604, discussed above. Lower automated tubing occlusion 1624 may be any valve, clamp, cap, or the like used to control flow of fluid cartridge 1622 and to output bag 1626. Automated tubing occlusion 1624 may be automatically (e.g., electronically) controlled to allow or disallow flow of fluid in accordance with instructions executed by a processor of system 1500, such that manual actuation by a user is not required. In some embodiments, manual tubing occlusions operated by hand may be used.

System 1600 may comprise output bag 1626, which may share some or all characteristics in common with output bag 1512 discussed above with reference to FIG. 15, and/or with any one or more other output bags described herein. In some embodiments, an output bag may be 2 L in volume, 3 L in volume, or 4 L in volume. In some embodiments, a flow path of liquid flowing through system 1600 may terminate (or part of it may terminate) with output bag 1626.

System 1600 may comprise leak containment tray 1628, which may share some or all characteristics in common with output bag tray area 1511 described above with reference to FIG. 15 and/or with output bag tray 111 described above with reference to FIG. 1. In some embodiments, leak containment tray 1628 may have one or more raised edges, one or more sunken portions, one or more walls, one or more absorbent elements, and/or one or more other physical features configured to contain a leak from output bag 1626 or associated tubing.

System 1600 may comprise output bag cover 1630, which may share some or all characteristics in common with the cover associated with output bag 1512 described above with reference to FIG. 15. In some embodiments, a bag cover may shield an output bag from physical contact, airborne contaminants, and/or light. In some embodiments, a cover for an output bag may be a removable and/or replaceable lid, such as a lid mounted on a hinge and/or a slide track.

System 1600 may comprise temperature control system 1632, which may share some or all characteristics in common with the temperature control system of output bag tray area 1511 described above with reference to FIG. 15, and/or with any other temperature control system described herein. In some embodiments, temperature control system 1632 may be integrated into and or disposed on or in leak containment tray 1628, and may be configured to control a temperature of (e.g., to heat) output bag 1626 after processed suspension fluid has flowed into output bag 1626.

In some embodiments, one or more components shown in FIG. 16 may together form all or part of a disposable assembly. For example, the components may be configured for one-time use, such that they may be used to perform a payload delivery process once and then be disposed of. That is, cell suspension may flow through the flow path of system 1600 one time, and then some or all of the elements of system 1600 may be replaced before another payload delivery process is performed. In some embodiments, components of a disposable assembly may be constructed from materials that are suitable for gamma sterilization in order to be suitable for use in a sterile environment. In some alternate embodiments, components of a disposable assembly may be constructed from materials that are suitable for being sterilized by other methods, such as autoclaving or ethylene oxide sterilization. In some embodiments, components of a disposable assembly may be packaged and/or shipped together, such as being packaged and/or shipped in a sealed sterile container. In some embodiments, components of a disposable assembly may be configured to be able to be attached to other components of a system for intracellular payload delivery in a manner suitable for being performed in a sterile environment, such as by being attached by hand, without the use of tools, and/or by using sterile connector mechanisms. In the example of FIG. 16, a disposable assembly may include at least one or more of reservoir bag 1606, filter 1618, and/or cartridge 1622, as well as associated tubing. In some embodiments, one or more sensors such as one or more of flow sensors 1616, 1620, and 1621 may also be part of the disposable assembly.

Figure 17:
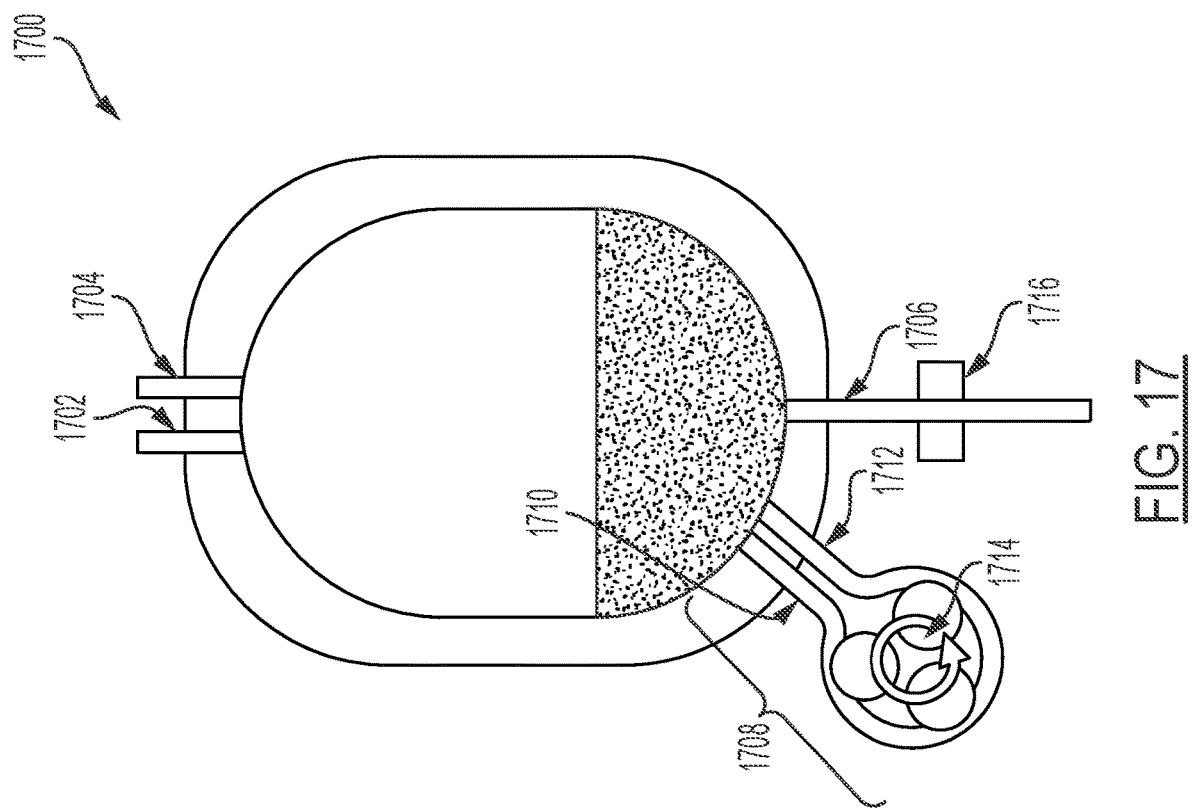
FIG. 17 illustrates a flexible bag for holding cell suspension fluid as it is prepared for passage through a constriction component of a tabletop system for delivering a payload to a cell, in accordance with some embodiments.

FIG. 17 illustrates a flexible bag 1700 for holding cell suspension fluid as it is prepared for passage through a constriction component of a tabletop system for delivering a payload to a cell, in accordance with some embodiments. Flexible bag 1700 may be configured for use as a preparation vessel in a system for delivering a payload to a cell, and may be used in some embodiments in such a system, such as systems 100, 1000, 1500, and/or 1600 as discussed above with respective reference to FIGS. 1, 10, 15, and 16. In some embodiments, flexible bag 1700 may share any one or more characteristics in common with flexible bags described elsewhere herein, such as flexible bag the preparation vessel in the form of a flexible bag described above with reference to preparation vessel housing 1510 in FIG. 15 and/or reservoir bag 1606 described above with reference to FIG. 16; in some embodiments, flexible bag 1700 may be used in a same or similar manner as any one or more of those bags otherwise described herein.

In some embodiments, flexible bag 1700 (and/or any other bag disclosed herein) may be made of PVC, silicone, Thermoplastic elastomers (TPE), or any other suitable material. In some embodiments, flexible bag 1700 may be flexible (e.g., bendable) and/or elastic (e.g., stretchable). In some embodiments, flexible bag 1700 may be flexible but not elastic. In some embodiments, a bag used in systems described herein may be elastic but not flexible. In some embodiments, bags used in systems described herein may be wholly or partially flexible and/or elastic, and/or wholly or partially inflexible and/or inelastic. For example, in some embodiments, a bag may be movable between a flattened configuration and an expanded configuration without stretching and/or without one or more portions of the bag flexing. In some embodiments, flexible bag 1700 may have one or more dimensions configured to be larger than a preparation vessel housing into which the bag is inserted, such that the bag may be pressurized and expand to touch the internal walls of the preparation vessel housing without reaching full tension and/or without the need to stretch.

Bag 1700 may have a bag wall thickness selected in accordance with requirements for strength and flexibility of the bag. In some embodiments, one or more physical characteristics or dimensions of bag 1700 may be selected such that bag 1700 will not fail (e.g., rupture) during use in one or more of the systems described herein.

In some embodiments, bag 1700 may have a bag wall thickness of greater than 0.2 mm, 0.3 mm, 0.4 mm, or 0.5 mm. In some embodiments, bag 1700 may have a bag wall thickness of less than 0.2 mm, 0.3 mm, 0.4 mm, or 0.5 mm.

In some embodiments, bag 1700 may have an edge weld thickness of greater than 0.4 mm, 0.5 mm, 0.6 mm, or 0.7 mm. In some embodiments, bag 1700 may have an edge weld thickness of less than 0.4 mm, 0.5 mm, 0.6 mm, or 0.7 mm.

In some embodiments, bag 1700 may have an edge weld width of greater than 2 mm, 3 mm, 4 mm, 5 mm or 6 mm. In some embodiments, bag 1700 may have an edge weld width of less than 2 mm, 3 mm, 4 mm, 5 mm or 6 mm.

In some embodiments, bag 1700 may comprise one or more welds around tubing of bag 1700. In some embodiments, tubing of bag 1700 may have an outside diameter of greater than 5 mm, 6 mm, 7 mm, 8 mm, or 9 mm. In some embodiments, tubing of bag 1700 may have an outside diameter of less than 5 mm, 6 mm, 7 mm, 8 mm, or 9 mm.

In some embodiments, bag 1700 may comprise one or more punched holes (e.g., for mounting). In some embodiments, one or more of the punched holes may be spaced apart from a weld by a distance of greater than 5 mm, 6 mm, 7 mm, 8 mm, or 9 mm. In some embodiments, one or more of the punched holes may be spaced apart from a weld by a distance of less than 5 mm, 6 mm, 7 mm, 8 mm, or 9 mm.

In some embodiments, bag 1700 may be configured to be able to withstand the application of high internal pressures while located inside a preparation vessel housing as discussed herein, such as to force fluid inside bag 1700 to exit bag 1700 and flow toward and into a constriction cartridge. In some embodiments, bag 1700 may be configured to be able to withstand the application of pressure greater than 130 psi, 140 psi, 150 psi, 160 psi, or 170 psi. In some embodiments, bag 1700 may be configured to be able to withstand the application of pressure less than 130 psi, 140 psi, 150 psi, 160 psi, or 170 psi.

In some embodiments, bag 1700 may have a volume of greater than 1 L, 2 L, 3 L, 4 L, 5 L or 10 L. In some embodiments, bag 1700 may have a volume of less than 1 L, 2 L, 3 L, 4 L, 5 L or 10 L.

In some embodiments, bag 1700 may have a generally flat shape, with a flat front side and a flat back side. In some embodiments, bag 1700 may have a tapered/sloped bottom in order to facilitate the flow of liquid toward and out of an outlet (e.g., as discussed below).

As shown in FIG. 17, flexible bag 1700 may comprise product inlet 1702, air inlet 1704, product outlet 1706, and circulation loop 1708. Bag 1700 may also be provided in conjunction with flow sensor 1716.

Product inlet 1702 may be any fluid inlet configured to allow fluid to flow into bag 1700. Product inlet 1702 may be configured to allow the flow of liquid, such as cell suspension fluid and or buffer liquid, to flow into bag 1700 during one or more cell processing processes as described herein. For example, during a buffering process, buffer liquid may flow into bag 1700 via product inlet 1702; during a cell processing preparation process, cell suspension fluid may flow into bag 1700 via product inlet 1702. Product inlet 1702 may be located on a top side or near a top of bag 1700, such that liquid product (e.g., cell suspension and/or buffer liquid) entering bag 1700 may enter bag 1700 from the top side under the force of gravity and fall to the bottom of the bag. In some embodiments, product inlet 1702 may share any one or more characteristics in common with one or more of vessel inlets 604 described above with reference to FIG. 6.

Gas inlet 1704 may be any fluid inlet configured to flow into bag 1700. Gas inlet 1704 may be configured to allow the flow of gas, such as pressurized gas (e.g., sterile gas, pressurized air, etc.), to flow into bag 1700 during one or more pressurization processes as described herein. For example, during cooling of fluid inside bag 1700 while bag 1700 is inside a preparation vessel housing, gas may be caused to flow into bag 1700 through gas inlet 1704, thereby causing bag 1700 to expand and to come into contact with the inner walls of the preparation vessel housing in order to facilitate effective cooling and force the cell suspension fluid out of product outlet 1706. Gas inlet 1704 may be located on a top side or near a top of bag 1700, such that gas entering bag 1700 does not bubble through liquid resting in the bottom of the bag. In some embodiments, Gas inlet 1704 may share any one or more characteristics in common with one or more of vessel inlets 604 described above with reference to FIG. 6.

Product outlet 1706 may be any fluid outlet configured to allow fluid to flow out of bag 1700. Product outlet 1706 may be configured to allow the flow of liquid, such as cell suspension fluid and/or buffer liquid, to flow out of bag 1700 during one or more cell processing processes as described herein. For example, during a buffering process, buffer liquid may flow out of bag 1700 via product outlet 1706; during a cell processing preparation process, cell suspension fluid may flow out of bag 1700 via product outlet 1706. Product outlet 1706 may be located on a bottom side or near a bottom of bag 1700, such that liquid product (e.g., cell suspension fluid and/or buffer liquid) exiting bag 1700 may be forced out of outlet 1706 under force of gravity and/or the force of pressurized gas pressing downward on bag 1700. In some embodiments, product outlet 1706 may share any one or more characteristics in common with one or more of vessel outlet 606 described above with reference to FIG. 6.

Circulation loop 1708 may be any one or more components of bag 1700 configured to cause fluid in bag 1700 to circulate and/or recirculate through a fluid pathway, such as to mix the fluid, create turbulent flow, or otherwise physically agitate the fluid. In the example of FIG. 17A, circulation coop 1708 comprises a tubing loop forming a flow path out of the main body of bag 1700 at circulation outlet 1710 and back into the main body of bag 1700 at circulation inlet 1712. Openings 1710 and 1712 may share any one or more characteristics in common with other outlets and inlets (e.g., tubing or piping outlets or inlets) described herein. The flow path of circulation loop 1708 may comprise one or more of piping or tubing In the example shown in FIG. 17, circulation outlet 1710 are each located near a bottom of bag 1700, such that liquid may be drawn from bag 1700 from below a fill level even when the liquid is at a very low fill level in the bag (e.g., less than 10% full, less than 5% full, or less than 2.5% full). Similarly placing circulation inlet 1712 near a bottom of bag 1700 may allow liquid to be recirculated into the main body of bag 1700 below the same or similar low fill lines, such that liquid may re-enter bag 1700 below the surface of the liquid in the main body of the bag. In some alternate embodiments, one or both of circulation outlet 1710 and circulation inlet 1712 may be located elsewhere on bag 1700. For example, in some alternate embodiments, circulation outlet 1710 may be located near a bottom of bag 1700, while circulation inlet 1712 may be located near a top of bag 1700, such that a recirculation loop may cause fluid to flow from near the bottom of bag 1700 to near the top of bag 1700 (e.g., causing liquid to drop back into the main body of bag 1700 under force of gravity).

Flow through a circulation loop such as circulation loop 1708 may be driven by pump 1714, which may be any pump configured to cause fluid flow through loop 1708, and in some embodiments may be a peristaltic pump. In some embodiments, a flow rate though circulation loop 1708 may be determined and/or set in accordance with a sample volume (e.g., a volume of fluid and/or of liquid inside bag 1700). In some embodiments, a circulation rate may be automatically determined by a system in which bag 1700 is disposed, such as by being determined in accordance with data read from one or more sensors of the system (e.g., data indicating fluid volume inside bag 1700), while in some embodiments a user of a system may enter a user input setting a desired circulation rate. In some embodiments, a circulation rate of bag 1700 may be greater than 100 mL/minute, 200 mL/minute, 300 mL/minute, 400 mL/minute, 500 mL/minute, or 600 mL/minute. In some embodiments, a circulation rate of bag 1700 may be less than 100 mL/minute, 200 mL/minute, 300 mL/minute, 400 mL/minute, 500 mL/minute, or 600 mL/minute. In some embodiments, a circulation loop of a bag, such as bag 1700 or any other bag or preparation vessel disclosed herein, may be configured to circulate more than 10%, 20%, 25%, 30%, 40%, 50%, or 99% of the volume of liquid in the bag during a preparation process. In some embodiments, a circulation loop of a bag, such as bag 1700 or any other bag or preparation vessel disclosed herein, may be configured to circulate less than 10%, 20%, 25%, 30%, 40%, 50%, or 99% of the volume of liquid in the bag during a preparation process.

Flow sensor 1716 may be provided in conjunction with bag 1700, and may be any sensor configured to detect flow, lack of flow, and/or flow rate in association with bag 1700.

As shown in FIG. 17, flow sensor 1716 may be configured to detect flow and/or flow rate of fluid flowing out of bag 1700 via product outlet 1706. In some embodiments, flow sensor 1716 may be configured to detect when liquid is flowing out of outlet 1706, and to detect when gas (e.g., bubbles) are or are not present in flow of liquid flowing out of outlet 1706. Flow sensor 1716 may share any one or more characteristics in common with any one or more other flow sensors discussed herein, including flow sensor 1616 discussed above with respect to FIG. 16. Flow sensor 1716 may be configured to detect when flow of fluid has stopped, thereby allowing a system 1600 to determine when bag 1700 has been emptied or nearly emptied of liquid to determine when a buffer process has been completed.

Figure 18:
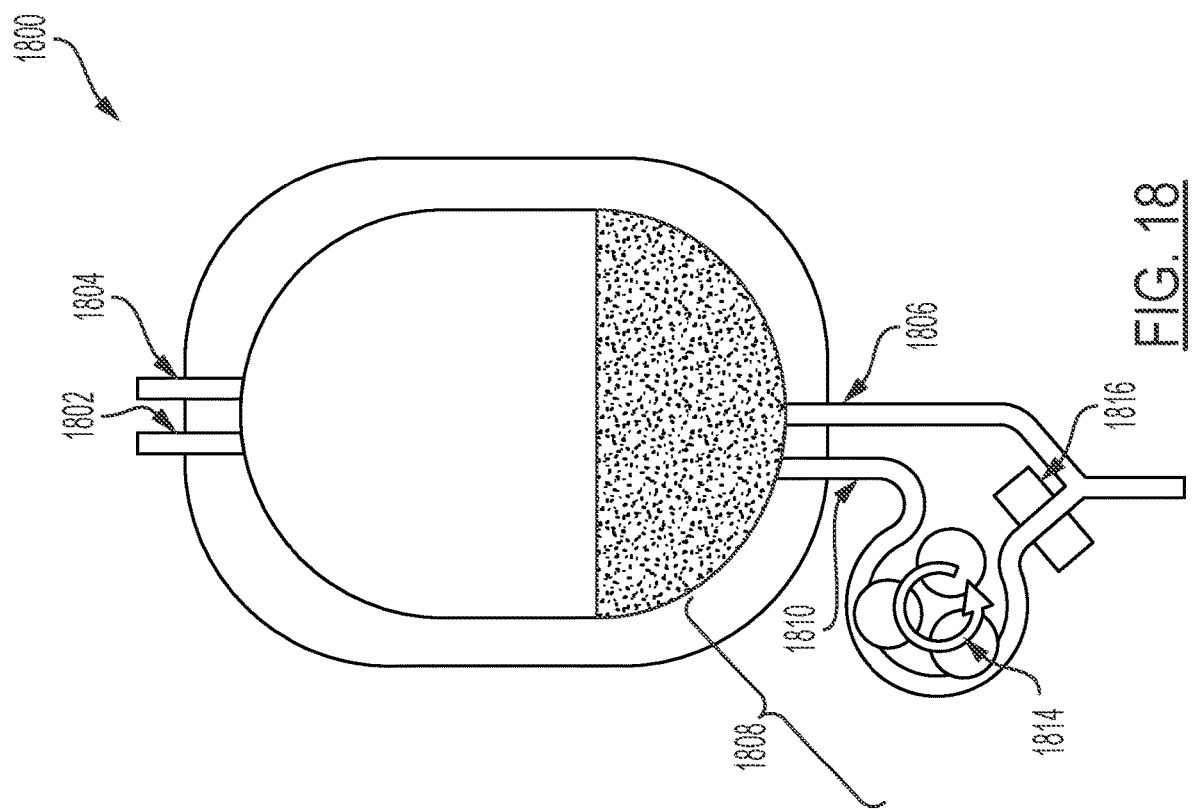
FIG. 18 illustrates a flexible bag for holding cell suspension fluid as it is prepared for passage through a constriction component of a tabletop system for delivering a payload to a cell, in accordance with some embodiments.

FIG. 18 illustrates a flexible bag 1800 for holding cell suspension fluid as it is prepared for passage through a constriction component of a tabletop system for delivering a payload to a cell, in accordance with some embodiments. As shown in FIG. 18, flexible bag 1800 may comprise product inlet 1802, air inlet 1804, product outlet 1806, circulation loop 1808, pump 1814, and flow sensor 1816. Bag 1800 may also be provided in conjunction with flow sensor 1816. In some embodiments, bag 1800 may share any one or more characteristics in common with bag 1700 described above with reference to FIG. 17, and/or with any other flexible bags described herein.

In some embodiments, flexible bag 1800 may differ from flexible bag 1700 in that a circulation loop of bag 1800 may be integrated into the product outlet of bag 1800. That is, while circulation loop 1708 has a dedicated circulation inlet 1710 and circulation outlet 1712, circulation loop 1808 has a dedicated circulation inlet 1810, but does not have a dedicated circulation outlet. Rather, the outlet for circulation loop 1808 is product outlet 1806, which serves both as the return path for fluid circulating in circulation loop 1808 and as the output path for product exiting bag 1800. This is achieved by joining the flow path for circulation loop 1808 into the flow path of outlet 1806 with a t-joint or y-joint. As further shown in FIG. 18, flow sensor 1816 may be provided along a portion of tubing/piping downstream from pump 1814 and upstream of the joint at which loop 1808 joins the flow path of outlet 1806.

In some embodiments, bag 1700 may be referred to as a "five-port" bag, due to the five different inlet/outlet ports on the bag, whereas bag 1800 may be referred to as a "four-port" bag, due to the four different inlet/outlet ports on the bag. As explained above, a four-port bag may have one fewer port than a five-port bag due to the integration of the circulation loop and the product outlet.

FIG. 19A-19D illustrate a flexible bag 1900 for holding cell suspension fluid, during execution of four different functions of a tabletop system for delivering a payload to a cell, in accordance with some embodiments. Flexible bag 1900 may comprise product inlet 1902, air inlet 1904, product outlet 1906, circulation loop 1908, pump 1914, and flow sensor 1916. Flexible bag 1900 may be a four-port bag as discussed above with reference to bag 1800 in FIG. 18, and bag 1900 and its components may share any one or more characteristics in common with bag 1800 and its respective components. FIGS. 19A-19D illustrate bag 1900 at four different phases of cell processing using bag 1900 in a system for delivering a payload to a cell; the four stages are discussed below.

FIG. 19A shows bag 1900 while bag 1900 is filling with product (e.g., filling with cell suspension liquid). As shown, the sample product may enter bag 1900 through product inlet 1902, and air and/or other gas may exit bag 1900 through air inlet 1904 as bag 1900 fills with liquid and the air/gas is displaced. Flow through inlet 1902 and/or through air inlet 1904 may be controlled by one or more manually and/or automatically controlled valves or flow control mechanisms.

FIG. 19B shows bag 1900 while the product (e.g., cell suspension liquid) in bag 1900 is full and being cooled and/or otherwise prepared for passage through a constriction cartridge. As shown, pump 1914 may be activated and the product may be drawn into and circulated through circulation loop 1908, traveling counter-clockwise around pump 1914, past flow sensor 1916, and upward from the y-joint/t-joint back toward and into the main body of bag 1900. During this circulation process, flow of product downward from the y-joint/t-joint (e.g., toward and into a filter, constriction cartridge, and/or other downstream component) may be prevented by the closure of one or more manually and/or automatically controlled valves or flow control mechanisms that may be positioned downstream of the y-joint/t-joint and upstream of a filter, constriction cartridge, and/or other downstream component.

Figure 19D:
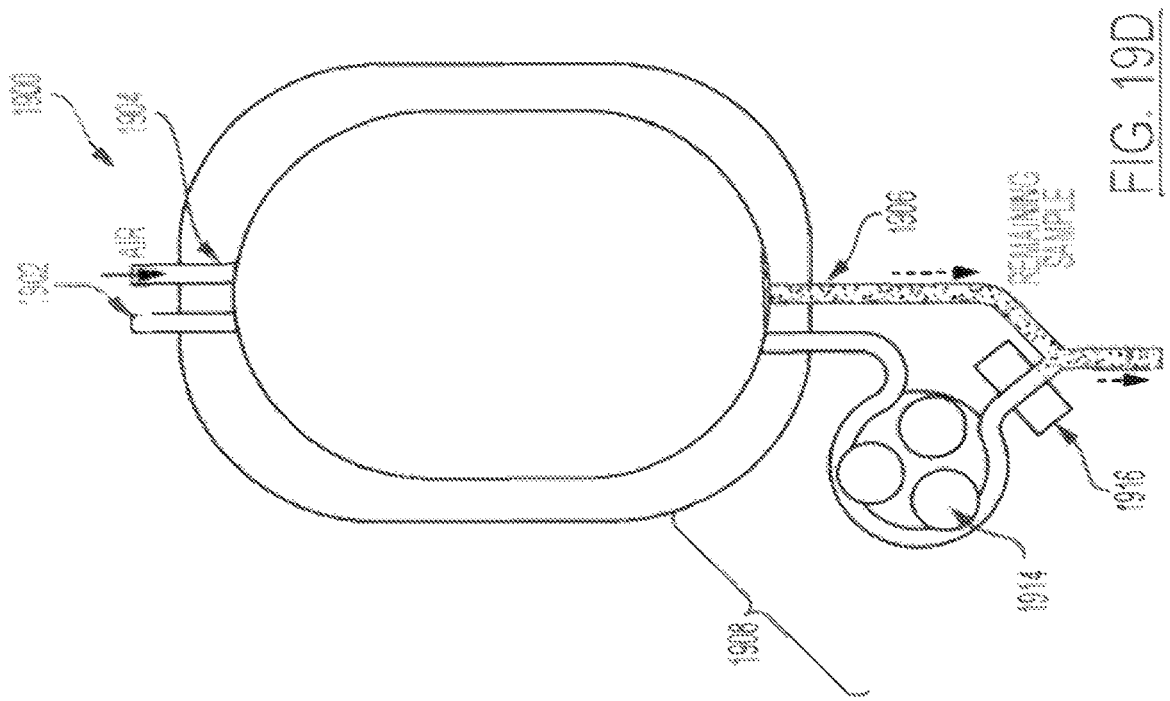
Figure 19C:
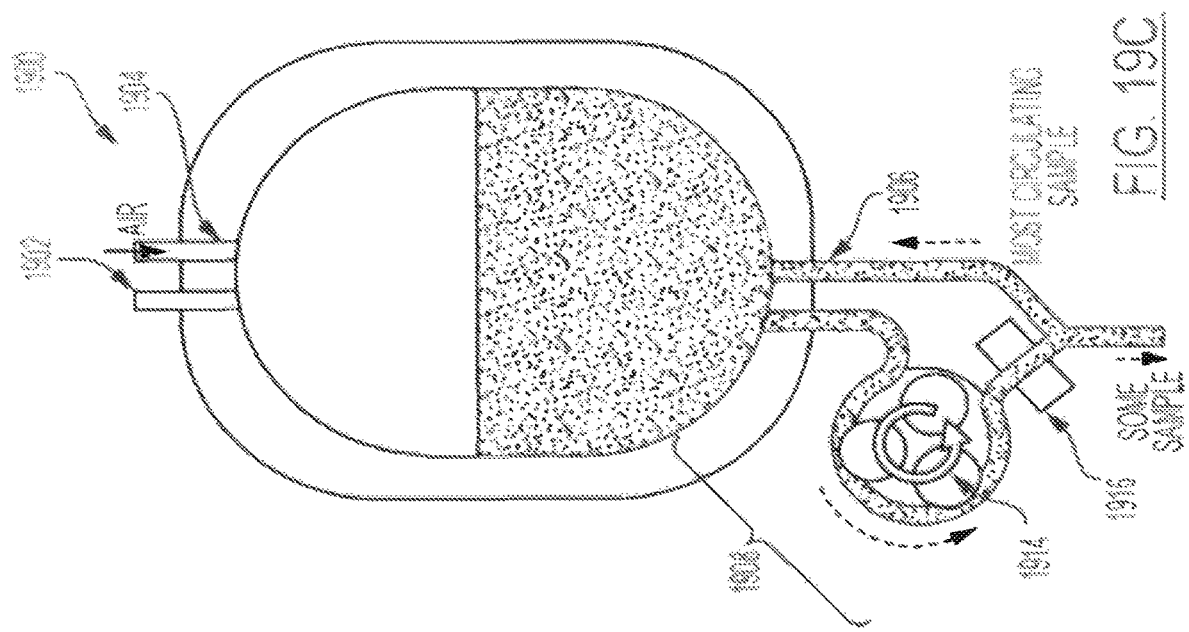

FIG. 19C shows bag 1900 while the product (e.g., cell suspension liquid) is flowing toward, into, and/or through a constriction cartridge following cooling and/or following other preparation. As shown, pump 1914 may remain activated and some product may continue to be drawn into and circulated through circulation loop 1908, traveling counter-clockwise around pump 1914, past flow sensor 1916, and upward from the y-joint/t-joint back toward and into the main body of bag 1900. However, some product may also flow downward from the y-joint/t-joint toward, into, and/or through a constriction cartridge (or other downstream component). In some embodiments, flow of product downward from the y-joint/t-joint (e.g., toward and into a filter, constriction cartridge, and/or other downstream component) may be enabled by the opening of one or more manually and/or automatically controlled valves or flow control mechanisms. In some embodiments, a circulation rate for the circulation loop may be higher than the rate of flow through a filter, constriction cartridge, or other downstream component; accordingly, a majority of the product may flow upward from the y-joint/t-joint while a minority of the product may flow downward from the y-joint/t-joint.

FIG. 19D shows bag 1900 at the end of the process for causing product (e.g., cell suspension liquid) is flowing toward, into, and/or through a constriction cartridge. In some embodiments, flow sensor 1916 may detect when air or other gas enters circulation loop 1908, thereby indicating that the main body of bag 1900 is empty or nearly empty. In response to detecting air entering circulation loop 1908, the system in which bag 1900 is disposed may automatically deactivate pump 1914, allowing remaining sample in the return path to drain downward and out of outlet 1906, toward and into downstream components. Shutting off pump 1914 in this manner may prevent bubbles from being recirculated into the main body of bag 1900 when bag 1900 is early emptied of liquid.

While FIGS. 19A-19D show a four-port bag, circulation of a sample through a circulation loop may also be performed using a five-port bag, such as bag 1700 shown in FIG. 17, in which the circulation loop is separate from the output flow path. In a five-port bag, one or more flow sensors may monitor flow of fluid in a flow path of a circulation loop (e.g., loop 1708), to determine when fluid has drained from the bag to a sufficiently low level that fluid is no longer circulating through the loop (e.g., the level of fluid has dropped below the circulation loop). Upon determining that fluid is no longer circulating through the loop, a pump causing flow of fluid through the loop may be deactivated so that the remaining fluid may drain through the output flow path. Alternately or additionally, one or more flow sensors may monitor flow of fluid through the output flow path, and circulation of fluid through the circulation loop may be ceased only when the flow sensor monitoring flow in the output flow path determines that fluid is no longer flowing through the output flow path, thereby indicating that the bag has been emptied.

In some embodiments, using any one or more of the systems or methods disclosed herein may enable improved throughput for processing cells for delivering payloads to cells. In some embodiments, a system such as any one or more of the systems disclosed herein (e.g., system 100, system 1500, etc.) may be configured to process more than 1 billion cells per minute, 10 billion cells per minute, 100 billion cells per minute, 1 trillion cells per minute, or 10 trillion cells per minute. In some embodiments, a system such as any one or more of the systems disclosed herein (e.g., system 100, system 1500, etc.) may be configured to process fewer than 1 billion cells per minute, 10 billion cells per minute, 100 billion cells per minute, 1 trillion cells per minute, or 10 trillion cells per minute. In some embodiments, a system such as any one or more of the systems disclosed herein (e.g., system 100, system 1500, etc.) may be configured to process greater than 1 billion cells per system run (e.g., per time using the system without replacing an input bag and/or refilling a preparation vessel), 10 billion cells per system run, 100 billion cells per system run, 1 trillion cells per system run, 10 trillion cells per system run, or 100 trillion cells per system run. In some embodiments, a system such as any one or more of the systems disclosed herein (e.g., system 100, system 1500, etc.) may be configured to process fewer than 1 billion cells per system run, 10 billion cells per system run, 100 billion cells per system run, 1 trillion cells per system run, 10 trillion cells per system run, or 100 trillion cells per system run. In some embodiments, throughput rates per unit time and/or throughput capabilities per system run may be dependent on cell size; for example, smaller cells such as red blood cells may process faster than larger cells such as peripheral blood mononuclear cells.

In some embodiments, any one or more of the sensors described herein (e.g., flow sensors, temperature sensors, pressure sensors, etc.) may be provided as an integrated part of a system such as any one or more of the systems disclosed herein (e.g., system 100, system 1500, etc.). In some embodiments, alternately or additionally, any one or more of the sensors described herein (e.g., flow sensors, temperature sensors, pressure sensors, etc.) may be provided as part of a removable, replaceable, modular, and/or disposable component, such as a disposable assembly, configured to be inserted into, be electronically and/or physically coupled with, and/or to otherwise interact with any one or more of the systems disclosed herein (e.g., system 100, system 1500, etc.).

Computer

Figure 20:
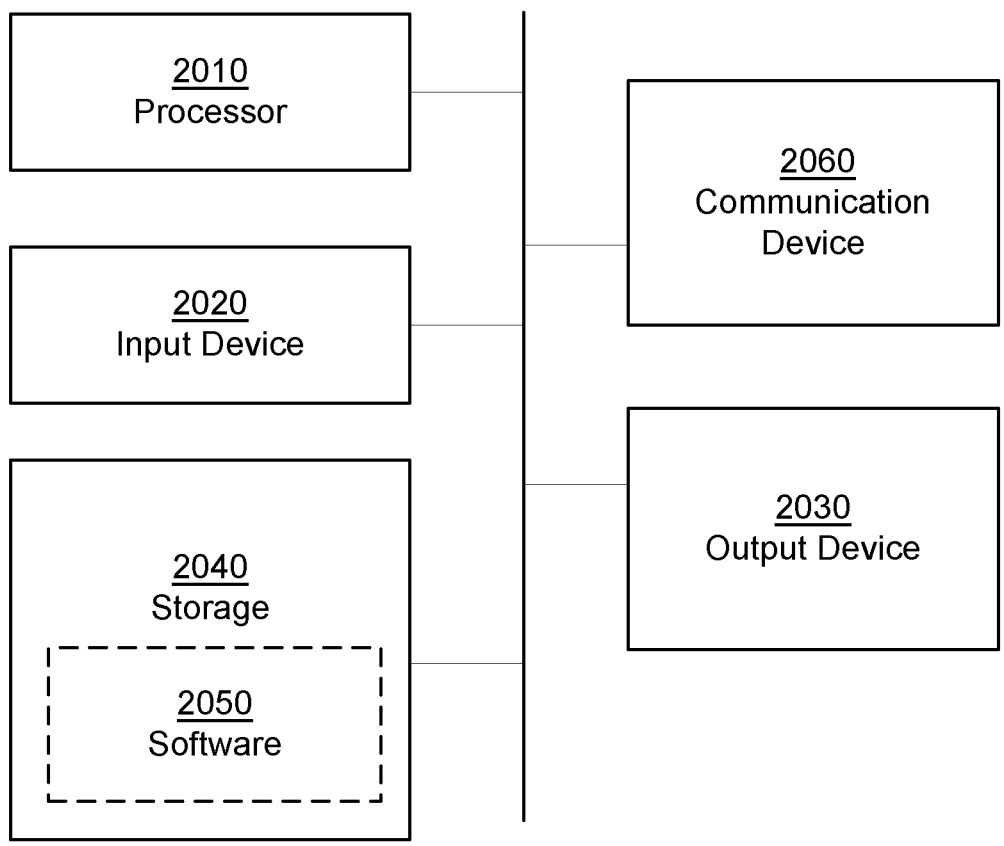
FIG. 20 is a computer, in accordance with some embodiments.

FIG. 20 illustrates an example of a computer, in accordance with some embodiments. Computer 2000 can be a component of any of the systems or electronic devices described herein. For example, computer 2000 can be a computing device included in system 100, system 1000, system 1100, system 1500, system 1600, and/or in any associated electronic device and/or any other electronic device disclosed herein. In some embodiments, computer 2000 may be configured to execute all or part of any of the methods described herein, such as all or part of methods 1200 or 1300.

Computer 2000 can be a host computer connected to a network. Computer 2000 can be a client computer or a server. As shown in FIG. 20, computer 2000 can be any suitable type of microprocessor-based device, such as a personal computer; workstation; server; or handheld computing device, such as a phone or tablet. The computer can include, for example, one or more of processor 2010, input device 2020, output device 2030, storage 2040, and communication device 2060.

Input device 2020 can be any suitable device that provides input, such as a touch screen or monitor, keyboard, mouse, or voice-recognition device. Output device 2030 can be any suitable device that provides output, such as a touch screen, monitor, printer, disk drive, or speaker.

Storage 2040 can be any suitable device that provides storage, such as an electrical, magnetic, or optical memory, including a RAM, cache, hard drive, CD-ROM drive, tape drive, or removable storage disk. Communication device 2060 can include any suitable device capable of transmitting and receiving signals over a network, such as a network interface chip or card. The components of the computer can be connected in any suitable manner, such as via a physical bus or wirelessly. Storage 2040 can be a non-transitory computer-readable storage medium comprising one or more programs, which, when executed by one or more processors, such as processor 2010, cause the one or more processors to execute all or part of any of the methods or techniques described herein, such as all or part of methods 1200 or 1300.

Software 2050, which can be stored in storage 2040 and executed by processor 2010, can include, for example, the programming that embodies the functionality of the present disclosure (e.g., as embodied in the systems, computers, servers, and/or devices as described above). In some embodiments, software 2050 can be implemented and executed on a combination of servers such as application servers and database servers.

Software 2050 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 2040, that can contain or store programming for use by or in connection with a system, apparatus, or device.

Software 2050 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 2000 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 2000 can implement any operating system suitable for operating on the network. Software 2050 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Embodiments

Below is an enumerated listing of certain embodiments. In some embodiments, any one or more of the features of any one or more of the embodiments below may be combined with any one or more of the other embodiments, even if the dependencies of the embodiments do not explicitly indicate that the embodiments may be combined.

1. A system for delivering a payload to a cell, the system comprising:
   a platform supporting:
      a holder configured to hold a cell suspension input container containing a cell suspension comprising cells;
      a receiver configured to receive all or part of a disposable assembly, the disposable assembly comprising:
         a preparation vessel configured to be in fluid communication with the input container and to hold the cell suspension as it is prepared for passage through one or more cell-deforming constrictions; and
         a constriction cartridge configured to be in fluid communication with the preparation vessel, the constriction cartridge configured to house a component comprising the one or more cell-deforming constrictions, wherein the cell-deforming constrictions are configured to cause perturbations in a cell membrane of the cell to allow entry of a payload into the cell; and
      one or more processors configured to receive input from a user and to control one or more control modules, the one or more control modules configured to control one or more of a pressure, temperature, agitation, and flow of the cell suspension, wherein the one or more control modules comprises:
         a flow control module configured to cause the cell suspension to flow from the input container through the disposable assembly to a cell suspension output container such that the payload is delivered into the cell.
2. The system of embodiment 1, wherein:
   the component comprising the one or more cell-deforming constrictions is a microfluidic chip comprising microfluidic channels, wherein the microfluidic channels comprise the one or more cell-deforming constrictions; and
   the constriction cartridge is a microfluidic chip cartridge configured to house the microfluidic chip.
3. The system of any one of embodiments 1 and 2, wherein:
   the component comprising the one or more cell-deforming constrictions is a filter comprising a plurality of cell-deforming constrictions; and
   the constriction cartridge is a filter cartridge configured to house the filter.
4. The system of any one of embodiments 1-3, wherein the platform is a tabletop platform.
5. The system of any one of embodiments 1-4, wherein the cell suspension comprises the payload.
6. The system of any one of embodiments 1-5, wherein the system is configured to cause the payload to come into contact with the cell suspension before flow of at least part of the cell suspension through the constriction cartridge.
7. The system of any one of embodiments 1-6, wherein the system is configured to cause the payload to come into contact with the cell suspension following flow of at least part of the cell suspension through the constriction cartridge.
8. The system of any one of embodiments 1-7, wherein the one or more processors are configured to cause pressure to be applied to the cell suspension inside the preparation vessel.
9. The system of embodiment 8, wherein the one or more control modules comprise a pressure-control module comprising a pressure source configured to deliver sterile gas to the preparation vessel.
10. The system of any one of embodiments 8 and 9, wherein the pressure applied to the cell suspension inside the preparation vessel is sufficient to cause the preparation vessel to come into contact with interior walls of the receiver.
11. The system of any one of embodiments 8-10, wherein the pressure applied to the cell suspension inside the preparation vessel is sufficient to cause the cell suspension to be forced out of the preparation vessel and through the constriction cartridge.
12. The system of any one of embodiments 1-11, wherein the one or more processors are configured to cause the cell suspension to be heated or cooled inside the preparation vessel.
13. The system of embodiment 12, wherein the one or more control modules comprises a temperature control module comprising one or more thermoelectric temperature control devices configured to heat or cool a part of the receiver configured to contact the preparation vessel.
14. The system of embodiment 13, wherein the part of the receiver configured to contact the preparation vessel is a conductive jacket configured to conduct heat to and from the preparation vessel.
15. The system of any one of embodiments 12-14, wherein the one or more control modules comprises a temperature control module comprising one or more thermoelectric temperature control devices configured to heat or cool the preparation vessel.
16. The system of embodiment 15, wherein the one or more thermoelectric temperature control devices comprises a cooling plate disposed in a wall of the receiver and configured to contact an outer wall of the preparation vessel when the preparation vessel is inserted into the receiver.
17. The system of any one of embodiments 1-16, wherein one or more processors are configured to cause the cell suspension to be agitated inside the preparation vessel such that cells are homogeneously distributed in the cell suspension.
18. The system of embodiment 17, wherein the one or more control modules comprises an agitation control module comprising an agitation plate configured to be driven by one or more motors, the agitation plate configured to cause agitation of all or part of the receiver.
19. The system of any one of embodiments 1-18, wherein the flow control module is configured to cause one or more valves to control flow of the cell suspension to flow from the input container through the disposable assembly to the output container.

20. The system of any one of embodiments 1-19, wherein the flow control module is configured to cause the cell suspension to flow at a target fluid speed.

21. The system of any one of embodiments 1-20, further comprising an input device configured to receive instructions from the user, wherein the one or more processors are configured to operate one or more of the control modules in response to the instructions.

22. The system of embodiment 21, wherein the input device comprises a touch-screen display configured to transmit signals to one or more of the control modules in response to detecting contact by a user.

23. The system of any one of embodiments 21 and 22, wherein the input device comprises an agitation speed adjustment device configured to control a speed of a motor that causes agitation of the cell suspension inside the preparation vessel.

24. The system of any one of embodiments 1-23, wherein the preparation vessel is configured to hold up to 10 liters of the cell suspension.

25. The system of any one of embodiments 1-24, wherein the preparation vessel is configured to allow a pressure of up to 120 psi to be applied to the cell suspension.

26. The system of embodiments 1-25, wherein the preparation vessel is configured to allow pressure of up to 120 psi be applied to the interior of the preparation vessel.

27. The system of any one of embodiments 1-26, wherein the preparation vessel comprises a first inlet configured to be fluidly connected to the cell suspension input container to receive flow of the cell suspension.

28. The system of any one of embodiments 1-27, wherein the preparation vessel comprises a second inlet configure to be fluidly connected to a pressure source to receive flow of sterile gas to the preparation vessel in order to cause pressure to be applied to the cell suspension.

29. The system of any one of embodiments 1-28, wherein the preparation vessel comprises an outlet configured to be fluidly connected to the constriction cartridge.

30. The system of any one of embodiments 1-29, wherein the constriction cartridge comprises an inlet configured to be fluidly connected to the preparation vessel.

31. The system of any one of embodiments 1-30, wherein the constriction cartridge comprises a housing portion configured to hold the component comprising the one or more cell-deforming constrictions and to direct flow of the cell suspension into the component comprising the one or more cell-deforming constrictions.

32. The system of any one of embodiments 1-31, wherein the constriction cartridge is configured such that the component is held between a base portion and a removable lid portion.

33. The system of embodiment 32, wherein the removable lid portion is configured to be slidably attachable to and removable from the base portion without the use of tools.

34. The system of any one of embodiments 1-33, wherein the constriction cartridge is configured to hold the component in place by one or more o-rings.

35. The system of any one of embodiments 1-34, wherein the constriction cartridge is configured to direct flow of the cell suspension into the component through one or more o-rings.

36. The system of any one of embodiments 1-35, wherein:
the disposable assembly comprises the a cell suspension output container, which is configured to be in fluid communication with the constriction cartridge; and
the constriction cartridge comprises an outlet configured to be fluidly connected to the output container.

37. The system of any one of embodiments 1-36, wherein the one or more processors are configured to receive signals from one or more sensors and to automatically control one or more of a pressure, temperature, and agitation of the cell suspension in accordance with the signals received.

38. The system of embodiment 37, wherein the one or more sensors are included in the disposable assembly.

39. The system of any one of embodiments 37 and 38, wherein the one or more sensors comprise a temperature sensor configured to monitor a temperature of the cell suspension.

40. The system of embodiment 39, wherein the temperature sensor comprises a thermistor included in the disposable assembly and configured to be attached to the receiver.

41. The system of any one of embodiments 37-40, wherein the one or more sensors comprises a bubble sensor configured to monitor flow of the cell suspension.

42. The system of any one of embodiments 37-41, wherein the one or more sensors comprises a pressure sensor configured to monitor a pressure applied to the cell suspension.

43. The system of any one of embodiments 37-42, wherein the one or more sensors comprises a pressure sensor configured to monitor a pressure inside the preparation vessel.

44. The system of any one of embodiments 1-43, further comprising a memory configured to store log information comprising one or more of pressure, temperature, agitation, flow, and time elapsed while the cell suspension is located in one or both of the preparation vessel and the constriction cartridge.

45. The system of any one of embodiments 1-44, further comprising a display configured to display information comprising one or more of pressure, temperature, agitation, flow, and time elapsed while the cell suspension is located in one or both of the preparation vessel and the constriction cartridge.

46. The system of any one of embodiments 1-45, further comprising a network communication interface configured to transmit information to a remote computing device, the information comprising including one or more of pressure, temperature, agitation, flow, and time elapsed while the cell suspension is located in one or both of the preparation vessel and the constriction cartridge.

47. The system of any one of embodiments 1-46, wherein the system is configured to be able to be moved from a first location to a second location without disassembly.

48. The system of embodiment 47, wherein moving the system without disassembly comprises moving the platform without detaching the holder, receiver, or one or more processors from the platform.

49. The system of any one of embodiments 1-48, wherein the system is less than 2 feet in height.

50. The system of any one of embodiments 1-49, wherein the system has a footprint of less than 3 feet by 2 feet.

51. The system of any one of embodiments 1-50, wherein the system is less than 60 pounds.

52. The system of any one of embodiments 1-51, wherein the system is configured to be sterilizable.

53. The system of any one of embodiments 1-52, further comprising a filter configured to receive flow of fluid downstream from the preparation vessel and upstream of the constriction cartridge, wherein the filter is configured to remove multicellular aggregates from the cell suspension before it reaches the constriction cartridge.

54. The system of embodiment 53, wherein the filter is configured to withstand internal pressure of greater than 120 psi.

55. The system of any one of embodiments 1-54, wherein the preparation vessel comprises a flexible plastic bag.

56. The system of embodiment 55, wherein the receiver comprises a housing configured to receive the flexible plastic bag such that contents of the bag may be cooled.

57. The system of any one of embodiments 1-56, wherein the preparation vessel comprises a circulation loop configured to draw liquid from a main body of the preparation vessel and to circulate the liquid back into the main body of the preparation vessel.

58. The system of embodiment 57, wherein the circulation loop comprises a peristaltic pump configured to cause the flow of liquid through the circulation loop.

59. The system of any one of embodiments 57 and 58, wherein a portion of the circulation loop is integrated with a flow path leading from the preparation vessel to the constriction cartridge.

60. A disposable assembly for use in a system for delivering a payload to a cell, the assembly comprising:
   a preparation vessel configured to hold cell suspension as it is prepared for passage through one or more cell-deforming constrictions; and
   a constriction cartridge configured to be in fluid communication with the preparation vessel, the constriction cartridge configured to house a component comprising the one or more cell-deforming constrictions, wherein the cell-deforming constrictions are configured to cause perturbations in a cell membrane that allow entry of a payload into the cell.

61. The assembly of embodiment 60, wherein the assembly is configured to be able to be connected to and disconnected from the system without the use of tools.

62. The assembly of any one of embodiments 60 and 61, wherein:
   the component comprising the one or more cell-deforming constrictions is a microfluidic chip comprising microfluidic channels, wherein the microfluidic channels comprise the one or more cell-deforming constrictions; and
   the constriction cartridge is a microfluidic chip cartridge configured to house the microfluidic chip.

63. The assembly of any one of embodiments 60-62, wherein:
   the component comprising the one or more cell-deforming constrictions is a filter comprising a plurality of cell-deforming constrictions; and
   the constriction cartridge is a filter cartridge configured to house the filter.

64. The assembly of any one of embodiments 60-63, wherein the system is a tabletop system.

65. The assembly of any one of embodiments 60-64, wherein connecting the assembly to the system without the use of tools comprises fluidly connecting the assembly to the system such that the system may receive flow of the cell suspension from the system.

66. The assembly of any one of embodiments 60-65, wherein connecting the assembly to the system without the use of tools comprises electronically connecting one or more sensors of the assembly to one or more controllers of the system.

67. The assembly of embodiment 66, wherein the one or more sensors comprise a temperature sensor configured to monitor a temperature of the cell suspension inside the preparation vessel and to transmit data regarding the temperature to a temperature control module of the system.

68. The assembly of any one of embodiments 66 and 67, wherein the one or more sensors comprise a pressure sensor configured to monitor a pressure applied to the cell suspension and to transmit data regarding the pressure to a pressure control module of the system.

69. The assembly of any one of embodiments 66-68, wherein the pressure sensor is configured to monitor a pressure inside the preparation vessel and to transmit data regarding the pressure to a pressure control module of the system.

70. The assembly of any one of embodiments 66-69, wherein the one or more sensors comprise a bubble sensor configured to monitor flow of the cell suspension through the assembly.

71. The assembly of any one of embodiments 60-70, wherein the constriction cartridge comprises an inlet configured to be fluidly connected to the preparation vessel.

72. The assembly of any one of embodiments 60-71, wherein the constriction cartridge comprises a housing portion configured to hold the component comprising the one or more cell-deforming constrictions and to direct flow of the cell suspension into the component comprising the one or more cell-deforming constrictions.

73. The assembly of any one of embodiments 60-72, wherein the constriction cartridge is configured such that the component is held between a base portion and a removable lid portion.

74. The assembly of embodiment 73, wherein the removable lid portion is configured to be slidably attachable to and removable from the base portion.

75. The assembly of any one of embodiments 60-74, wherein the constriction cartridge is configured to hold the component in place by one or more o-rings.

76. The assembly of any one of embodiments 60-75, wherein the constriction cartridge is configured to direct flow of the cell suspension into the component through one or more o-rings.

77. The assembly of any one of embodiments 60-76, further comprising a cell suspension output container configured to be in fluid communication with an outlet of the constriction cartridge.

78. The assembly of any one of embodiments 60-77, wherein the constriction cartridge is configured to house a second component comprising one or more cell-deforming constrictions and to direct flow of the cell suspension fluid through the second component in parallel with the first component.

79. The assembly of any one of embodiments 60-78, wherein the assembly is configured to be sterilizable.

80. A method for delivering a payload to a cell, the method comprising:
   providing a cell in a cell suspension;
   passing the cell suspension into a preparation vessel at a tabletop system;
   while the cell suspension is in the preparation vessel, preparing the cell suspension including by causing pressure to be applied to the cell suspension;
   passing the prepared cell suspension from the preparation vessel through a constriction cartridge of the system, wherein the constriction cartridge is configured to house a component comprising a cell-deforming constriction that causes a perturbation in a membrane of the cell that allows entry of a payload into the cell.

81. The method of embodiment 80, wherein:
   the component comprising the one or more cell-deforming constrictions is a microfluidic chip comprising microfluidic channels, wherein the microfluidic channels comprise the one or more cell-deforming constrictions; and
   the constriction cartridge is a microfluidic chip cartridge configured to house the microfluidic chip.
82. The method of any one of embodiments 80 and 81, wherein:
   the component comprising the one or more cell-deforming constrictions is a filter comprising a plurality of cell-deforming constrictions; and
   the constriction cartridge is a filter cartridge configured to house the filter.
83. The method of any one of embodiments 80-82, further comprising causing the payload to come into contact with the cell suspension before flow of at least part of the cell suspension through the constriction cartridge.
84. The method of any one of embodiments 80-83, further comprising causing the payload to come into contact with the cell suspension following flow of at least part of the cell suspension through the constriction cartridge.
85. The method of any one of embodiments 80-84, further comprising, attaching to the system a disposable assembly comprising the preparation vessel and the constriction cartridge.
86. The method of embodiment 85, wherein attaching the disposable assembly comprises attaching the disposable assembly without the use of tools.
87. The method of any one of embodiments 85 and 86, wherein attaching the disposable assembly comprises inserting the preparation vessel into a receiver of the system configured to receive the preparation vessel.
88. The method of any one of embodiments 85-87, wherein attaching the disposable assembly comprises attaching one or more sensors included in the disposable assembly, such that the sensors are configured to send signals to the system.
89. The method of embodiment 88, wherein the one or more sensors included in the disposable assembly comprises a temperature sensor configured to monitor a temperature of the cell suspension.
90. The method of embodiment 89, wherein the temperature sensor comprises a temperature probe configured to be attached to the receiver.
91. The method of any one of embodiments 88-90, wherein the one or more sensors included in the disposable assembly comprises a bubble sensor configured to monitor flow of the cell suspension.
92. The method of any one of embodiments 88-91, wherein the one or more sensors included in the disposable assembly comprises a pressure sensor configured to monitor a pressure applied to the cell suspension.
93. The method of any one of embodiments 85-92, wherein attaching the disposable assembly comprises attaching one or more sensors included in the system to the disposable assembly, such that the sensors are configured to detect one or more characteristics regarding contents of the disposable assembly.
94. The method of embodiment 93, wherein the one or more sensors included in the system comprises a flow sensor configured to monitor flow of liquid through tubing of the disposable assembly.
95. The method of any one of embodiments 93 and 94, wherein the one or more sensors included in the system comprises a level sensor configured to monitor a fill level of the preparation vessel.
96. The method of any one of embodiments 93-95, wherein the one or more sensors included in the system comprises a temperature sensor configured to monitor a temperature of liquid in the preparation vessel.
97. The method of any one of embodiments 80-96, wherein preparing the cell suspension comprises agitating the cell suspension inside the preparation vessel to homogeneously distribute the cells in the cell suspension.
98. The method of embodiment 97, wherein agitating the cell suspension comprises monitoring agitation of the cell suspension.
99. The method of any one of embodiments 80-98, wherein preparing the cell suspension comprises heating or cooling the cell suspension inside the preparation vessel.
100. The method of embodiment 99, wherein heating or cooling the cell suspension comprises using a thermoelectric temperature control device to heat or cool part of a receiver containing the preparation vessel.
101. The method of any one of embodiments 99 and 100, wherein heating or cooling the cell suspension comprises monitoring a temperature of the cell suspension as it is heated or cooled.
102. The method of any one of embodiments 80-101, wherein causing pressure to be applied to the cell suspension comprises monitoring a pressure as it is applied to the cell suspension.
103. The method of any one of embodiments 80-102, wherein providing the cell in a cell suspension comprises providing the cell suspension in an input container.
104. The method of any one of embodiments 80-103, comprising passing the cell suspension from the constriction cartridge into an output container.
105. The method of any one of embodiments 80-104, comprising, prior to passing the cell suspension into the disposable assembly, performing an integrity check on the disposable assembly.
106. The method of embodiment 105, wherein performing an integrity check on the disposable assembly comprises pressurizing a gas inside the disposable assembly and monitoring a pressure of the pressurized gas for a predetermined period of time.
107. The method of any one of embodiments 80-106, comprising, prior to passing the cell suspension through the disposable assembly, passing a primer solution through the disposable assembly.
108. The method of any one of embodiments 80-107, further comprising:
   providing a supply of blood comprising a first plurality of types of cells;
   isolating a target type of cells from among the first plurality of types of cells;
   suspending the isolated target type of cells in a delivery material to create the cell suspension.
109. The method of embodiment 108, further comprising:
   washing processed cells following passage through the cell-deforming constriction to remove the delivery material;
   suspending the washed processed cells in a buffer material for cryopreservation.
110. The method of any one of embodiments 80-109, further comprising:
   while all or some of the cell suspension is in the preparation vessel, monitoring a fill level of the preparation vessel using one or more level sensors.

111. The method of any one of embodiments 80-110, further comprising:
while the cell suspension is in the preparation vessel, causing the cell suspension to be circulated out of a main body of the preparation vessel, through a circulation loop, and back into the main body of the preparation vessel.

112. The method of embodiment 111, further comprising:
in accordance with a determination that a fill level of the preparation vessel is below a predefined threshold, causing circulation of the cell suspension through the circulation loop to cease.

113. A system for delivering a payload through a cell membrane, the system comprising:
a preparation vessel configured to contain a cell suspension, wherein the suspension comprises cells;
a constriction cartridge fluidly connected to the preparation vessel;
a touch-screen display;
one or more processors; and
a memory configured to store instructions executable by the one or more processors to cause the system to:
detect a contact on the display at a location corresponding to an icon for initiating a process for delivering a payload through membranes of cells in the cell suspension; and
in accordance with detecting the contact:
cause a temperature of the cell suspension inside the preparation vessel to be adjusted;
cause pressure to be applied to the cell suspension inside the preparation vessel; and
pass the cell suspension from the preparation vessel through a constriction in a component housed in the constriction cartridge, wherein the constriction is a cell-deforming constriction that causes perturbations in membrane of the cells in the cell suspension that allow entry of the payload into the cells.

114. The system of embodiment 113, wherein the instructions are executable by the one or more processors to cause the system to:
while adjusting a temperature of the suspension inside the preparation vessel:
display an indication of a current pressure applied to the cell suspension;
display an indication of a current temperature of the cell suspension; and
display a dynamic indication of an elapsed time for the payload delivery process.

115. The system of embodiment 114, wherein the instructions are executable by the one or more processors to cause the system to:
while passing the cell suspension through the constriction cartridge:
continue to display the indication of a current pressure applied to the cell suspension;
continue to display the indication of a current temperature of the cell suspension;
continue to display the dynamic indication of an elapsed time for the payload delivery process; and
display a dynamic indication of an elapsed time for the process of passing the cell suspension through the constriction cartridge.

116. The system of embodiment 115, wherein the instructions are executable by the one or more processors to cause the system to:
detect that the payload delivery process is complete; and
in accordance with detecting that the payload delivery process is complete:
cease to display the dynamic indication of an elapsed time for the payload delivery process;
cease to display the dynamic indication of an elapsed time for the process of passing the cell suspension through the constriction cartridge;
display an indication of a total elapsed time for the payload delivery process; and
display an indication of a total elapsed time for the process of passing the cell suspension through the constriction cartridge.

117. The system of any one of embodiments 113-116, wherein heating or cooling the cell suspension inside the preparation vessel is performed in accordance with detecting a contact on the display at a location corresponding to an icon for performing a heating or cooling process.

118. The system of any one of embodiments 113-117, wherein causing pressure to be applied to the cell suspension inside the preparation vessel comprises delivering pressurized gas into the preparation vessel at a pressure indicated by one or more contacts detected on the display at a location corresponding to an icon for setting a pressure.

119. The system of any one of embodiments 113-118, wherein causing pressure to be applied to the cell suspension comprises delivering pressurized gas into the preparation vessel at a pressure indicated by one or more contacts detected on the display at a location corresponding to an icon for setting a pressure.

120. The system of any one of embodiments 113-119, wherein:
the instructions are executable by the one or more processors to cause the system to agitate the cell suspension inside the preparation vessel; and
agitating the cell suspension inside the preparation vessel is performed in accordance with detecting a contact on the display at a location corresponding to an icon for performing an agitation process.

121. The system of any one of embodiments 113-120, wherein the instructions are executable by the one or more processors to cause the system to:
in accordance with detecting that a disposable assembly is not connected to the system, display an instruction to connect the disposable assembly;
in accordance with detecting that the disposable assembly has been connected to the system, cease to display the instruction to connect the disposable assembly.

122. The system of embodiment 121, wherein the instructions are executable by the one or more processors to cause the system to:
in accordance with detecting that a first portion of the disposable assembly has been connected:
cease to display a first page of the instruction, wherein the first page comprises an instruction to connect the first portion of the disposable assembly; and
replace display of the first page of the instruction with display of a second page of the instruction, wherein the second page comprises an instruction to connect a second portion of the disposable assembly 123. The system of any one of embodiments 113-122, wherein the instructions are executable by the one or more processors to cause the system to:

detect a contact on the display at a location corresponding to an icon for initiating an integrity test;

in accordance with detecting the contact, initiate the integrity test and display an indication of a current pressure and an indication of an elapsed time for the integrity test.

124. The system of any one of embodiments 113-123, wherein the instructions are executable by the one or more processors to cause the system to:

detect a contact on the display at a location corresponding to an icon for initiating a priming process;

in accordance with detecting the contact:

pass a primer solution through the preparation vessel and the constriction cartridge; and display a current temperature of the primer solution during the priming process.

125. A system for delivering a payload to a cell, the system comprising:

a platform supporting:

a holder configured to hold a cell suspension input container containing a cell suspension comprising cells;

a receiver configured to receive a disposable assembly, the disposable assembly comprising:

a preparation vessel configured to be in fluid communication with the input container and to hold the cell suspension as it is prepared for passage through one or more cell-deforming constrictions; and a constriction cartridge configured to be in fluid communication with the preparation vessel, the constriction cartridge configured to house a component comprising the one or more cell-deforming constrictions, wherein the cell-deforming constrictions are configured to cause perturbations in a cell membrane of the cell to allow entry of a payload into the cell;

a cell suspension output container configured to be in fluid communication with the constriction cartridge; and one or more processors configured to receive input from a user and to control one or more control modules, the one or more control modules configured to control one or more of a pressure, temperature, agitation, and flow of the cell suspension, wherein the one or more control modules comprises:

a flow control module configured to cause the cell suspension to flow from the input container through the disposable assembly to the output container such that the payload is delivered into the cell.

126. The system of embodiment 125, wherein:

the component comprising the one or more cell-deforming constrictions is a microfluidic chip comprising microfluidic channels, wherein the microfluidic channels comprise the one or more cell-deforming constrictions; and the constriction cartridge is a microfluidic chip cartridge configured to house the microfluidic chip.

127. The system of any one of embodiments 125 and 126, wherein:

the component comprising the one or more cell-deforming constrictions is a filter comprising a plurality of cell-deforming constrictions; and the constriction cartridge is a filter cartridge configured to house the filter.

128. The system of any one of embodiments 125-127, wherein the platform is a tabletop platform.

129. The system of any one of embodiments 125-128, wherein the cell suspension comprises the payload.

130. The system of any one of embodiments 125-129, wherein the system is configured to cause the payload to come into contact with the cell suspension before flow of at least part of the cell suspension through the constriction cartridge.

131. The system of any one of embodiments 125-130, wherein the system is configured to cause the payload to come into contact with the cell suspension following flow of at least part of the cell suspension through the constriction cartridge.

132. The system of any one of embodiments 125-131, wherein the one or more processors are configured to cause pressure to be applied to the cell suspension inside the preparation vessel.

133. The system of embodiment 132, wherein the one or more control modules comprise a pressure-control module comprising a pressure source configured to deliver sterile gas to the preparation vessel in order to cause pressure to be applied to the cell suspension.

134. The system of any one of embodiments 125-133, wherein the one or more processors are configured to cause the cell suspension to be heated or cooled inside the preparation vessel.

135. The system of embodiment 134, wherein the temperature control module comprises one or more thermoelectric temperature control devices configured to heat or cool a part of the receiver configured to contact the preparation vessel.

136. The system of embodiment 135, wherein the part of the receiver configured to contact the preparation vessel is a conductive jacket configured to conduct heat to and from the preparation vessel.

137. The system of any one of embodiments 125-136, wherein one or more processors are configured to cause the cell suspension to be agitated inside the preparation vessel such that cells are homogeneously distributed in the cell suspension.

138. The system of embodiment 137, wherein the one or more control modules comprises an agitation control module comprising an agitation plate configured to be driven by one or more motors, the agitation plate configured to cause agitation of all or part of the receiver.

139. The system of any one of embodiments 125-138, wherein the flow control module is configured to cause one or more valves to control flow of the cell suspension to flow from the input container through the disposable assembly to the output container.

140. The system of any one of embodiments 125-139, wherein the flow control module is configured to cause the cell suspension to flow at a target fluid speed.

141. The system of any one of embodiments 125-140, further comprising an input device configured to receive instructions from the user, wherein the one or more processors are configured to operate one or more of the control modules in response to the instructions.

142. The system of embodiment 141, wherein the input device comprises a touch-screen display configured to transmit signals to one or more of the control modules in response to detecting contact by a user.

143. The system of any one of embodiments 141 and 142, wherein the input device comprises an agitation speed adjustment device configured to control a speed of a motor that causes agitation of the cell suspension inside the preparation vessel.

144. The system of any one of embodiments 125-143, wherein the preparation vessel is configured to hold up to 10 liters of the cell suspension.
145. The system of any one of embodiments 125-144, wherein the preparation vessel is configured to allow a pressure of up to 120 psi to be applied to the cell suspension.
146. The system of any one of embodiments 125-145, wherein the preparation vessel comprises a first inlet configured to be fluidly connected to the cell suspension input container to receive flow of the cell suspension.
147. The system of any one of embodiments 125-146, wherein the preparation vessel comprises a second inlet configure to be fluidly connected to a pressure source to receive flow of sterile gas to the preparation vessel in order to cause pressure to be applied to the cell suspension.
148. The system of any one of embodiments 125-147, wherein the preparation vessel comprises an outlet configured to be fluidly connected to the constriction cartridge.
149. The system of any one of embodiments 125-148, wherein the constriction cartridge comprises an inlet configured to be fluidly connected to the preparation vessel.
150. The system of any one of embodiments 125-149, wherein the constriction cartridge comprises a housing portion configured to hold the component comprising the one or more cell-deforming constrictions and to direct flow of the cell suspension into the component comprising the one or more cell-deforming constrictions.
151. The system of any one of embodiments 125-150, wherein the constriction cartridge is configured such that the component is held between a base portion and a removable lid portion.
152. The system of embodiment 151, wherein the removable lid portion is configured to be slidably attachable to and removable from the base portion without the use of tools.
153. The system of any one of embodiments 125-152, wherein the constriction cartridge is configured to hold the component in place by one or more o-rings.
154. The system of any one of embodiments 125-153, wherein the constriction cartridge is configured to direct flow of the cell suspension into the component through one or more o-rings.
155. The system of any one of embodiments 125-154, wherein the constriction cartridge comprises an outlet configured to be fluidly connected to the output container.
156. The system of any one of embodiments 125-155, wherein the one or more processors are configured to receive signals from one or more sensors and to automatically control one or more of a pressure, temperature, and agitation of the cell suspension in accordance with the signals received.
157. The system of embodiment 156, wherein the one or more sensors are included in the disposable assembly.
158. The system of any one of embodiments 156 and 157, wherein the one or more sensors comprises a temperature sensor configured to monitor a temperature of the cell suspension.
159. The system of embodiment 158, wherein the temperature sensor comprises a thermistor included in the disposable assembly and configured to be attached to the receiver.
160. The system of any one of embodiments 156-159, wherein the one or more sensors comprises a bubble sensor configured to monitor flow of the cell suspension.
161. The system of any one of embodiments 156-160, wherein the one or more sensors comprises a pressure sensor configured to monitor a pressure applied to the cell suspension.
162. The system of any one of embodiments 125-161, further comprising a memory configured to store log information comprising one or more of pressure, temperature, agitation, flow, and time elapsed while the cell suspension is located in one or both of the preparation vessel and the constriction cartridge.
163. The system of any one of embodiments 125-162, further comprising a display configured to display information comprising one or more of pressure, temperature, agitation, flow, and time elapsed while the cell suspension is located in one or both of the preparation vessel and the constriction cartridge.
164. The system of any one of embodiments 125-163, further comprising a network communication interface configured to transmit information to a remote computing device, the information comprising including one or more of pressure, temperature, agitation, flow, and time elapsed while the cell suspension is located in one or both of the preparation vessel and the constriction cartridge.
165. The system of any one of embodiments 125-164, wherein the system is configured to be able to be moved from a first location to a second location without disassembly.
166. The system of embodiment 165, wherein moving the system without disassembly comprises moving the platform without detaching the holder, receiver, or one or more processors from the platform.
167. The system of any one of embodiments 125-166, wherein the system is less than 2 feet in height.
168. The system of any one of embodiments 125-167, wherein the system has a footprint of less than 3 feet by 2 feet.
169. The system of any one of embodiments 125-168, wherein the system is less than 60 pounds.
170. The system of any one of embodiments 125-169, wherein the system is configured to be sterilizable.
171. A disposable assembly for use in a system for delivering a payload to a cell, the assembly comprising:
  a preparation vessel configured to hold cell suspension as it is prepared for passage through one or more cell-deforming constrictions; and
  a constriction cartridge configured to be in fluid communication with the preparation vessel, the constriction cartridge configured to house a component comprising the one or more cell-deforming constrictions, wherein the cell-deforming constrictions are configured to cause perturbations in a cell membrane that allow entry of a payload into the cell; and
  a cell suspension output container configured to be in fluid communication with the constriction cartridge.
172. The assembly of embodiment 171, wherein the disposable assembly is configured to be able to be connected to and disconnected from the system without the use of tools.
173. The assembly of any one of embodiments 171 and 172, wherein:
  the component comprising the one or more cell-deforming constrictions is a microfluidic chip comprising microfluidic channels, wherein the microfluidic channels comprise the one or more cell-deforming constrictions; and
  the constriction cartridge is a microfluidic chip cartridge configured to house the microfluidic chip.
174. The assembly of any one of embodiments 171-173, wherein:
  the component comprising the one or more cell-deforming constrictions is a filter comprising a plurality of cell-deforming constrictions; and the constriction cartridge is a filter cartridge configured to house the filter.

175. The assembly of any one of embodiments 171-174, wherein the system is a tabletop system.

176. The assembly of any one of embodiments 171-175, wherein connecting the assembly to the system without the use of tools comprises fluidly connecting the assembly to the system such that the system may receive flow of the cell suspension from the system.

177. The assembly of any one of embodiments 171-176, wherein connecting the assembly to the system without the use of tools comprises electronically connecting one or more sensors of the assembly to one or more controllers of the system.

178. The assembly of embodiment 177, wherein the one or more sensors comprise a temperature sensor configured to monitor a temperature of the cell suspension inside the preparation vessel and to transmit data regarding the temperature to a temperature control module of the system.

179. The assembly of any one of embodiments 177 and 178, wherein the one or more sensors comprise a pressure sensor configured to monitor a pressure applied to the cell suspension and to transmit data regarding the pressure to a pressure control module of the system.

180. The assembly of any one of embodiments 177-179, wherein the one or more sensors comprise a bubble sensor configured to monitor flow of the cell suspension through the assembly.

181. The assembly of any one of embodiments 171-180, wherein the constriction cartridge comprises an inlet configured to be fluidly connected to the preparation vessel.

182. The assembly of any one of embodiments 171-181, wherein the constriction cartridge comprises a housing portion configured to hold the component comprising the one or more cell-deforming constrictions and to direct flow of the cell suspension into the component comprising the one or more cell-deforming constrictions.

183. The assembly of any one of embodiments 171-182, wherein the constriction cartridge is configured such that the component is held between a base portion and a removable lid portion.

184. The assembly of embodiment 183, wherein the removable lid portion is configured to be slidably attachable to and removable from the base portion.

185. The assembly of any one of embodiments 171-184, wherein the constriction cartridge is configured to hold the component in place by one or more o-rings.

186. The assembly of any one of embodiments 171-185, wherein the constriction cartridge is configured to direct flow of the cell suspension into the component through one or more o-rings.

187. The assembly of any one of embodiments 171-186, wherein the constriction cartridge comprises an outlet configured to be fluidly connected to the output container.

188. The assembly of any one of embodiments 171-187, wherein the constriction cartridge is configured to house a second component comprising one or more cell-deforming constrictions and to direct flow of the cell suspension fluid through the second component in parallel with the first component.

189. The assembly of any one of embodiments 171-188, wherein the assembly is configured to be sterilizable.

190. A method for delivering a payload to a cell, the method comprising:
providing a cell in a cell suspension;
passing the cell suspension into a preparation vessel at a tabletop system;
while the cell suspension is in the preparation vessel, preparing the cell suspension including by causing pressure to be applied to the cell suspension;
passing the prepared cell suspension from the preparation vessel through a constriction cartridge of the system, wherein the constriction cartridge is configured to house a component comprising a cell-deforming constriction that causes a perturbation in a membrane of the cell that allows entry of a payload into the cell.

191. The method of embodiment 190, wherein:
the component comprising the one or more cell-deforming constrictions is a microfluidic chip comprising microfluidic channels, wherein the microfluidic channels comprise the one or more cell-deforming constrictions; and
the constriction cartridge is a microfluidic chip cartridge configured to house the microfluidic chip.

192. The method of any one of embodiments 190 and 191, wherein:
the component comprising the one or more cell-deforming constrictions is a filter comprising a plurality of cell-deforming constrictions; and
the constriction cartridge is a filter cartridge configured to house the filter.

193. The method of any one of embodiments 190-192, further comprising causing the payload to come into contact with the cell suspension before flow of at least part of the cell suspension through the constriction cartridge.

194. The method of any one of embodiments 190-193, further comprising causing the payload to come into contact with the cell suspension following flow of at least part of the cell suspension through the constriction cartridge.

195. The method of any one of embodiments 190-194, further comprising, attaching to the system a disposable assembly comprising the preparation vessel and the constriction cartridge.

196. The method of embodiment 195, wherein attaching the disposable assembly comprises attaching the disposable assembly without the use of tools.

197. The method of any one of embodiments 195 and 196, wherein attaching the disposable assembly comprises inserting the preparation vessel into a receiver of the system configured to receive the preparation vessel.

198. The method of any one of embodiments 195-197, wherein attaching the disposable assembly comprises attaching one or more sensors included in the disposable assembly, such that the sensors are configured to send signals to the system.

199. The method of embodiment 198, wherein the one or more sensors comprises a temperature sensor configured to monitor a temperature of the cell suspension.

200. The method of embodiment 199, wherein the temperature sensor comprises a temperature probe configured to be attached to the receiver.

201. The method of any one of embodiments 198-200, wherein the one or more sensors comprises a bubble sensor configured to monitor flow of the cell suspension.

202. The method of any one of embodiments 198-201, wherein the one or more sensors comprises a pressure sensor configured to monitor a pressure applied to the cell suspension.

203. The method of any one of embodiments 190-202, wherein preparing the cell suspension comprises agitating the cell suspension inside the preparation vessel to homogeneously distribute the cells in the cell suspension.

204. The method of embodiment 203, wherein agitating the cell suspension comprises monitoring agitation of the cell suspension.

205. The method of any one of embodiments 190-204, wherein preparing the cell suspension comprises heating or cooling the cell suspension inside the preparation vessel.

206. The method of embodiment 205, wherein heating or cooling the cell suspension comprises using a thermoelectric temperature control device to heat or cool part of a receiver containing the preparation vessel.

207. The method of any one of embodiments 205 and 206, wherein heating or cooling the cell suspension comprises monitoring a temperature of the cell suspension as it is heated or cooled.

208. The method of any one of embodiments 190-207, wherein causing pressure to be applied to the cell suspension comprises monitoring a pressure as it is applied to the cell suspension.

209. The method of any one of embodiments 190-208, wherein providing the cell in a cell suspension comprises providing the cell suspension in an input container.

210. The method of any one of embodiments 190-209, comprising passing the cell suspension from the constriction cartridge into an output container.

211. The method of any one of embodiments 190-210, comprising, prior to passing the cell suspension into the disposable assembly, performing an integrity check on the disposable assembly.

212. The method of embodiment 211, wherein performing an integrity check on the disposable assembly comprises pressurizing a gas inside the disposable assembly and monitoring a pressure of the pressurized gas for a predetermined period of time.

213. The method of any one of embodiments 190-212, comprising, prior to passing the cell suspension through the disposable assembly, passing a primer solution through the disposable assembly.

214. The method of any one of embodiments 190-213, further comprising:
provide a supply of blood comprising a first plurality of types of cells;
isolating a target type of cells from among the first plurality of types of cells;
suspending the isolated target type of cells in a delivery material to create the cell suspension.

215. The method of embodiment 214, further comprising:
washing processed cells following passage through the cell-deforming constriction to remove the delivery material;
suspending the washed processed cells in a buffer material for cryopreservation.

216. A system for delivering a payload through a cell membrane, the system comprising:
a preparation vessel configured to contain a cell suspension, wherein the suspension comprises cells;
a constriction cartridge fluidly connected to the preparation vessel;
a touch-screen display;
one or more processors; and
a memory configured to store instructions executable by the one or more processors to cause the system to:
detect a contact on the display at a location corresponding to an icon for initiating a process for delivering a payload through membranes of cells in the cell suspension; and
in accordance with detecting the contact:
cause a temperature of the cell suspension inside the preparation vessel to be adjusted;
cause pressure to be applied to the cell suspension inside the preparation vessel; and
pass the cell suspension from the preparation vessel through a constriction in a component housed in the constriction cartridge, wherein the constriction is a cell-deforming constriction that causes perturbations in membrane of the cells in the cell suspension that allow entry of the payload into the cells.

217. The system of embodiment 216, wherein the instructions are executable by the one or more processors to cause the system to:
while adjusting a temperature of the suspension inside the preparation vessel:
display an indication of a current pressure applied to the cell suspension;
display an indication of a current temperature of the cell suspension; and
display a dynamic indication of an elapsed time for the payload delivery process.

218. The system of embodiment 217, wherein the instructions are executable by the one or more processors to cause the system to:
while passing the cell suspension through the constriction cartridge:
continue to display the indication of a current pressure applied to the cell suspension;
continue to display the indication of a current temperature of the cell suspension;
continue to display the dynamic indication of an elapsed time for the payload delivery process; and
display a dynamic indication of an elapsed time for the process of passing the cell suspension through the constriction cartridge.

219. The system of embodiment 218, wherein the instructions are executable by the one or more processors to cause the system to:
detect that the payload delivery process is complete; and
in accordance with detecting that the payload delivery process is complete:
cease to display the dynamic indication of an elapsed time for the payload delivery process;
cease to display the dynamic indication of an elapsed time for the process of passing the cell suspension through the constriction cartridge;
display an indication of a total elapsed time for the payload delivery process; and
display an indication of a total elapsed time for the process of passing the cell suspension through the constriction cartridge.

220. The system of any one of embodiments 216-219, wherein heating or cooling the cell suspension inside the preparation vessel is performed in accordance with detecting a contact on the display at a location corresponding to an icon for performing a heating or cooling process.

221. The system of any one of embodiments 216-220, wherein causing pressure to be applied to the cell suspension inside the preparation vessel comprises delivering pressurized gas to the preparation vessel at a pressure indicated by one or more contacts detected on the display at a location corresponding to an icon for setting a pressure.

222. The system of any one of embodiments 216-221, wherein:
the instructions are executable by the one or more processors to cause the system to agitate the cell suspension inside the preparation vessel; and
agitating the cell suspension inside the preparation vessel is performed in accordance with detecting a contact on the display at a location corresponding to an icon for performing an agitation process.

223. The system of any one of embodiments 216-222, wherein the instructions are executable by the one or more processors to cause the system to:
in accordance with detecting that a disposable assembly is not connected to the system, display an instruction to connect the disposable assembly;
in accordance with detecting that the disposable assembly has been connected to the system, cease to display the instruction to connect the disposable assembly.

224. The system of embodiment 223, wherein the instructions are executable by the one or more processors to cause the system to:
in accordance with detecting that a first portion of the disposable assembly has been connected:
cease to display a first page of the instruction, wherein the first page comprises an instruction to connect the first portion of the disposable assembly; and
replace display of the first page of the instruction with display of a second page of the instruction, wherein the second page comprises an instruction to connect a second portion of the disposable assembly 225. The system of any one of embodiments 216-224, wherein the instructions are executable by the one or more processors to cause the system to:
detect a contact on the display at a location corresponding to an icon for initiating an integrity test;
in accordance with detecting the contact, initiate the integrity test and display an indication of a current pressure and an indication of an elapsed time for the integrity test.

226. The system of any one of embodiments 216-225, wherein the instructions are executable by the one or more processors to cause the system to:
detect a contact on the display at a location corresponding to an icon for initiating a priming process;
in accordance with detecting the contact:
pass a primer solution through the preparation vessel and the constriction cartridge; and
display a current temperature of the primer solution during the priming process.

What is claimed is:

1. An assembly for use in a system for delivering a payload to a cell, the assembly comprising:
a preparation vessel configured to hold a cell suspension as it is prepared for passage through more than one cell-deforming constrictions, each of the more than one cell-deforming constrictions having a smaller diameter than a cell of the cell suspension;
a constriction cartridge configured to be in fluid communication with the preparation vessel, the constriction cartridge comprising a housing portion configured to releasably couple to a component comprising the more than one cell-deforming constrictions, the housing portion also configured to direct flow of the cell suspension into the component comprising the more than one cell-deforming constrictions, wherein the more than one cell-deforming constrictions are configured to cause perturbations in a cell membrane that allow entry of a payload into the cell; and
a tube comprising a first end and a second end, wherein the first end is configured to fluidly connect with the preparation vessel and the second end is configured to fluidly connect with the constriction cartridge.

2. The assembly of claim 1, wherein the assembly is configured to be able to be connected to and disconnected from the system without the use of tools.

3. The assembly of claim 1, wherein:
the component comprising the more than one cell-deforming constrictions is a microfluidic chip comprising microfluidic channels, wherein the microfluidic channels comprise the more than one cell-deforming constrictions; and
the constriction cartridge is a microfluidic chip cartridge configured to house the microfluidic chip.

4. The assembly of claim 1, wherein:
the component comprising the more than one cell-deforming constrictions is a filter comprising a plurality of cell-deforming constrictions; and
the constriction cartridge is a filter cartridge configured to house the filter.

5. The assembly of claim 1, wherein the system is a tabletop system.

6. The assembly of claim 2, wherein connecting the assembly to the system without the use of tools comprises fluidly connecting the assembly to the system such that the system may receive flow of the cell suspension from the system.

7. The assembly of claim 6, wherein connecting the assembly to the system without the use of tools comprises electronically connecting a disposable sensor assembly to one or more controllers of the system, the disposable sensor assembly comprising a sensor releasably coupled around the second end of the tube and configured to monitor the cell suspension.

8. The assembly of claim 7, wherein the disposable sensor assembly further comprises a temperature sensor configured to monitor a temperature of the cell suspension inside the preparation vessel and to transmit data regarding the temperature to a temperature control module of the system.

9. The assembly of claim 7, wherein the disposable sensor assembly further comprises a pressure sensor configured to monitor a pressure applied to the cell suspension and to transmit data regarding the pressure applied to the cell to a pressure control module of the system.

10. The assembly of claim 9, wherein the pressure sensor is configured to monitor a pressure inside the preparation vessel and to transmit data regarding the pressure inside the preparation vessel to the pressure control module of the system.

11. The assembly of claim 7, wherein the sensor is a bubble sensor configured to monitor flow of the cell suspension through the tube.

12. The assembly of claim 1, wherein the constriction cartridge comprises an inlet configured to be fluidly connected to the preparation vessel via the tube.

13. The assembly of claim 1, wherein the constriction cartridge is configured such that the component is held between a base portion and a removable lid portion.

14. The assembly of claim 13, wherein the removable lid portion is configured to be slidably attachable to and removable from the base portion.

15. The assembly of claim 1, wherein the constriction cartridge is configured to hold the component in place by one or more o-rings.

16. The assembly of claim 1, wherein the constriction cartridge is configured to direct flow of the cell suspension into the component through one or more o-rings.

17. The assembly of claim 1, further comprising a cell suspension output container configured to be in fluid communication with an outlet of the constriction cartridge.

18. The assembly of claim 1, wherein the constriction cartridge is configured to releasably couple to a second component comprising more than one cell-deforming constrictions and to direct flow of the cell suspension fluid through the second component in parallel with the first component.

19. The assembly of claim 1, wherein the assembly is configured to be sterilizable by one or more of: gamma sterilization, autoclaving, or ethylene oxide sterilization.

20. The assembly of claim 1, wherein the tube is translucent or transparent and is configured to be seated in a cavity of a sensor of the system, such that the tube is in an optical path of the sensor.

21. The assembly of claim 1, wherein the preparation vessel comprises a flexible plastic bag.

22. The assembly of claim 7, wherein the constriction cartridge is configured to be releasably coupled to the disposable sensor assembly by one or more clips protruding from the disposable sensor assembly.

\* \* \* \* \*